(12) United States Patent
Nock et al.

(10) Patent No.: US 10,201,333 B2
(45) Date of Patent: Feb. 12, 2019

(54) MRI BIOPSY SYSTEM

(71) Applicant: Devicor Medical Products, Inc., Cincinnati, OH (US)

(72) Inventors: Andrew P. Nock, Dayton, OH (US); Trevor W. V. Speeg, Williamsburg, OH (US); Jessica P. Leimbach, Cincinnati, OH (US); Michael E. Henley, Liberty Township, OH (US); Brian M. Ruffner, Maineville, OH (US); Robert M. Householder, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 536 days.

(21) Appl. No.: 14/862,540

(22) Filed: Sep. 23, 2015

(65) Prior Publication Data

US 2016/0081676 A1 Mar. 24, 2016

Related U.S. Application Data

(60) Provisional application No. 62/076,832, filed on Nov. 7, 2014, provisional application No. 62/054,523, filed on Sep. 24, 2014.

(51) Int. Cl.
*A61B 5/00* (2006.01)
*A61B 10/02* (2006.01)
(Continued)

(52) U.S. Cl.
CPC .......... *A61B 10/0275* (2013.01); *A61B 5/055* (2013.01); *A61B 5/064* (2013.01); *A61B 2010/0208* (2013.01); *G01R 33/285* (2013.01)

(58) Field of Classification Search
CPC ..... A61B 10/0275; A61B 5/064; A61B 5/055; A61B 2010/0208; G01R 33/285
See application file for complete search history.

(56) References Cited

U.S. PATENT DOCUMENTS 4,901,938 A 2/1990 Cantley et al.
5,074,863 A 12/1991 Dines
(Continued)

OTHER PUBLICATIONS

International Search Report and Written Opinion dated Jan. 5, 2016 for Application No. PCT/US2015/051664, 9 pgs.
(Continued)

*Primary Examiner* — Joel Lamprecht
(74) *Attorney, Agent, or Firm* — Frost Brown Todd LLC

(57) ABSTRACT

A biopsy system, including a biopsy device, a localization assembly, and a control module. The localization assembly is configured to orient the biopsy device relative to a patient. The control module is communication with the biopsy device. The control module is configured to operate a plurality of functional features of the biopsy device. The control module includes a cable and a cable management assembly. The cable management assembly includes a pair of cable management plates, and a weight. Each of the pair cable management plates are disposed substantially parallel to each other and define a space therebetween. The weight is configured to move within the space defined by the pair of cable management plates. The weight is attachable to the cable of the control module and is further configured to slide axially along the cable.

18 Claims, 49 Drawing Sheets

(51) Int. Cl.
*A61B 5/055* (2006.01)
*A61B 5/06* (2006.01)
*G01R 33/28* (2006.01)

(56) References Cited

U.S. PATENT DOCUMENTS

| | | | |
|---|---|---|---|
| 5,526,822 | A | 6/1996 | Burbank et al. |
| 5,928,164 | A | 7/1999 | Burbank et al. |
| 6,017,316 | A | 1/2000 | Ritchart et al. |
| 6,086,544 | A | 4/2000 | Hibner et al. |
| 6,162,187 | A | 12/2000 | Buzzard et al. |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 7,204,825 | B2 | 4/2007 | Cimino et al. |
| 7,442,171 | B2 | 10/2008 | Stephens et al. |
| 7,507,210 | B2 | 3/2009 | Hibner et al. |
| 7,648,466 | B2 | 1/2010 | Stephens et al. |
| 7,693,567 | B2 | 4/2010 | Tsonton et al. |
| 7,831,290 | B2 | 11/2010 | Hughes et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,241,226 | B2 | 8/2012 | Hibner et al. |
| 8,277,394 | B2 | 10/2012 | Hibner |
| 8,328,732 | B2 | 12/2012 | Parihar et al. |
| 8,454,531 | B2 | 6/2013 | Speeg et al. |
| 8,480,595 | B2* | 7/2013 | Speeg ............... A61B 10/0275 600/568 |
| 8,568,333 | B2 | 10/2013 | Hibner et al. |
| 8,617,084 | B2 | 12/2013 | Parihar et al. |
| 8,702,623 | B2 | 4/2014 | Parihar et al. |
| 8,764,680 | B2 | 7/2014 | Rhad et al. |
| 8,801,742 | B2 | 8/2014 | Rhad et al. |
| 8,858,465 | B2 | 10/2014 | Fiebig |
| 8,938,285 | B2 | 1/2015 | Fiebig et al. |
| 9,095,326 | B2 | 8/2015 | Ritchie et al. |
| 2006/0074345 | A1 | 4/2006 | Hibner |
| 2006/0264921 | A1 | 11/2006 | Deutsch et al. |
| 2008/0097239 | A1* | 4/2008 | Chang ............... A61B 17/1204 600/562 |
| 2008/0214955 | A1 | 9/2008 | Speeg et al. |
| 2008/0221478 | A1* | 9/2008 | Ritchie ............ A61B 10/0275 600/562 |
| 2009/0131821 | A1 | 5/2009 | Speeg et al. |
| 2010/0152610 | A1 | 6/2010 | Parihar et al. |
| 2010/0160818 | A1 | 6/2010 | Haberstich et al. |
| 2010/0160819 | A1 | 6/2010 | Parihar et al. |
| 2012/0065542 | A1 | 3/2012 | Hibner et al. |
| 2013/0053724 | A1 | 2/2013 | Fiebig et al. |
| 2013/0144188 | A1 | 6/2013 | Fiebig et al. |
| 2013/0218047 | A1 | 8/2013 | Fiebig et al. |
| 2013/0324882 | A1 | 12/2013 | Mescher |
| 2014/0039343 | A1 | 2/2014 | Mescher et al. |
| 2015/0025414 | A1 | 1/2015 | Rhad et al. |
| 2015/0065913 | A1 | 3/2015 | Keller et al. |

OTHER PUBLICATIONS

U.S. Appl. No. 61/566,793, filed Dec. 5, 2011.
U.S. Appl. No. 62/054,523, filed Sep. 24, 2014.
U.S. Appl. No. 62/076,832, filed Nov. 7, 2014.

* cited by examiner

MRI BIOPSY SYSTEM

BACKGROUND

Biopsy samples have been obtained in a variety of ways in various medical procedures including open and percutaneous methods using a variety of devices. Biopsy devices may be used under stereotactic guidance, ultrasound guidance, MRI guidance, PEM guidance, BSGI guidance, or otherwise.

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008, issued as U.S. Pat. No. 8,118,755 on Feb. 21, 2012; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009, issued as U.S. Pat. No. 8,454,531 on Jun. 4, 2013; U.S. Pat. Pub. No. 2010/0113973, entitled "Biopsy Device with Rotatable Tissue Sample Holder," published May 6, 2010, issued as U.S. Pat. No. 8,241,226 on Aug. 14, 2012; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010, issued as U.S. Pat. No. 8,702,623 on Apr. 22, 2014; U.S. Pat. Pub. No. 2010/0317997, entitled "Tetherless Biopsy Device with Reusable Portion," published Dec. 16, 2010, issued as U.S. Pat. No. 8,206,316 on Jun. 26, 2012; U.S. Pat. Pub. No. 2012/0109007, entitled "Handheld Biopsy Device with Needle Firing," published May 3, 2012; U.S. Non-Provisional patent application Ser. No. 13/086,567, entitled "Biopsy Device with Motorized Needle Firing," filed Apr. 14, 2011, published as U.S. Pat. Pub. No. 2012/0265095 on Oct. 18, 2012; U.S. Non-Provisional patent application Ser. No. 13/150,950, entitled "Needle Assembly and Blade Assembly for Biopsy Device," filed Jun. 1, 2011, published as U.S. Pat. Pub. No. 2012/0310110 on Dec. 6, 2012; U.S. Non-Provisional patent application Ser. No. 13/205,189, entitled "Access Chamber and Markers for Biopsy Device," filed Aug. 8, 2011, published as U.S. Pat. Pub. No. 2013/0041256 on Feb. 14, 2013; U.S. Non-Provisional patent application Ser. No. 13/218,656, entitled "Biopsy Device Tissue Sample Holder with Bulk Chamber and Pathology Chamber," filed Aug. 26, 2011, published as U.S. Pat. Pub. No. 2013/0053724 on Feb. 28, 2013; U.S. Provisional Patent App. No. 61/566,793, entitled "Biopsy Device With Slide-In Probe," filed Dec. 5, 2011; and U.S. Non-Provisional patent application Ser. No. 13/483,235, entitled "Control for Biopsy Device," filed May 30, 2012, published as U.S. Pat. Pub. No. 2013/0324882 on Dec. 5, 2013. The disclosure of each of the above-cited U.S. Patent Application Publications, U.S. Non-Provisional Patent Applications, and U.S. Provisional Patent Applications is incorporated by reference herein.

In U.S. Pat. Pub. No. 2005/0283069, entitled "MRI Biopsy Device Localization Fixture" published Dec. 22, 2005, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Merely illustrative z-stop examples are disclosed in U.S. Pat. No. 7,507,210, entitled "Biopsy Cannula Adjustable Depth Stop," issued Mar. 24, 2009, the disclosure of which is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
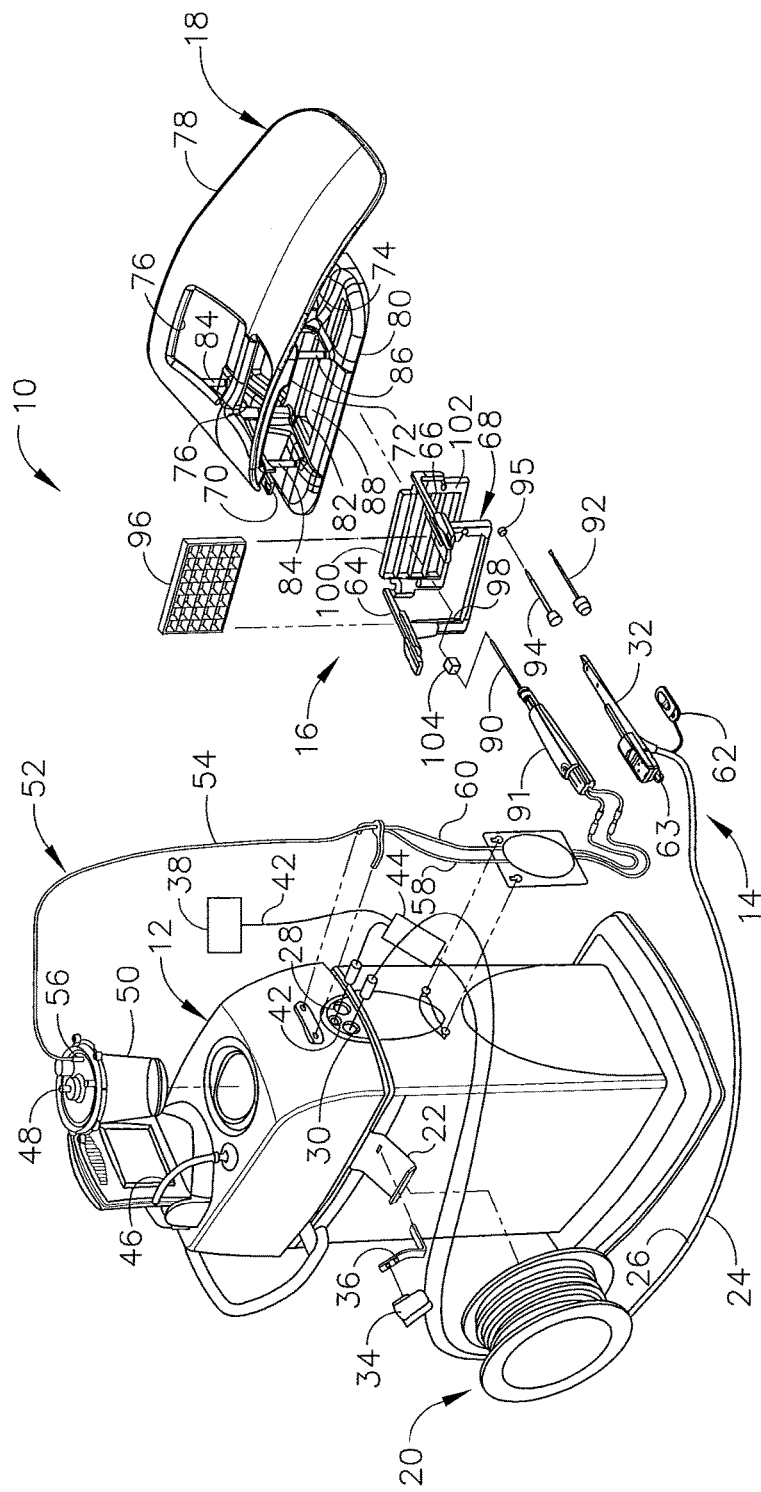
FIG. 1 depicts a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary MRI Biopsy Control Module

Figure 2:
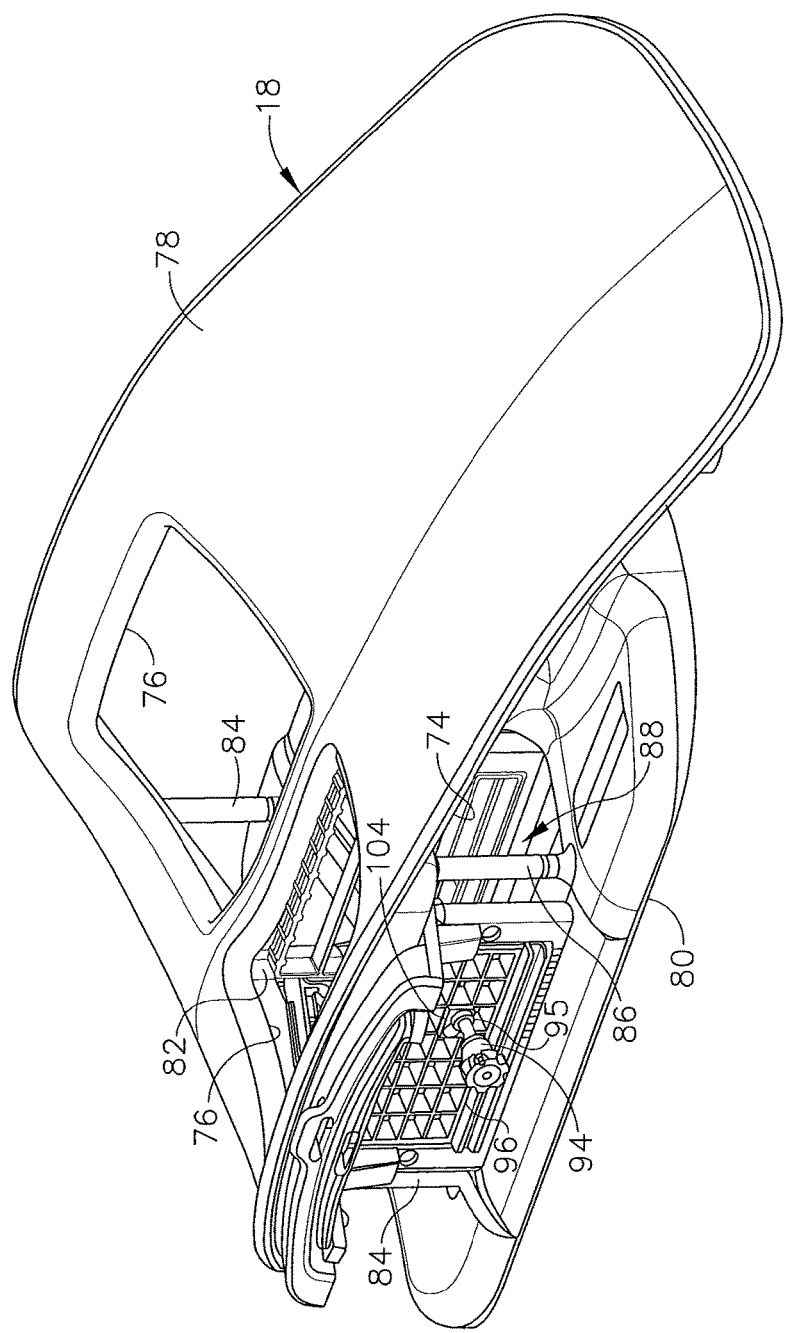
FIG. 2 depicts a perspective view of a breast coil receiving the localization fixture of FIG. 1.
Figure 3:
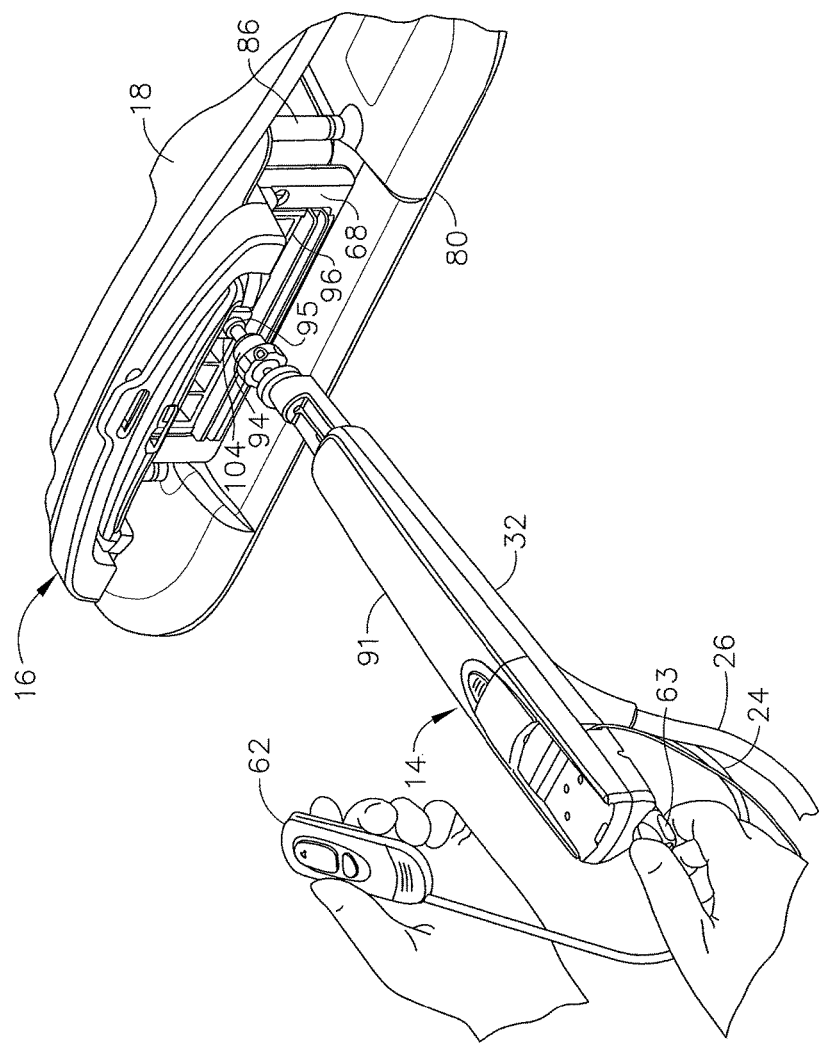
FIG. 3 depicts a perspective view of the biopsy device inserted through the rotatable cube within the cube plate of the localization fixture attached to the breast coil of FIG. 2.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool

(20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. Pat. No. 8,328,732, entitled "Control Module Interface for MRI Biopsy Device," issued Dec. 11, 2012, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Exemplary Localization Assembly

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Exemplary Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 7:
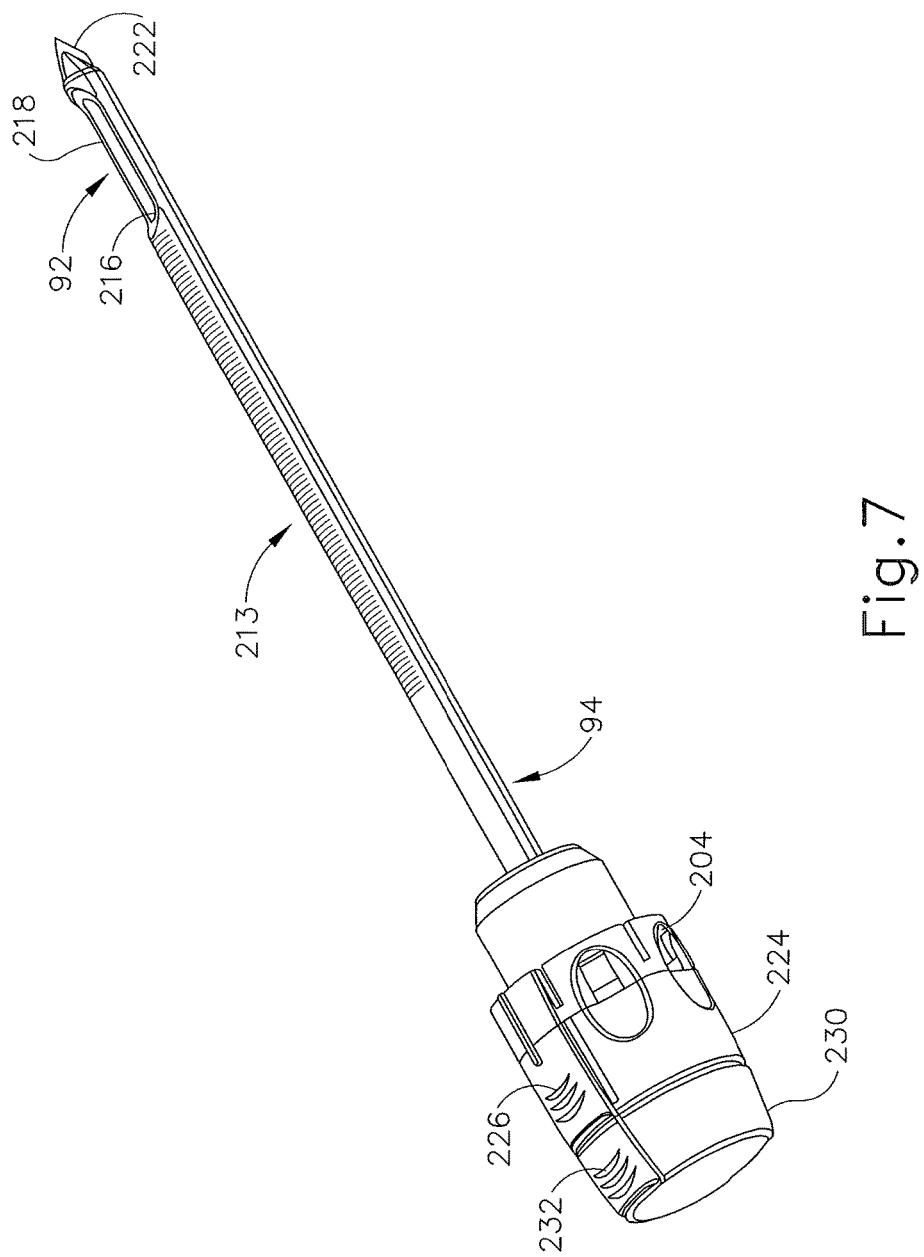
FIG. 7 depicts a perspective view of a obturator and cannula of the biopsy system of FIG. 1.
Figure 8:
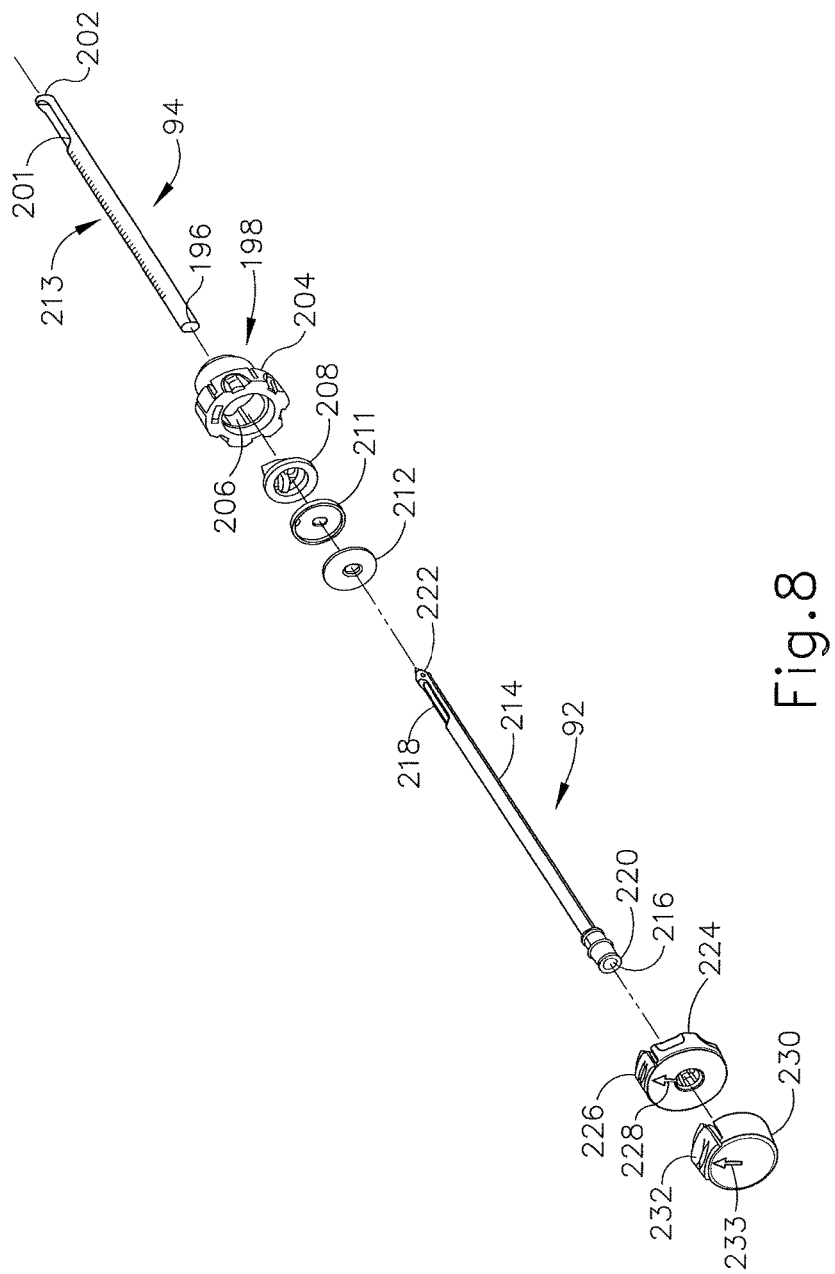
FIG. 8 depicts a perspective exploded view of the obturator and cannula of FIG. 7.
Figure 9:
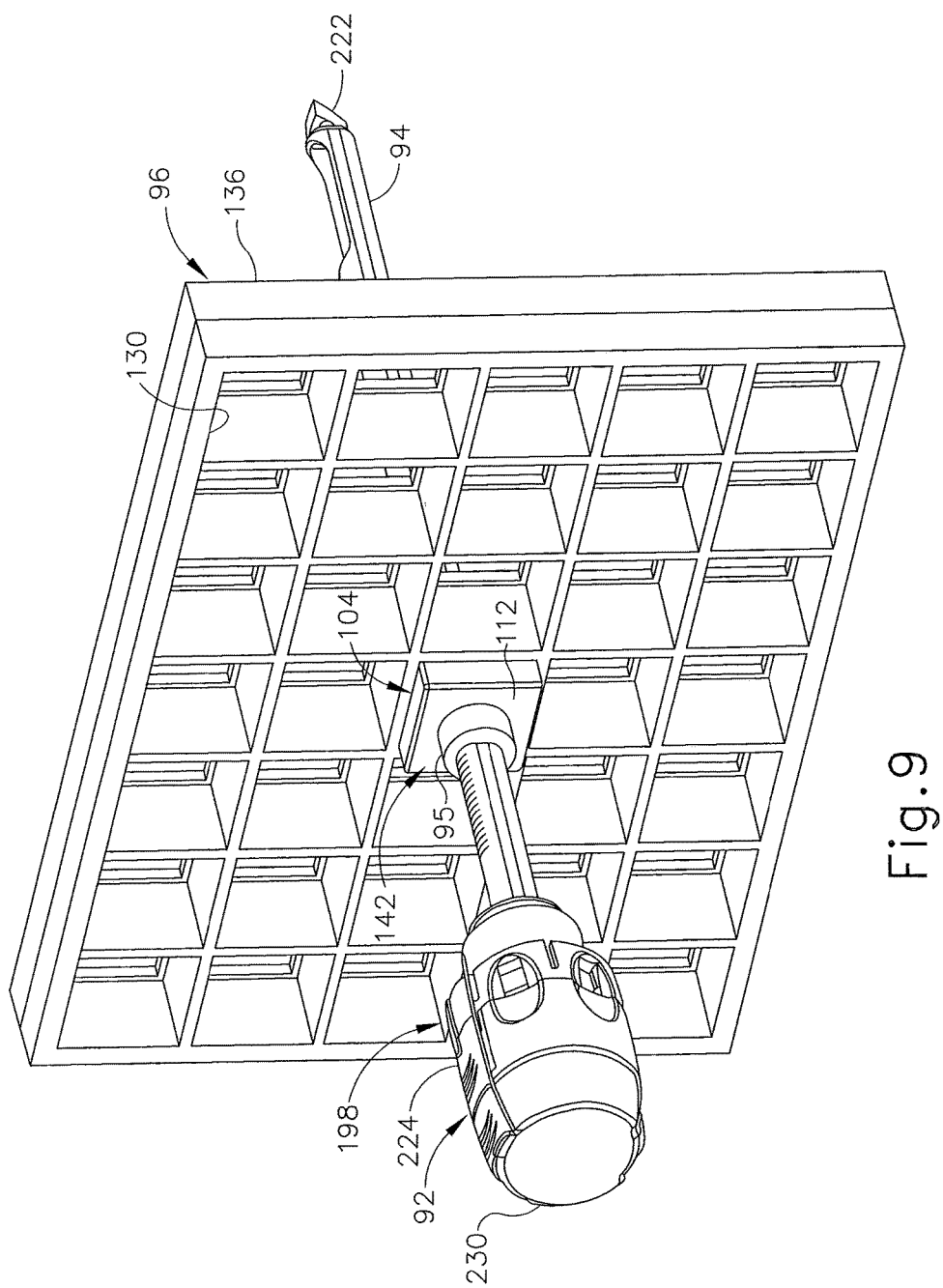
FIG. 9 depicts a perspective view of the obturator and cannula of FIG. 7 with a depth stop device of FIG. 1 inserted through the guide cube and grid plate of FIG. 6.

In the present example, a targeting set (89) comprising cannula (94) and obturator (92) is associated with probe (91). In particular, and as shown in FIGS. 7, 8, and 9, obturator (92) is slid into cannula (94) and the combination is guided through guide cube (104) to the biopsy site within the breast tissue. As shown in FIG. 3, obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (201) proximate to open distal end (202). Cylindrical hub (198) has exteriorly presented thumbwheel (204) for rotating lateral aperture (201). Cylindrical hub (198) has interior recess (206) that encompasses duckbill seal (208), wiper seal (211) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Shaft (214) includes fluid lumen (216) that communicates between imagable side notch (218) and proximal port (220). Shaft (214) is longitudinally sized such that piercing tip (222) extends out of distal end (202) of cannula (94). Obturator thumbwheel cap (224) encompasses proximal port (220) and includes locking feature (226), which includes visible angle indicator (228), that engages cannula thumbwheel (204) to ensure that imagable side notch (218) is registered to lateral aperture (201) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 9, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (201) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (201) of cannula (94) and the lateral aperture of needle (90). Severed tissue samples may be retrieved from biopsy device (14) in any suitable fashion.

Figure 10:
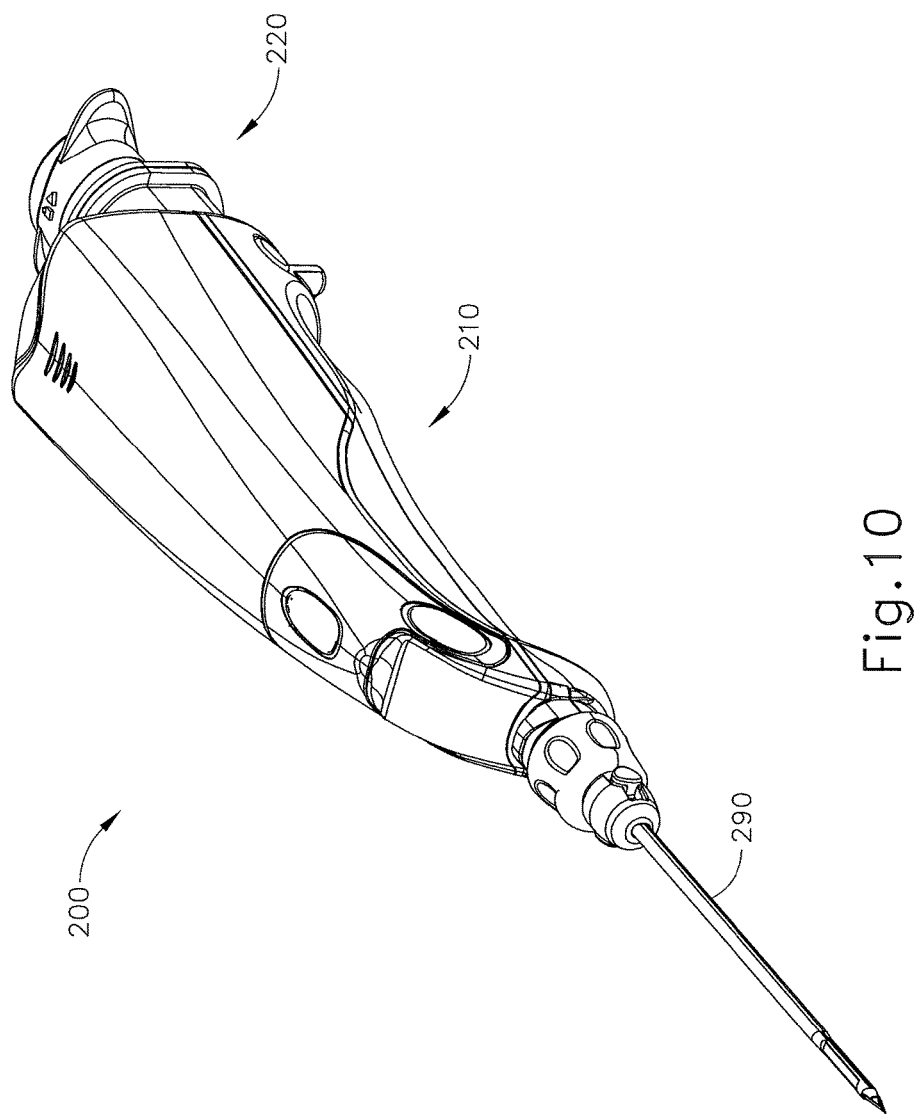
FIG. 10 depicts a perspective view of an exemplary alternative biopsy device that may be used with the biopsy system of FIG. 1.

It should be understood that although biopsy system (10) is discussed above as utilizing disposable probe assembly (91), other suitable probe assemblies and biopsy device assemblies may be utilized. By way of example only, a biopsy device such as the biopsy device (200) shown in FIG. 10 may be used in biopsy system (10). Biopsy device (200) of this example comprises a needle (290) extending distally from a handpiece (210); and a tissue sample holder (220) disposed at a proximal end of handpiece (210). Needle (290)

is configured to operate substantially similar to needle (90) discussed above. For instance, needle (290) is configured to cooperate with a cutter to obtain tissue samples from a biopsy site. Tissue sample holder (220) is configured to store tissue samples received through needle (290). By way of example only, biopsy device (200) may be configured in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein.

Figure 11:
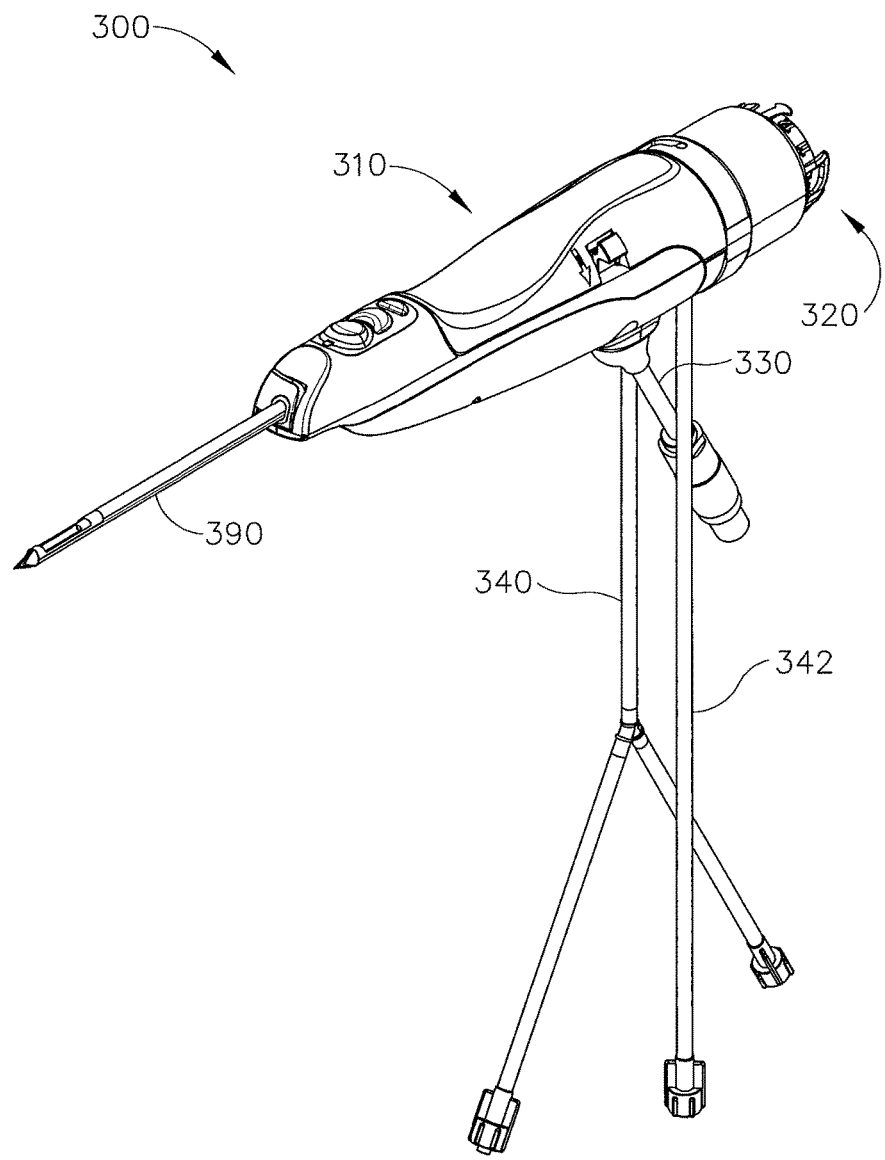
FIG. 11 depicts a perspective view of another exemplary alternative biopsy device that may be used with the biopsy system of FIG. 1.

As yet another merely illustrative example, a biopsy device such as the biopsy device (300) shown in FIG. 11 may be used in biopsy system (10). Biopsy device (300) of this example comprises a needle (390) extending distally from a handpiece (310) and a tissue sample holder (320) disposed at a proximal end of handpiece (310). Needle (290) is configured to operate substantially similar to needle (90) discussed above. For instance, needle (390) is configured to cooperate with a cutter to obtain tissue samples from a biopsy site. Tissue sample holder (320) is configured to store tissue samples received through needle (390). A cable (330) provides communication of electrical power, commands, etc. while conduits (340, 342) provide fluid communication. By way of example only, biopsy device (300) may be configured in accordance with at least some of the teachings of U.S. Pub. No. 2010/0160824, the disclosure of which is incorporated by reference herein; U.S. Patent Pub. No. 2013/0144188, entitled "Biopsy Device with Slide-In Probe," published Jun. 6, 2013, the disclosure of which is incorporated by reference herein; U.S. Patent Pub. No. 2013/0324882, entitled "Control for Biopsy Device," published Dec. 5, 2013, the disclosure of which is incorporated by reference herein; U.S. Patent Pub. No. 2014/0039343, entitled "Biopsy System," published Feb. 6, 2014, the disclosure of which is incorporated by reference herein; and/or U.S. patent application Ser. No. 14/469,761, entitled "Tissue Collection Assembly for Biopsy Device," filed Aug. 27, 2014, the disclosure of which is incorporated by reference herein.

Still other suitable forms of biopsy devices that may be used in conjunction with the various alternative components of system (10) as described herein will be apparent to those of ordinary skill in the art.

IV. Exemplary Guide Cube

In some versions, a guide cube may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 4:
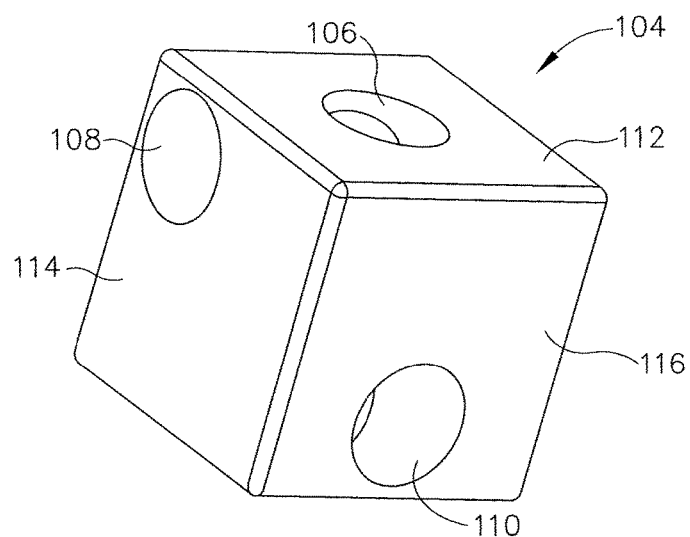
FIG. 4 depicts a perspective view of a two-axis rotatable guide cube of the biopsy system of FIG. 1.
Figure 5:
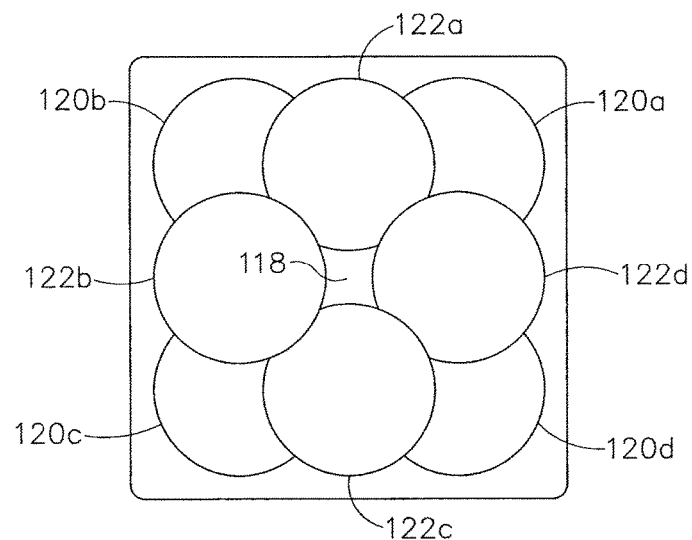
FIG. 5 depicts a diagram of nine guide positions achievable by the two-axis rotatable guide cube of FIG. 4.

In FIG. 4, guide cube (104) includes a central guide hole (106), a corner guide hole (108), and an off-center guide hole (110) that pass orthogonally to one another between respective opposite pairs of faces (112, 114, 116). By selectively rotating guide cube (104) in two axis, one of pairs of faces (112, 114, 116) may be proximally aligned to an unturned position and then selected proximal face (112, 114, 116) optionally rotated a quarter turn, half turn, or three quarter turn. Thereby, one of nine guide positions (118) (i.e., using central guide hole (106)), (120a-120d) (i.e., corner guide hole (108)), (122a-122d) (i.e., using off-center guide hole (110)) may be proximally exposed as depicted in FIG. 5.

Figure 6:
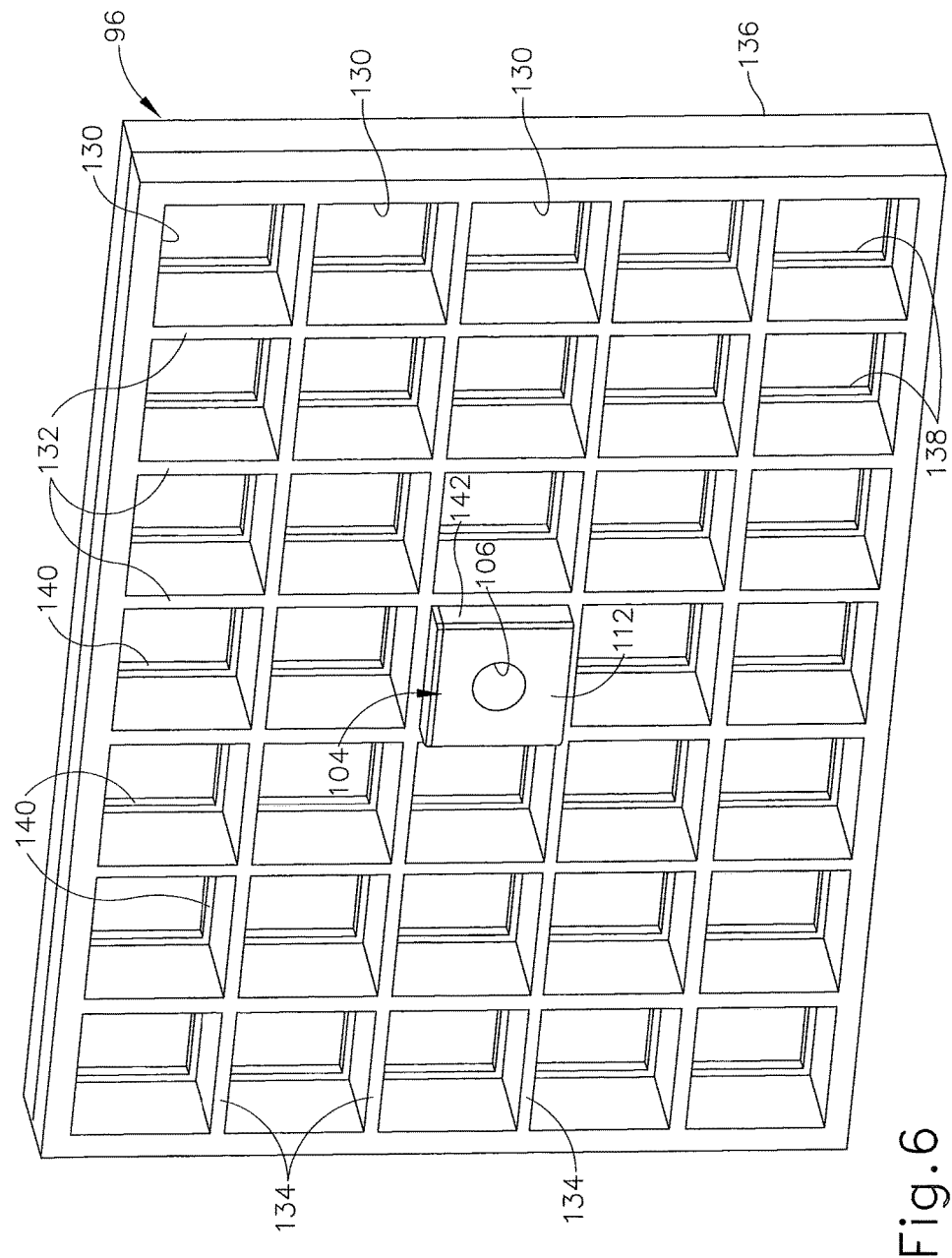
FIG. 6 depicts a perspective view of a two-axis rotatable guide cube into a lateral grid with the backing of the localization fixture of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

In some other versions, guide cube (104) is replaced with an alternative guide cube or other guide structure that is configured and operable in accordance with at least some of the teachings of U.S. patent application Ser. No. 14/335,051, entitled "Biopsy Device Targeting Features," filed Jul. 18, 2014, the disclosure of which is incorporated by reference herein.

V. Exemplary Alternative Targeting Cannulas and Obturators

As a variation of obturator (92) and cannula (94) discussed above, obturator (92) and cannula (94) may be arranged such that a distal end of obturator (92) and cannula (94) present a distal tip having a different profile. In some instances, such a profile may make insertion of obturator (92) and cannula (94) into a patient's breast easier by reducing the force required to penetrate tissue. Such a profile may also make rotation of obturator (92) and cannula (94) within the patient's breast easier by reducing the force required to rotate obturator (92) and/or cannula (94) within a patient's breast. Various examples of how obturator (92) and cannula (94) may be reconfigured to present a distal tip having a more effective profile will be described in greater detail below; while other examples will be apparent to those of ordinary skill in the art according to the teachings herein. It should be understood that the obturator and cannula examples described below may function substantially similar to obturator (92) and cannula (94) described above. In particular, the obturator and cannula examples described below may be used to assist in biopsy device needle targeting within a patient's breast using MRI guidance. It should be understood that the cannula tip examples discussed below may be used with any of the biopsy devices discussed above or disclosed herein.

It should also be understood that the teachings below may be readily combined with the teachings of U.S. patent application Ser. No. 14/335,051, entitled "Biopsy Device Targeting Features," filed Jul. 18, 2014, the disclosure of which is incorporated by reference herein. In other words, the various cannulas and obturators described in U.S. patent application Ser. No. 14/335,051 may be modified in accordance with at least some of the teachings herein in numerous ways as will be apparent to those of ordinary skill in the art in view of the teachings herein. Similarly, the various examples of cannulas and obturators described herein may be modified in accordance with at least some of the teachings in U.S. patent application Ser. No. 14/335,051 in numerous ways as will be apparent to those of ordinary skill in the art in view of the teachings herein.

A. Exemplary Targeting Set with Flexible Cannula

Figure 12:
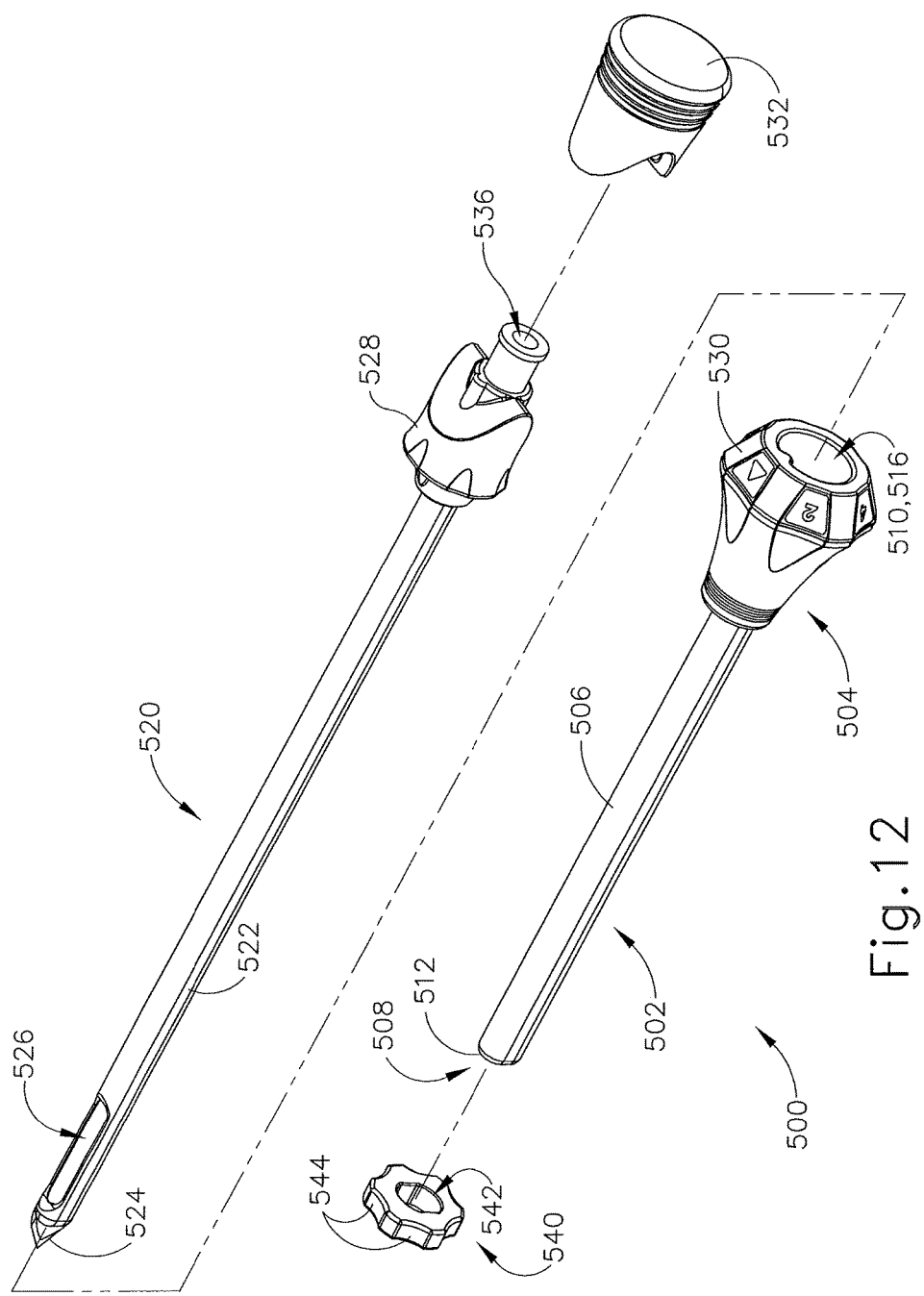
FIG. 12 depicts a perspective exploded view of an exemplary alternative targeting set for use with the biopsy system of FIG. 1.
Figure 13:
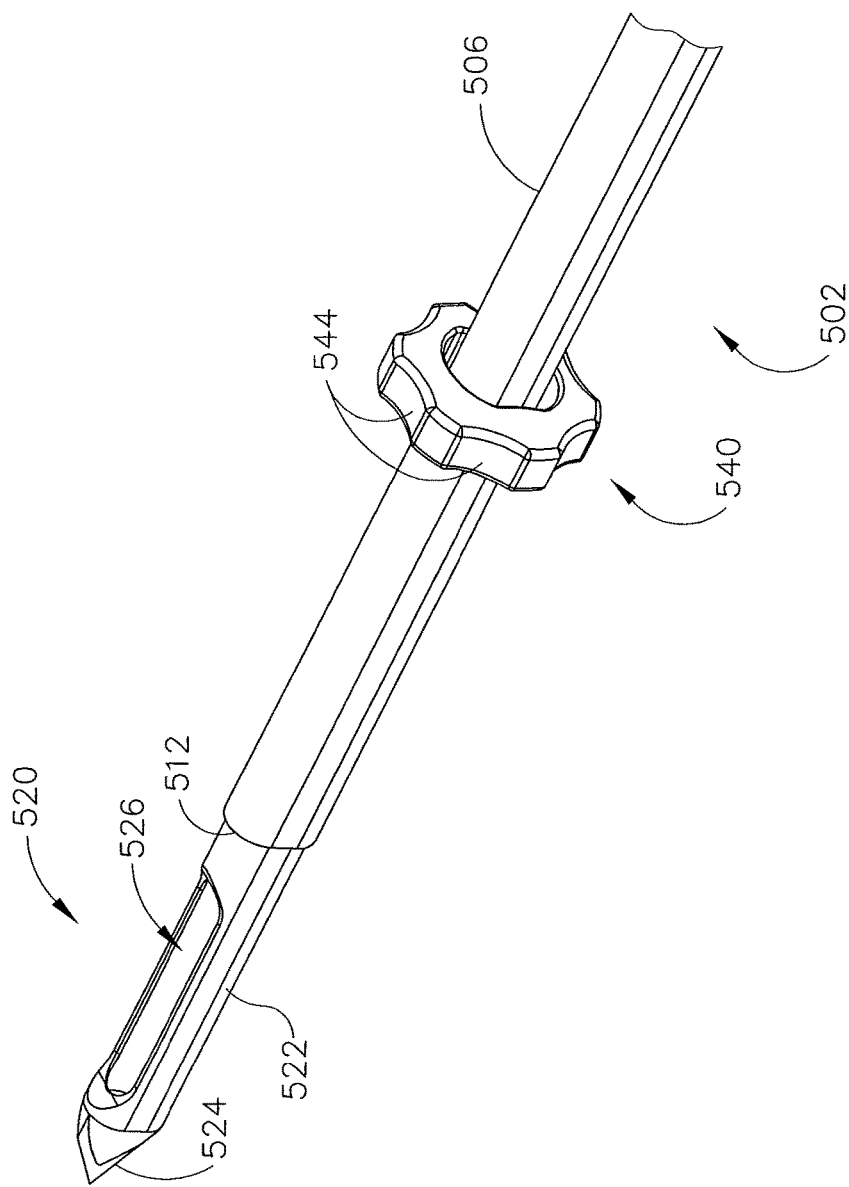
FIG. 13 depicts an enlarged perspective view of and obturator and cannula of the targeting set of FIG. 12 with a depth stop device inserted onto the cannula.

FIGS. 12-13 show an exemplary alternative targeting set (500) that may be used with the biopsy system described above. Targeting set (500) is similar to targeting set (89) described above, except as otherwise noted herein. For instance, targeting set (500) comprises a cannula (502) that is configured to receive obturator (520) and the combination is configured to be guided through a guide cube (e.g., guide cube (104), etc.) to a biopsy site within a patient's breast. Cannula (502) includes a hollow shaft (506) that is proximally attached to a cylindrical hub (504) and has an opening (508) positioned on the distal end of cannula (502). Shaft (506) defines a lumen (510) extending through cannula (502) from the proximal end to the distal end of cannula (502). Shaft (506) is shaped correspondingly to obturator (520) such that obturator (520) may be inserted through lumen (510). Opening (508) of cannula (502) comprises a relatively flat edge (512). Although edge (512) is shown as relatively flat, it should be understood that edge (512) may be beveled, chamfered, or tapered. Of course, edge (512) may take on any other geometry as will be apparent to those of ordinary skill in the art in view of the teachings herein.

Cannula (502) of the present example is substantially opaque. Of course such a feature is merely optional and in other examples cannula (502) may be fully or partially transparent, translucent, and/or have any other suitable optical transmissivity. It should be understood that such transparent features may be included in some examples because it may be desirable for an operator to visualize indicia disposed on obturator (520). Cannula (502) is generally comprised of a relatively thin and flexible material such that shaft (506) may collapse if obturator (520) or other devices are removed from cannula (502). This may enable shaft (506) to provide a self-sealing effect. In other versions, cannula (502) may be rigid such that shaft (506) is configured to maintain its shape upon removal of obturator (520) or other devices from cannula (502).

Cylindrical hub (504) is configured to receive a grip (528) of obturator (520). As can be seen in FIG. 12, cylindrical hub (504) comprises a proximal opening (516) and an index bezel (530). Proximal opening (516) is configured to receive a corresponding protrusion (not shown) of obturator (520). Although not shown, in some examples cylindrical hub (504) also includes one or more retention features that may be configured to engage a corresponding one or more retention features of grip (528). Suitable retention features may include resilient tabs, snap fits, compression fits, detents, and/or etc. In other examples, cylindrical hub (504) may include any other feature configured to selectively attach cylindrical hub (504) to grip (528). In some versions, cylindrical hub (404) includes a wiper seal, a duckbill seal, and/or one or more other kinds of sealing features that substantially prevent proximal backflow of blood and/or other bodily fluids out through proximal opening (516) when obturator (520) is removed from cannula (502) while cannula (502) is disposed in a patient's breast. By way of example only, hub (504) may include one or more sealing features that is/are configured and operable in accordance with at least some of the teachings of U.S. Pat. No. 7,693,567, entitled "MRI Biopsy Apparatus Incorporating a Sleeve and Multi-Function Obturator," issued Apr. 6, 2010, the disclosure of which is incorporated by reference herein. Other suitable features that may be incorporated into hub (504) will be apparent to those of ordinary skill in the art in view of the teachings herein.

Obturator (520) comprises a shaft (522) extending distally from grip (528). Shaft (522) longitudinally sized such that a piercing tip (524) and a lateral aperture (526) positioned on the distal end of obturator (520) extends out of opening (508) of cannula (502). In particular, shaft (522) is sized such that edge (512) of cannula (502) terminates proximally relative to lateral aperture (526) of obturator (520). Because shaft (506) of cannula is relatively thin, the interface between shaft (522) of obturator (520) and edge (512) of cannula (502) may create a streamlined profile thereby reducing the force to penetrate when cannula (502) and obturator (520) are inserted into a breast. It should be understood that in examples where shaft (506) of cannula (502) is relatively thick, a similar streamlined profile may be facilitated by a taper, chamfer, or other feature on the distal end of cannula (502). Alternatively, shaft (522) of obturator (502) may include certain geometric features to facilitate a streamlined transition between shaft (522) of obturator (520) and shaft (506) of cannula (502).

Grip (528) comprises a rubber grip plug (532), which may be selectively removable from grip (528). Although index bezel (530) is associated with cylindrical hub (504), it should be understood that in other examples index bezel (530) is alternatively associated with grip (528). Grip (528) extends proximally from shaft (522), terminating at a proximal opening (536), which may be used as a passage for the insertion of marker delivery devices, MR imagable material, and/or other instruments/materials associated with a biopsy procedure. Rubber grip plug (532) is insertable over at least a portion of grip (528) to close proximal opening (536) when proximal opening (536) is not in use.

As can best be seen in FIG. 13, targeting set (500) may include a depth stop device (540), which may be similar to depth stop device (95) described above. For instance, depth stop device (540) may be inserted onto cannula (502) or obturator (520) to prevent over insertion into a patient's breast. In the present example depth stop device (540) includes an opening (542), which may be sized to similarly to shaft (506) of cannula (502). In particular, depth stop device (540) may be comprised of an elastomeric material such that opening (542) may be slightly undersized relative to outer surface (514) of cannula (502). Accordingly, depth stop device (540) may be positioned at a certain spot on cannula (502) where it may remain by the force of friction generated by the interference between the size of opening (542) of depth stop device (540) and the size of outer surface (514) of cannula (502). In some versions, opening (542) includes obliquely oriented elastomeric webbing that grips the outer surface of cannula (502) when depth stop device (540) is rotated relative to cannula (502). In some other versions, opening (542) includes obliquely oriented rigid fins that dig into the material of cannula (502) when depth stop device (540) is rotated relative to cannula (502), thereby substantially securing the axial position of depth stop device (540) on cannula (502). In addition to or as an alternative to the foregoing, depth stop device (540) may be constructed and operable in accordance with at least some of the teachings of U.S. Pat. No. 7,507,210, entitled "Biopsy Cannula Adjustable Depth Stop," issued Mar. 24, 2009, the disclosure of which is incorporated by reference herein and/or U.S. patent application Ser. No. 14/335,051, entitled "Biopsy Device Targeting Features," filed Jul. 18, 2014, the disclosure of which is incorporated by reference herein. Other suitable forms that depth stop device (540) may take will be apparent to those of ordinary skill in the art in view of the teachings herein.

Depth stop device (540) of the present example also includes a plurality of indentations (544), which may be used assist a user with positioning depth stop device (540). Because cannula (502) is substantially opaque, shaft (506) of cannula (502) may include depth indicia (not shown), which may be used to position depth stop device (540) at a position on cannula (502) corresponding to a desired depth. Of course, in other examples, indicia may be located on elsewhere or simply omitted all together.

B. Exemplary Targeting Set with Piercing Rod and Imaging Rod

FIGS. 14-17 show another exemplary alternative targeting set (2400) that may be used with the biopsy system (10) described above. Targeting set (2400) is similar to targeting set (89) described above, except as otherwise noted herein. For instance, targeting set (2400) comprises a cannula (2402) that is configured to receive obturator (2420, 2450); and the combination is configured to be guided through a guide cube to a biopsy site within a patient's breast. Unlike targeting set (89), targeting set (2400) includes two obturators (2420, 2450), which may be used during different stages of a biopsy procedure as will be described in greater detail below. Cannula (2402) includes a hollow shaft (2406) that is proximally attached to a cylindrical hub (2404) and has an opening (2408) positioned on the distal end of cannula (2402). Shaft (2406) defines a lumen (2410) extending through cannula (2402) from the proximal end to the distal end of cannula (2402). Shaft (2406) is shaped correspondingly to obturators (2420, 2450) such that either obturator (2420, 2450) may be inserted through lumen (2410). In the present example, opening (2408) of cannula (2402) comprises a relatively flat edge (2412). Although edge (2412) is shown as relatively flat, it should be understood that edge (2412) is beveled, tapered, or chamfered in other examples. Of course, edge (2412) may take on any other geometry as will be apparent to those of ordinary skill in the art in view of the teachings herein.

Cannula (2402) of the present example is substantially opaque. Of course, such a feature is merely optional and in other examples cannula (2402) may be fully or partially transparent or have any other suitable optical transmissivity. Cannula (2402) is generally comprised of a relatively thin and flexible material such that shaft (2406) may collapse if obturators (2420, 2450) or other devices are removed from cannula (2402). Of course, in other versions, cannula (2402) may be rigid, semi-rigid, malleable, or have other properties.

Cylindrical hub (2404) is configured to receive a grip (2428) of obturator (2420) or grip (2458) of obturator (2450). Still referring to FIG. 14, cylindrical hub (2404) comprises a proximal opening (2416) and an index bezel (2430). Proximal opening (2416) is configured to receive a corresponding protrusion (2432, 2462) of obturators (2420, 2450). Although not shown, cylindrical hub (2404) may also include one or more retention features configured to secure protrusions (2432, 2462) of obturators (2420, 2450) to cylindrical hub (2404). Yet in other examples, cylindrical hub (2404) may include any other feature or features configured to selectively attach cylindrical hub (2404) to grips (2428, 2458).

As described above, targeting set (2400) comprises two obturators (2420, 2450) for use during different stages of a biopsy procedure. In particular, targeting set (2400) comprises a generally hollow obturator (2420) and a generally solid obturator (2450). Hollow obturator (2420) comprises a shaft (2422) extending distally from grip (2428). Shaft (2422) is longitudinally sized such that a blunt tip (2424) and a lateral aperture (2426) positioned on the distal end of obturator (2420) extends out of opening (2408) of cannula (2402). Shaft (2422) is sized such that edge (2412) of cannula (2402) terminates proximally relative to lateral aperture (2426) of obturator (2420). Because shaft (2406) of cannula (2402) is relatively thin, the interface between shaft (2422) of obturator (2420) and edge (2412) of cannula (2402) may create a streamlined profile. In the present example, shaft (2422) is comprised of an MRI imagable material such as plastic. Of course, other suitable materials will be apparent to those of ordinary skill in the art in view of the teachings herein.

Grip (2428) comprises a rubber grip plug (2432), which may be selectively removable from grip (2428). It should be understood that in some examples index bezel (2430) is associated with grip (2428), instead of cylindrical hub (2404). Grip (2428) extends proximally from shaft (2422), terminating at a proximal opening (2436), which may be used as a passage for the insertion of marker delivery devices, and/or other instruments associated with a biopsy procedure. Rubber grip plug (2432) is insertable over at least a portion of grip (2428) to close proximal opening (2436) when proximal opening (2436) is not in use.

Figure 14:
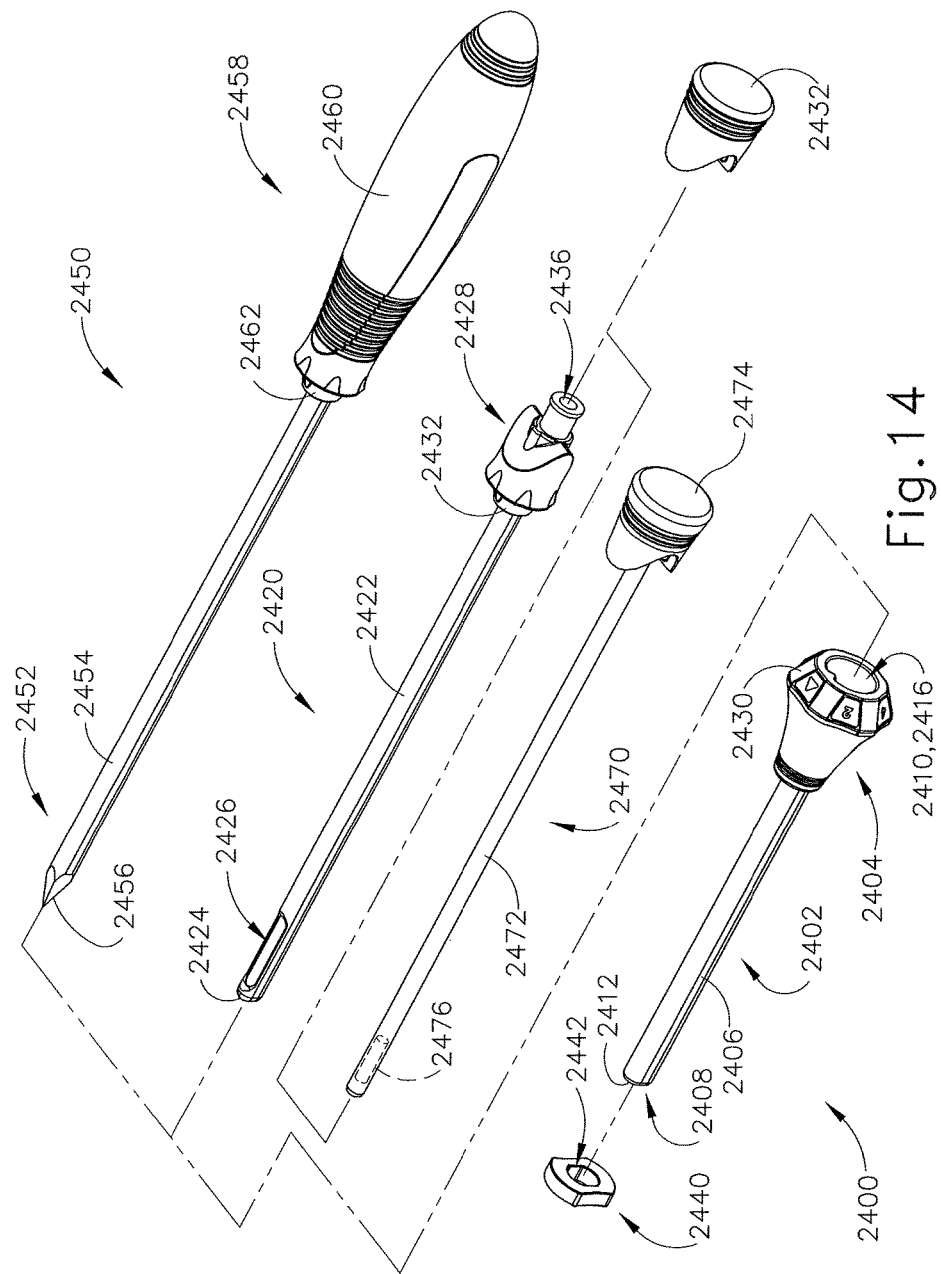
FIG. 14 depicts a perspective exploded view of another exemplary targeting set for use with the biopsy system of FIG. 1.

FIG. 14 also shows an imaging rod (2470), which may be used in place of rubber grip plug (2432). In particular, imaging rod (2470) comprises an imaging shaft (2472) and a rubber grip plug (2474). Imaging shaft (2472) is sized to be insertable into obturator (2420) and includes an MRI imagable material (2476) (shown in phantom). Although imagable material (2476) is shown as being located in the distal end of imaging shaft (2472), it should be understood that in some examples imagable material (2476) may extend through the entire length of imaging shaft (2472) or may be otherwise oriented within imaging shaft (2472). As will be described in greater detail below, imaging rod (2470) is insertable into obturator (2420) through proximal opening (2436) to enhance the contrast of targeting set (2400) when being imaged using MRI. Rubber grip plug (2474) is similar to rubber grip plug (2432), described above. In particular, rubber grip plug (2432) is insertable over at least a portion of grip (2428) to close proximal opening (2436) of obturator (2420) while supporting imaging shaft (2472).

Solid obturator (2450) comprises a solid spike portion (2452) extending distally from a grip (2458). Spike portion (2452) comprises an elongate shaft (2454) and a tissue piercing distal tip (2456). In the present example, tissue piercing tip (2456) has a plurality of facets. In addition or in the alternative, tissue piercing tip (2456) may comprise one or more blades. Shaft (2454) has a length that is configured such that tissue piercing tip (2456) protrudes through opening (2408) of cannula (2402) when solid obturator (2450) is inserted into cannula (2402). Although spike portion (2452) is described herein as being solid, it should be understood that spike portion (2452) need not necessarily be completely solid. For instance, spike portion (2452) may include a lumen, pores, openings, and/or any other similar features as will be apparent to those of ordinary skill in the art in view of the teachings herein.

Grip (2458) comprises an elongate handle (2460) and a distal attachment protrusion (2462). Handle (2460) is configured to permit a user to grasp handle (2460) such that obturator (2450) may be manually positioned and inserted into a patient. Attachment protrusion (2462) is configured to mate with opening (2416) in cylindrical hub (2404) of cannula (2402). Like with obturator (2420) described above, obturator (2450) may also include retaining members or features to secure obturator (2450) to cannula (2402).

Figure 15:
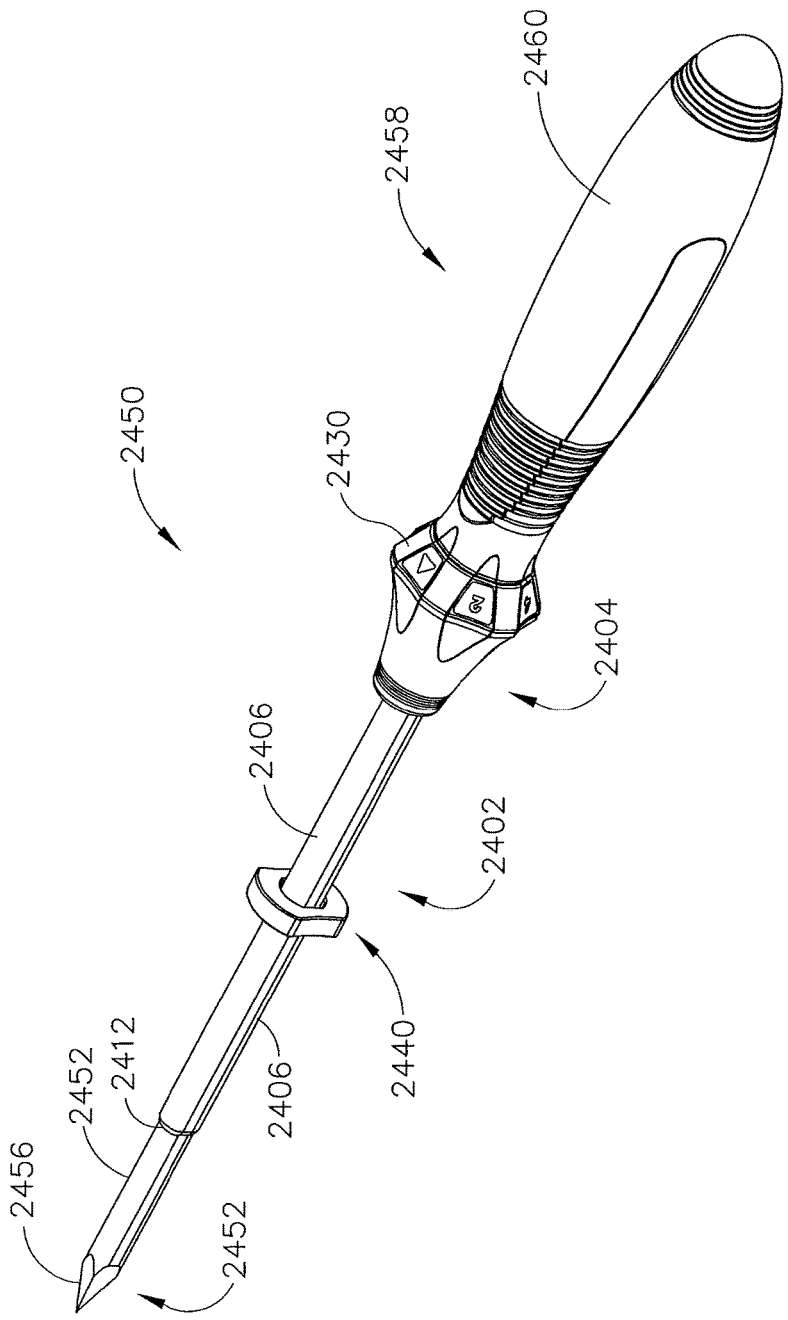
FIG. 15 depicts a perspective view of the targeting set of FIG. 14 with a piercing rod inserted into a cannula.
Figure 16:
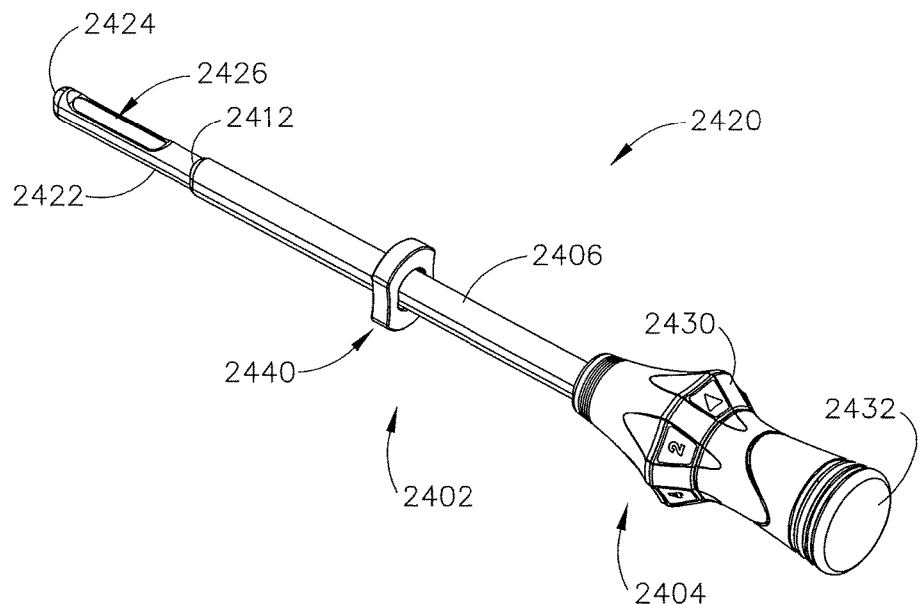
FIG. 16 depicts a perspective view of the cannula of FIG. 15 with an obturator inserted into the cannula and a depth stop device disposed on the cannula.
Figure 17:
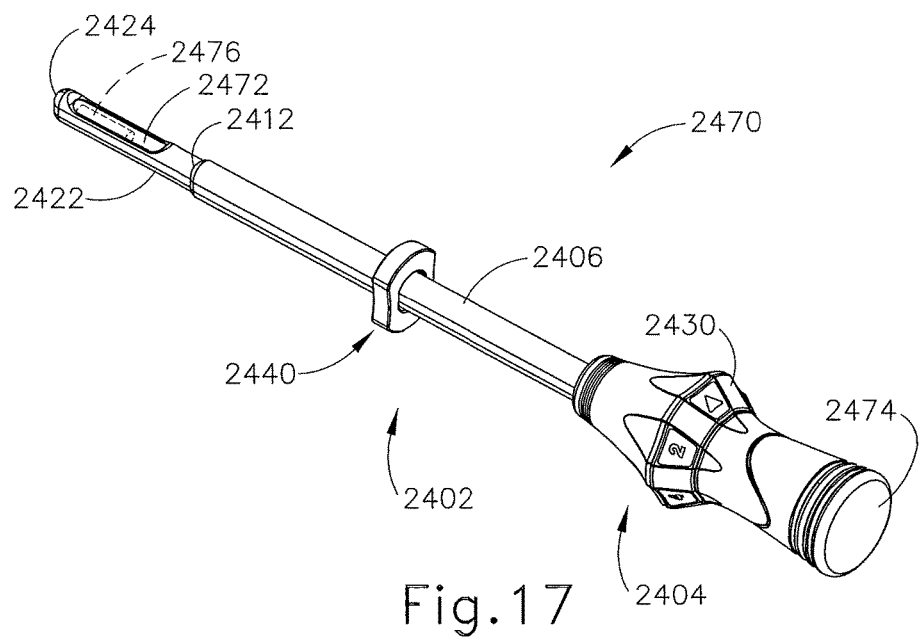
FIG. 17 depicts a perspective view of the cannula of FIG. 15 and the obturator of FIG. 16, with an imaging rod inserted through the obturator.

As can best be seen in FIGS. 15-17, targeting set (2400) includes a depth stop device (2440). Depth stop device (2440) may be positioned on cannula (2402) or obturator (2420, 2450) to prevent over insertion into a patient's breast. In the present example depth stop device (2440) includes an opening (2442) that may be sized to similarly to shaft (2406) of cannula (2402). In particular, depth stop device (2440) may be comprised of an elastomeric material such that opening (2442) may be slightly undersized relative to shaft (2406) of cannula (2402). Accordingly, depth stop device (2440) may be positioned at a certain spot on cannula (2402) where it may remain by the force of friction generated by the interference between the size of opening (2442) of depth stop device (2440) and the size of shaft (2406) of cannula (2402). In some versions, opening (2442) includes obliquely oriented elastomeric webbing that grips the outer surface of cannula (2402) when depth stop device (2440) is rotated relative to cannula (2402). In some other versions, opening (2442) includes obliquely oriented rigid fins that dig into the material of cannula (2402) when depth stop device (2440) is rotated relative to cannula (2402), thereby substantially securing the axial position of depth stop device (2440) on cannula (2402). In addition to or as an alternative to the foregoing, depth stop device (2440) may be constructed and operable in accordance with at least some of the teachings of U.S. Pat. No. 7,507,210, entitled "Biopsy Cannula Adjustable Depth Stop," issued Mar. 24, 2009, the disclosure of which is incorporated by reference herein and/or U.S. patent application Ser. No. 14/335,051, entitled "Biopsy Device Targeting Features," filed Jul. 18, 2014, the disclosure of which is incorporated by reference herein. Other suitable forms that depth stop device (2440) may take will be apparent to those of ordinary skill in the art in view of the teachings herein.

In an exemplary mode of operation, solid obturator (2450) may first be used to penetrate tissue. In particular, as can be seen in FIG. 15, solid obturator (2450) is first inserted into cannula (2402). Tissue piercing tip (2456) of solid obturator (2450) protrudes through opening (2408) in cannula (2402) such that solid obturator (2450) along with cannula (2402) may be used to pierce the breast of a patient.

Solid obturator (2450) may then be removed from cannula (2402) leaving cannula (2402) inserted in the patient. Because cannula (2402) is generally comprised of a flexible material, cannula (2402) may collapse upon itself without the presence of solid obturator (2450). Such collapsing of cannula (2402) may at least partially seal cannula (2402) relative to the patient. Of course, in examples where cannula (2402) is rigid, semi-rigid, or malleable, cannula (2402) may remain open such that no sealing effect occurs. With solid obturator (2450) removed, a user may then insert hollow obturator (2420) into cannula (2402) as is shown in FIG. 16. Blunt end (2424) of hollow obturator (2420) may expand cannula (2402) from its collapsed state without damaging cannula (2402).

As can be seen in FIG. 17, once hollow obturator (2420) is inserted into cannula (2402), imaging rod (2470) may be inserted into hollow obturator (2420) and the breast may be imaged. Alternatively, imaging rod (2470) may be inserted into the breast of a patient in conjunction with hollow obturator (2420). Inserting hollow obturator (2420) into the breast of a patient with imaging rod (2470) may be desirable because imaging rod (2470) may seal lateral aperture (2426) of hollow obturator (2420) during insertion. Once imaging is completed, imaging rod (2470) may be removed. With imaging rod (2470) removed, hollow obturator (2420) may be used with biopsy system (10) to perform a variety of tasks such as deploying a biopsy marker, aiding in MRI visualization, irrigating the biopsy site, and/or any other task as will be apparent to those of ordinary skill in the art in view of the teachings herein. Alternatively, once solid obturator (2450) is removed from cannula (2402), needle (90) of biopsy device (14) may be inserted into cannula (2402). It should therefore be understood that hollow obturator (2420) is merely optional and need not necessarily be used or provided.

C. Exemplary Targeting Set with Detachable Handle

FIGS. 18-23 show still another exemplary alternative targeting set (2500) that may be used with the biopsy system (10) described above. Targeting set (2500) is similar to targeting sets (89, 2400) described above, except as otherwise noted herein. For instance, targeting set (2500) comprises a cannula (2502) that is configured to receive obturator (2520) and the combination is configured to be guided through a guide cube (e.g., guide cube (104), etc.) to a biopsy site within a patient's breast. Additionally, an imaging rod (2570) may be used in conjunction with obturator (2520) to enhance MRI imaging of a biopsy site. Cannula (2502) includes a hollow shaft (2506) that is proximally attached to a cylindrical hub (2504) and has an opening (2508) positioned on the distal end of cannula (2502). Shaft (2506) defines a lumen (2510) extending through cannula (2502) from the proximal end to the distal end of cannula (2502). Shaft (2506) is shaped correspondingly to obturator (2520) such that obturator (2520) may be inserted through lumen (2510). Unlike opening (2508) of cannula (2402), opening (2508) of cannula (2502) comprises a beveled edge (2512), which extends from an exterior surface of cannula (2502). Although edge (2512) is shown as having a bevel that extends inwardly, it should be understood that edge (2512) may be otherwise beveled or flat similar to edge (2412) described above. Of course, edge (2512) may take on any other geometry as will be apparent to those of ordinary skill in the art in view of the teachings herein.

Cannula (2502) of the present example is substantially transparent, unlike cannula (2402) described above. Of course such a feature is merely optional and in other examples cannula (2502) may be opaque, partially transparent, translucent, and/or have any other suitable optical transmissivity. Cannula (2502) is generally comprised of a rigid material such that the form of cannula (2502) may be maintained even without obturator (2520) inserted therethrough. Of course, in other versions, cannula (2502) may be flexible, semi-rigid, or malleable.

Cylindrical hub (2504) is configured to receive a grip (2528) of obturator (2520). As can be seen in FIG. 16, cylindrical hub (2504) comprises a proximal opening (2516) and a pair of retention features (2518). Proximal opening (2516) is configured to receive a corresponding protrusion (not shown) of obturator (2520). Likewise, retention features (2518) are configured to receive corresponding retention features (not shown) of obturator (2520). In some versions, cylindrical hub (2504) includes a wiper seal, a duckbill seal, and/or one or more other kinds of sealing features that substantially prevent proximal backflow of blood and/or other bodily fluids out through proximal opening (2516) when obturator (2520) is removed from cannula (2502) while cannula (2502) is disposed in a patient's breast. By way of example only, hub (2504) may include one or more sealing features that is/are configured and operable in accordance with at least some of the teachings of U.S. Pat. No. 7,693,567, entitled "MRI Biopsy Apparatus Incorporating a Sleeve and Multi-Function Obturator," issued Apr. 6, 2010, the disclosure of which is incorporated by reference herein. Other suitable features that may be incorporated into hub (2504) will be apparent to those of ordinary skill in the art in view of the teachings herein.

Obturator (2520) comprises a shaft (2522) extending distally from grip (2528). Shaft (2522) longitudinally sized such that a piercing tip (2524) and a lateral aperture (2526) positioned on the distal end of obturator (2520) extends out of opening (2508) of cannula (2502). In particular, shaft (2522) is sized such that edge (2512) of cannula (2502) terminates proximally relative to lateral aperture (2526) of obturator (2520). Beveled edge (2512) may provide a relatively smooth transition from the outer surface of obturator (2520) to the outer surface of cannula (2502) as targeting set (2500) is inserted into tissue. Such a configuration creates a more streamlined profile which may reduce the force required to insert cannula (2502) and obturator (2520) into a patient's breast. Such an angular transition may also reduce the force required to rotate cannula (2502) and obturator (2520) in a patient's breast.

Grip (2528) comprises an index bezel (2530), a rubber grip plug (2532), and retention features (not shown). The retention features comprise distally extending tabs that are configured to snap into retention features (2518) to provide a releasable coupling between grip (2528) and hub (2504). Index bezel (2530) includes indicia (2534) which may indicate to a user the clock position of a biopsy device relative to a patient's breast. Index bezel (2530) extends proximally from indicia (2534), terminating at a proximal opening (2536), which may be used as a passage for the insertion of marker delivery devices, MR imagable material, and/or other instruments/materials associated with a biopsy procedure. Rubber grip plug (2532) is insertable over at least a portion of index bezel (2530) to close proximal opening (2536) when proximal opening (2536) is not in use.

Grip (2528) may also optionally receive a handle (2558). Similar to rubber grip plug (2532), handle (2558) may close proximal opening (2536) when proximal opening (2536) is not in use. Additionally, handle (2558) may generally provide the functionality of permitting grip (2528) to be gripped using the whole hand of an operator. Handle (2558) comprises a handle portion (2560) and an attachment portion (2562). Handle portion (2560) is shaped to complement the hand of a user. Attachment portion (2562) comprises two distally extending attachment tabs (2564). Attachment tabs (2564) are configured to engage corresponding attachment holes (2537) on the proximal end of grip (2528). Thus, attachment portion (2562) is operable to selectively secure handle (2558) to the proximal end of grip (2528).

Figure 18:
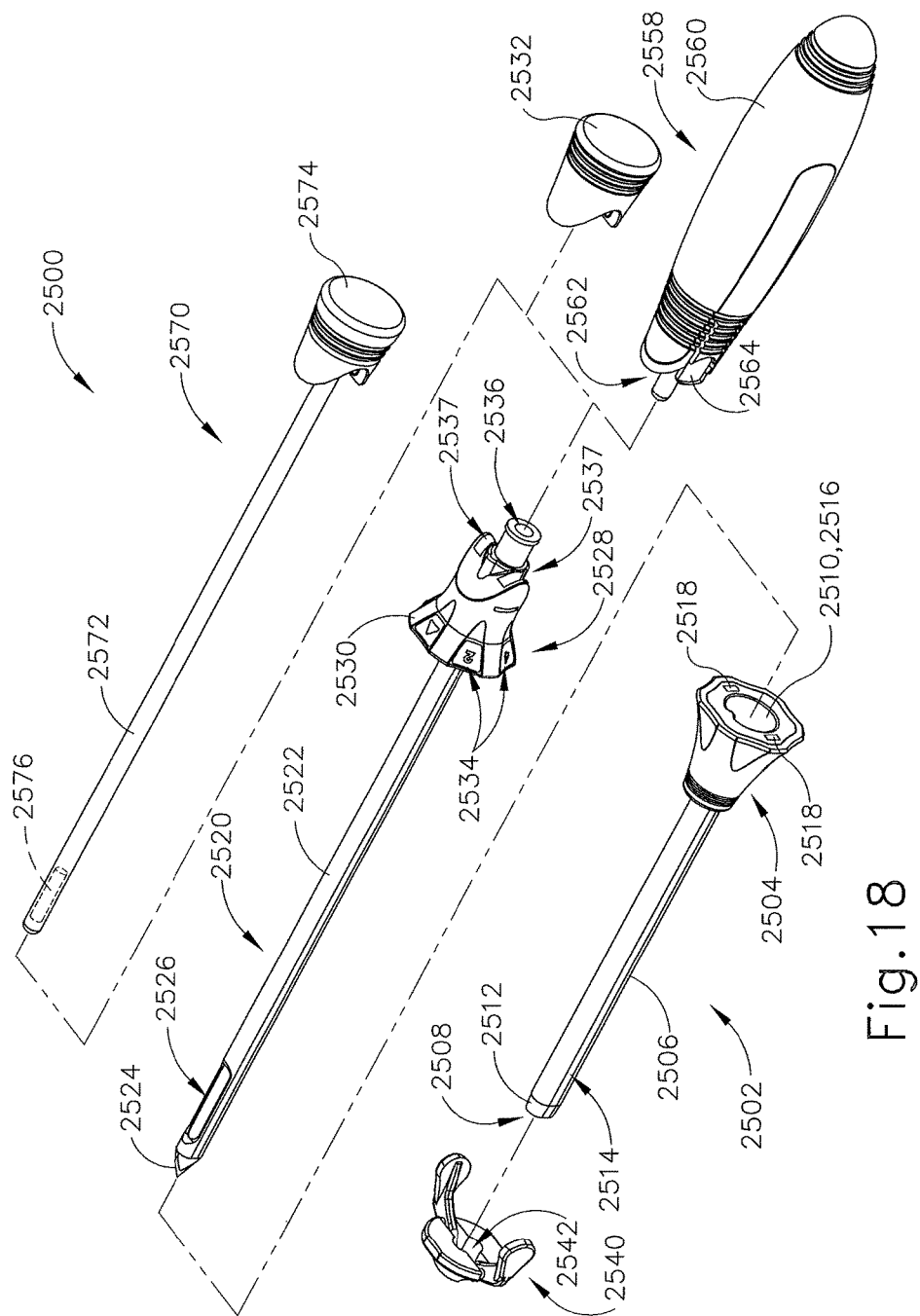
FIG. 18 depicts an exploded perspective view of an exemplary alternative targeting set for use with the biopsy system of FIG. 1.

Grip (2528) may also receive imaging rod (2570) in lieu of rubber grip plug (2532). Imaging rod (2570) may similarly close proximal opening (2536) when proximal opening (2536) is not in use. Additionally, imaging rod (2570) may provide the additional functionally of enhancing the contrast of targeting set (2500) when targeting set (2500) is visualized using MRI. As can be seen in FIG. 18, imaging rod (2570) comprises an imaging shaft (2572) and a rubber grip plug (2574). Imaging shaft (2572) is sized to be insertable into obturator (2520) and includes an MRI imagable material (2576) (shown in phantom). Although imagable material (2576) is shown as being located in the distal end of imaging shaft (2572), it should be understood that in some examples imagable material (2576) may extend through the entire length of imaging shaft (2572) or may be otherwise oriented within imaging shaft (2572). As will be described in greater detail below, imaging rod (2570) is insertable into obturator (2520) through proximal opening (2536) to enhance the contrast of targeting set (2500) when being imaged using MRI. Rubber grip plug (2574) is similar to rubber grip plug (2532), described above. In particular, rubber grip plug (2532) is insertable over at least a portion of grip (2528) to close proximal opening (2536) of obturator (2520) while supporting imaging shaft (2572).

Figure 19:
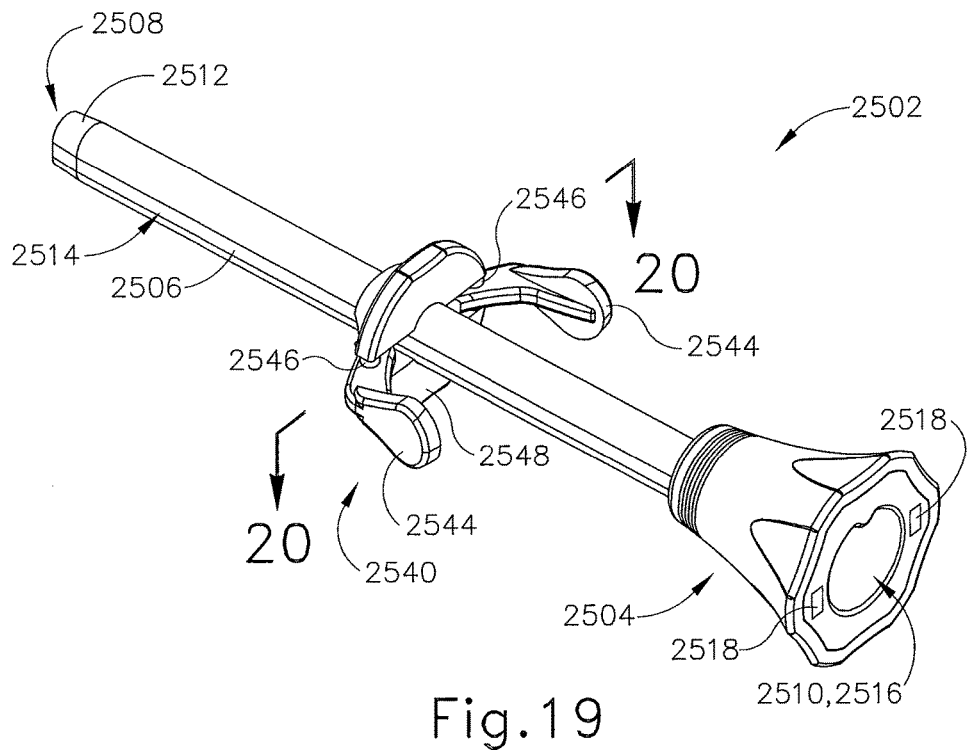
FIG. 19 depicts an enlarged perspective view of a cannula of the targeting set of FIG. 18 with a depth stop device disposed on the cannula.
Figure 20:
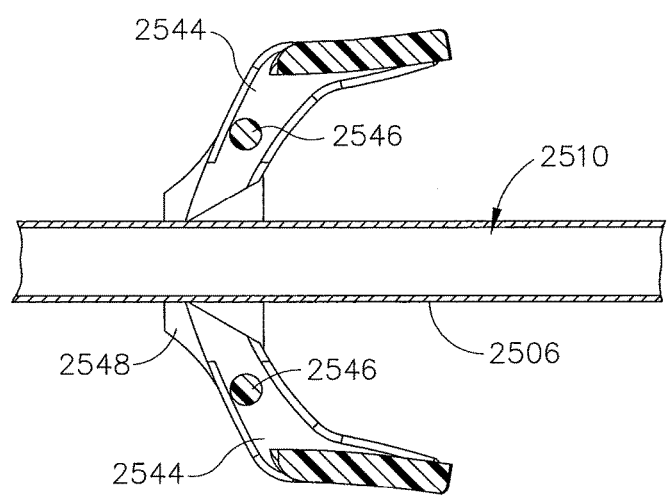
FIG. 20 depicts a top cross-sectional view of the cannula of FIG. 18, with the cross-section taken along line 20-20 of FIG. 19.

As can best be seen in FIGS. 19-20, targeting set (2500) may include a depth stop device (2540), which may be similar to depth stop device (2440) described above. For instance, depth stop device (2540) may be positioned on cannula (2502) or obturator (2520) to prevent over insertion into a patient's breast. In the present example depth stop device (2540) includes an opening (2542), which may be sized to similarly to shaft (2506) of cannula (2502). Depth stop device (2440) additionally includes two resiliently biased arms (2544), which extend proximally relative to depth stop device (2440). Arms (2544) are of integral construction with attachment members (2546) of depth stop device (2440). Attachment members (2546) are integral with a body portion (2548) of depth stop device (2540). Depth stop device (2540) may be comprised of a semi-flexible material such that arms (2544) may be flexed relative to body portion (2546) to pivot arms (2544).

As can best be seen in FIG. 20, a gripping portion (2545) of each arm (2544) extends into opening (2542) on either side of depth stop device (2540). Gripping portions (2545) are configured to dig into or frictionally bear against shaft (2506) of cannula (2502). In particular, when arms (2544) are in a relaxed state, arms (2544) are resiliently biased toward cannula (2506) such that gripping portions (2545) may dig into or at least bear against shaft (2506) of cannula (2506), thereby securing the axial position of depth stop device (2540) on cannula (2502). Because depth stop device (2540) is comprised of a semi-flexible material, a user may grasp arms (2544) and pivot them away from cannula (2502) such that gripping portions (2545) disengage from cannula (2502). Thus, depth stop device (2540) is operable to be positioned and re-positioned axially on cannula (2506) by squeezing and releasing arms (2544). It should be understood that because arms (2544) extend proximally relative to depth stop device (2540), depth stop device (2540) may be readily adjusted even while depth stop device (2540) is positioned adjacent to a guide cube, as will be described in greater detail below. Such a feature may be desirable if, by way of example only, a user has reason to adjust the depth setting on cannula (2502) while cannula (2502) is positioned within the breast of a patient. In addition to or as an alternative to the foregoing, depth stop device (2540) may be constructed and operable in accordance with at least some of the teachings of U.S. Pat. No. 7,507,210, entitled "Biopsy Cannula Adjustable Depth Stop," issued Mar. 24, 2009, the disclosure of which is incorporated by reference herein and/or U.S. patent application Ser. No. 14/335,051, entitled "Biopsy Device Targeting Features," filed Jul. 18, 2014, the disclosure of which is incorporated by reference herein.

Other suitable forms that depth stop device (2540) may take will be apparent to those of ordinary skill in the art in view of the teachings herein.

Figure 21:
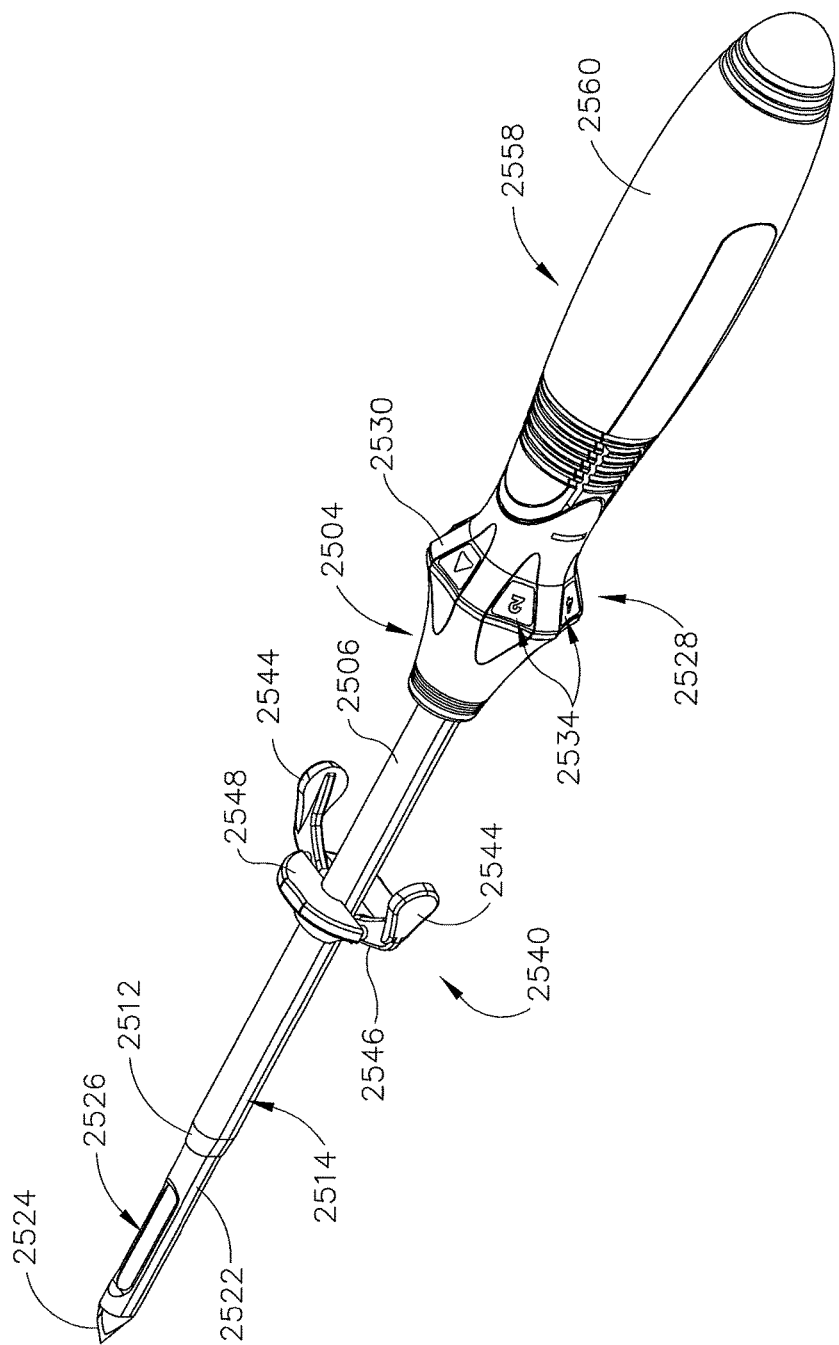
FIG. 21 depicts a perspective view of a cannula of FIG. 18 with an obturator inserted therethough, the obturator equipped with an optional handle.

In an exemplary mode of operation, obturator (2520) may first be used to penetrate tissue. In particular, as can be seen in FIG. 21, obturator (2520) is first inserted into cannula (2502). Tissue piercing tip (2524) of obturator (2520) protrudes through opening (2508) in cannula (2502) such that obturator (2520) along with cannula (2502) may be used to pierce the breast of a patient. Optionally, handle (2558) may be attached to the proximal end of obturator (2520) to assist a user with positioning obturator (2520).

If handle (2558) is used, handle (2558) may be removed from obturator (2520) once obturator (2520) and cannula (2502) have been positioned in the breast. Similarly, if rubber grip plug (2532) is used, rubber grip plug (2532) may be removed from obturator (2520). Thus, obturator (2520) and cannula (2502) may remain inserted in the patient with obturator (2520) and cannula (2502) in the configuration shown in FIG. 22. With handle (2558) or rubber grip plug (2532) removed, a user may then insert imaging rod (2570) into obturator (2520) and the breast may be imaged. Alternatively, imaging rod (2570) may be inserted into the breast of a patient in conjunction with obturator (2520) and cannula (2502). Inserting obturator (2520) and cannula (2502) into the breast of a patient with imaging rod (2570) may be desirable because imaging rod (2570) may seal lateral aperture (2526) of obturator (2520) during insertion. Once imaging is completed, imaging rod (2570) may be removed. With imaging rod (2570) removed, obturator (2520) may be used with biopsy system (10) to perform a variety of tasks such as deploying a biopsy marker, aiding in MRI visualization, irrigating the biopsy site, and/or any other task as will be apparent to those of ordinary skill in the art in view of the teachings herein. Alternatively, once solid obturator (2550) is removed from cannula (2502), needle (90) of biopsy device (14) may be inserted into cannula (2502). It should therefore be understood that obturator (2520) is merely optional and need not necessarily be used or provided.

D. Exemplary Targeting Set with Enlarged Cannula

Figure 24:
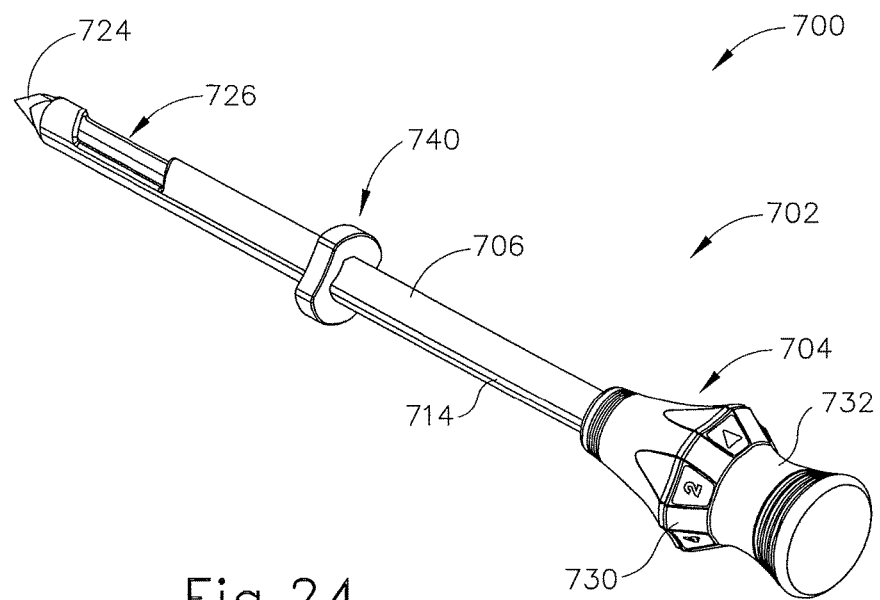
FIG. 24 depicts a perspective view of still another exemplary alternative targeting set for use with the biopsy system of FIG. 1.
Figure 25:
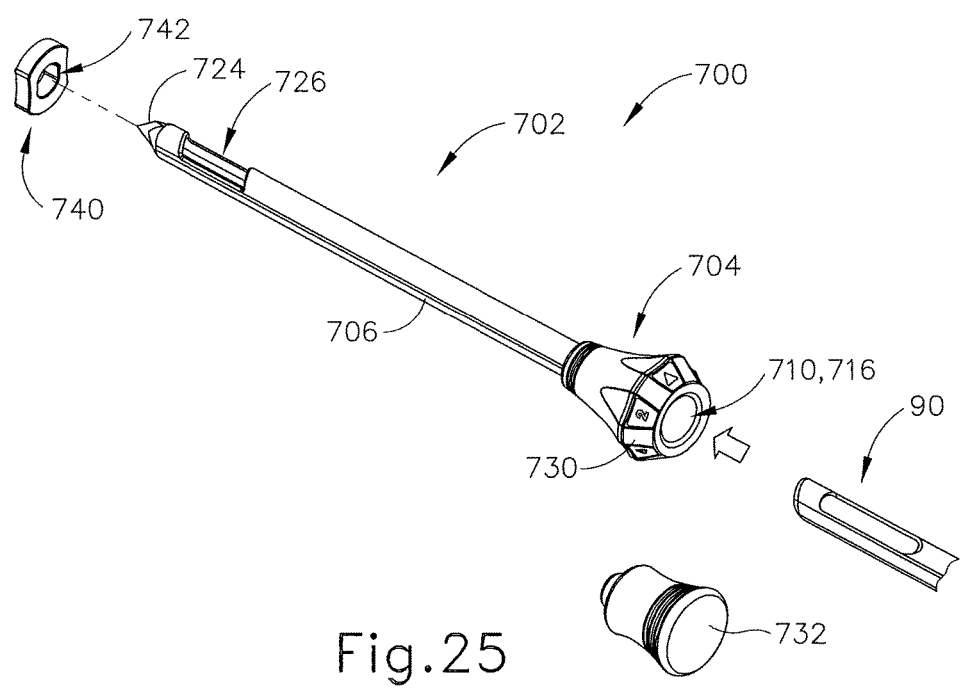
FIG. 25 depicts an exploded perspective view of the targeting set of FIG. 24.
Figure 26:
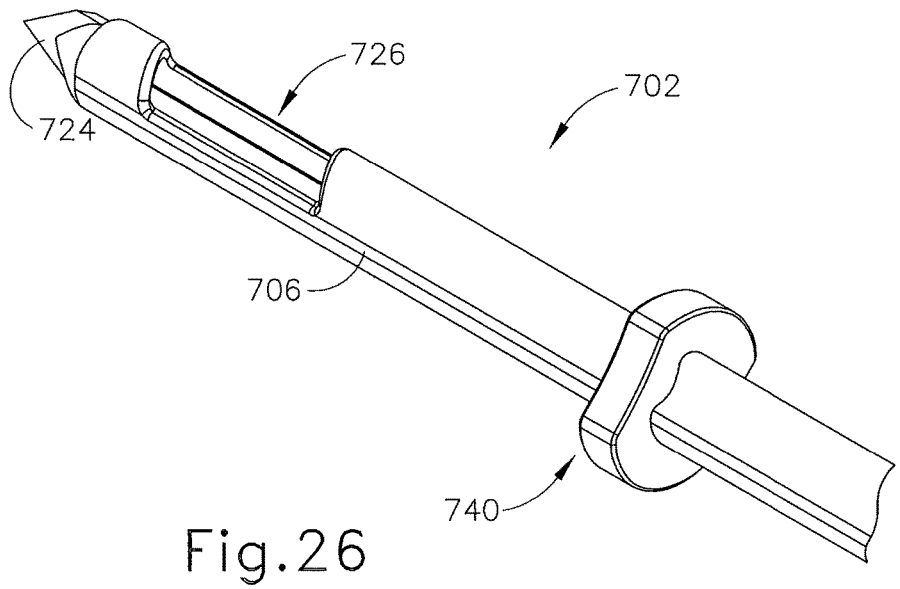
FIG. 26 depicts an a detailed perspective view of the targeting set of FIG. 24, with a biopsy needle inserted into a cannula of the targeting set.
Figure 27:
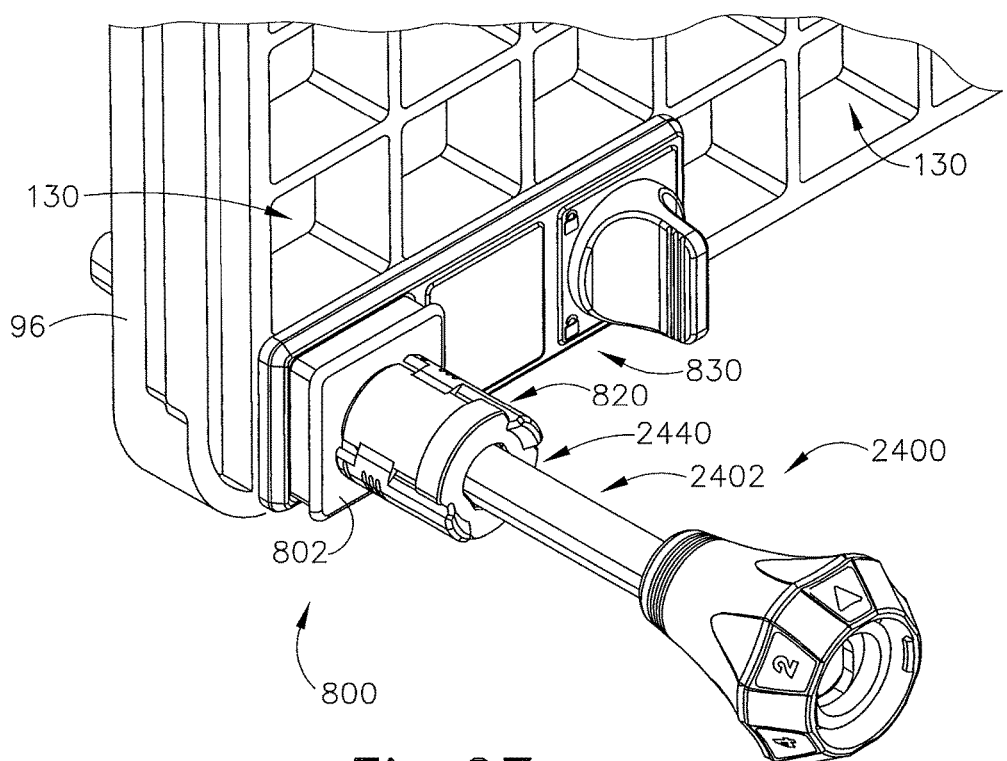
FIG. 27 depicts a perspective view of an exemplary alternative localization fixture for use with the biopsy system of FIG. 1.

FIGS. 24-26 show yet another exemplary alternative targeting set (700) that may be used with the biopsy system described above. Unlike targeting sets (89, 500, 2400, 2500) described above, targeting set (700) comprises a cannula (702) that also functions as an obturator such that cannula (702) is configured to be guided through a guide cube (e.g., guide cube (104), etc.) to a biopsy site within a patient's breast. Cannula (702) may also directly receive a blunt-tipped needle (90) of a biopsy device (14), without needing an obturator. Cannula (702) includes a hollow shaft (706) that is proximally attached to a cylindrical hub (704). Shaft (706) comprises a tissue piercing tip (724) and a lateral aperture (726) positioned on the distal end of cannula (702). Shaft (706) defines a lumen (710) extending through cannula (702) from the proximal end to the distal end of cannula (702). Shaft (706) is shaped correspondingly to needle (90) of probe (91) such that needle (90) may be inserted through lumen (710). It should be understood that in contrast to lumen (510, 2410, 2510) of cannula (502, 2402, 2502), lumen (710) is sized relatively larger to accommodate needle (90). Accordingly, shaft (706) of cannula (702) may also be correspondingly enlarged relative to shaft (506, 2406, 2506) of cannula (502, 2402, 2502). Of course, lumen (710) and shaft (706) may take on any other geometry as will be apparent to those of ordinary skill in the art in view of the teachings herein.

In the present example, cannula (702) is substantially opaque. Of course, such a feature is merely optional and in other examples cannula (702) may be fully or partially transparent or have any other suitable optical transmissivity. Cannula (702) is generally comprised of a relatively rigid MRI imagable material such that shaft (706) may maintain a consistent shape whether needle (90) is inserted into cannula (702) or not. Of course, in other versions, cannula (702) may be of varying degrees of rigidity or flexibility as will be apparent to those of ordinary skill in the art in view of the teachings herein.

Figure 22:
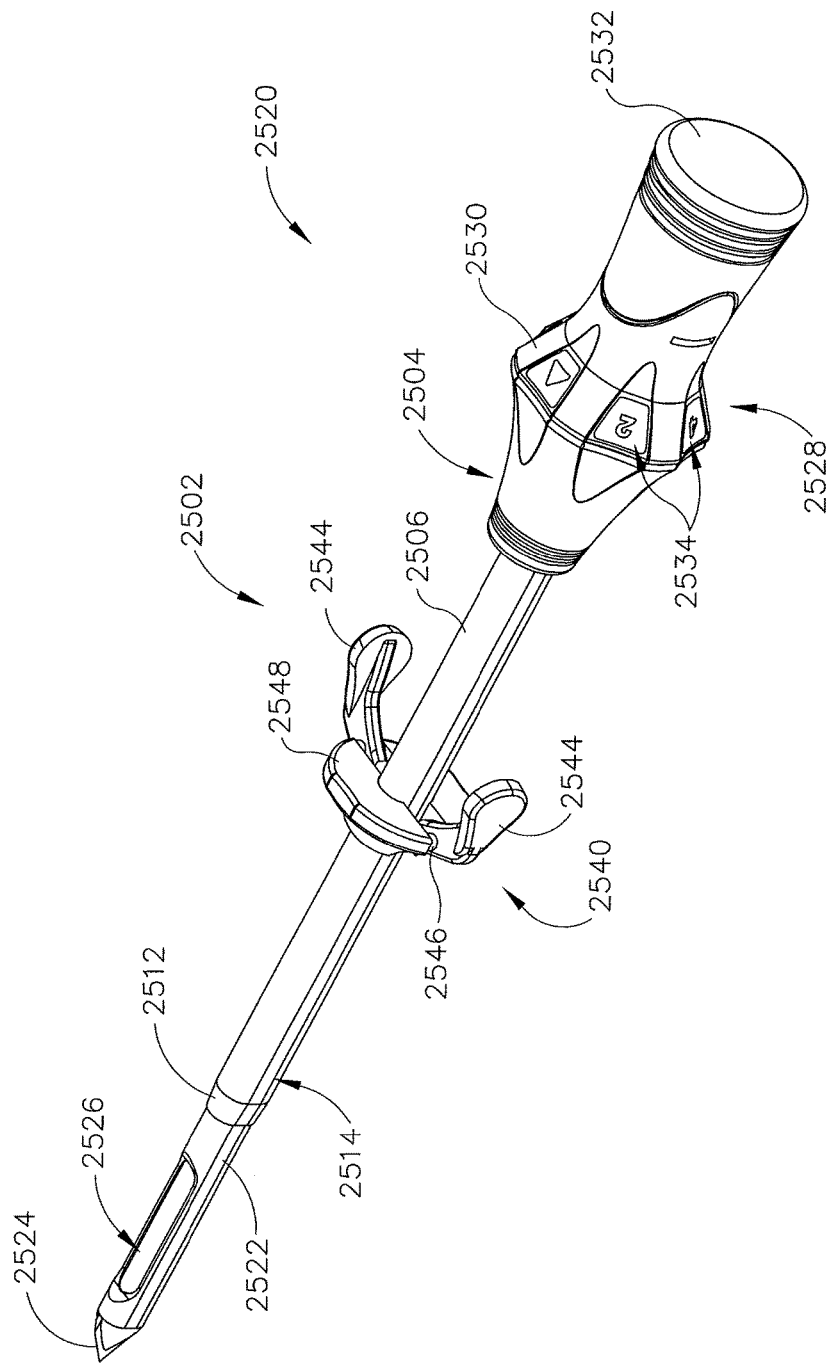
FIG. 22 depicts a perspective view of the cannula of FIG. 18 and the obturator of FIG. 19 with the obturator equipped with a rubber grip plug.
Figure 23:
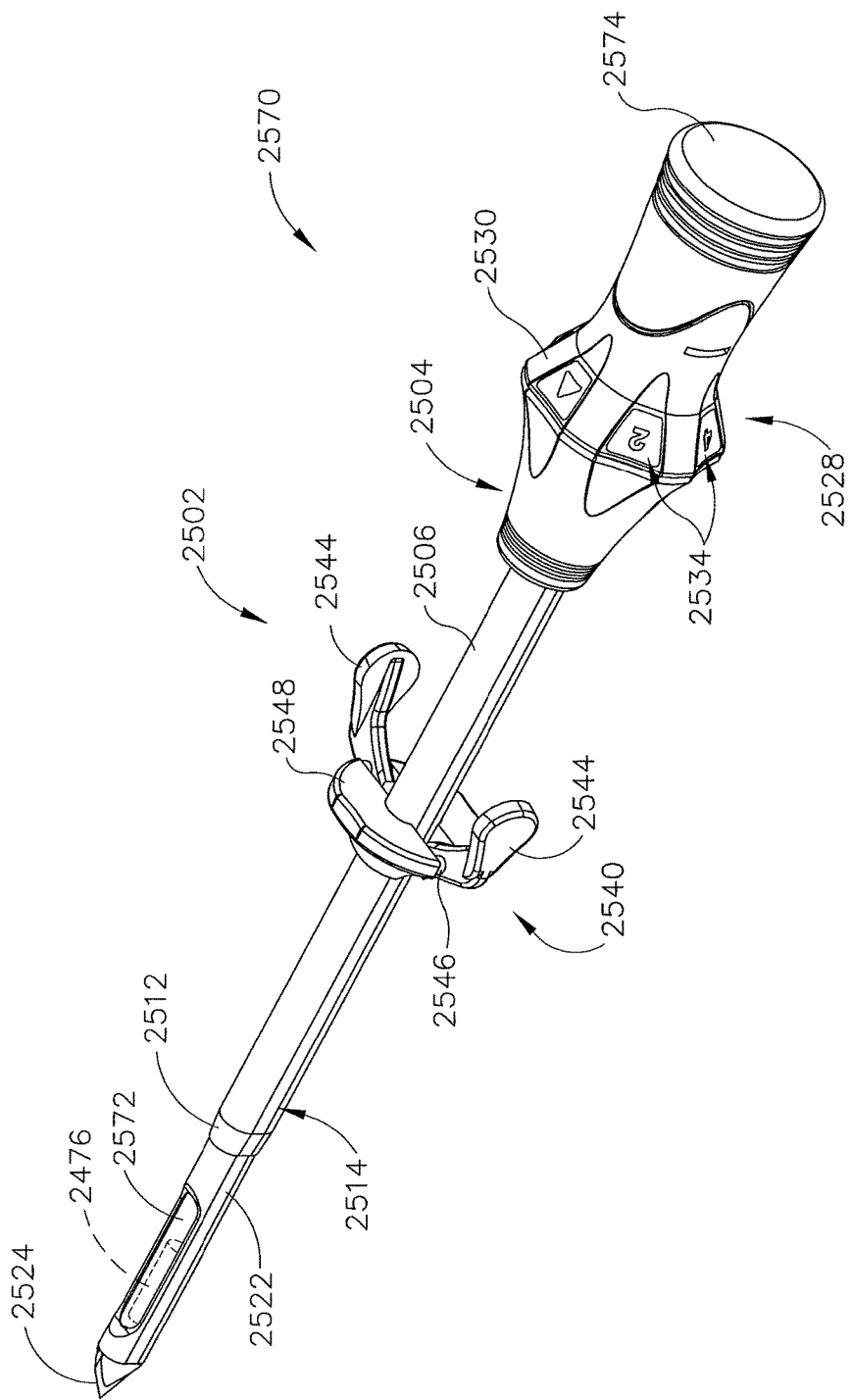
FIG. 23 depicts a perspective view of the cannula of FIG. 18 and the obturator of FIG. 19 with the obturator equipped with an imaging rod.

As is best seen in FIG. 22, cylindrical hub (704) comprises a proximal opening (716) and an index bezel (730). Proximal opening (716) is configured to receive a rubber grip plug (732), which may be removably secured in proximal opening (716). In the present example, rubber grip plug (732) acts to seal proximal opening (716) when there is no device inserted into cannula (702). Although not shown, probe (91) may include a protrusion or other feature which may also be received by proximal opening (716). Cylindrical hub (704), rubber grip plug (732), and/or probe (91) may also include one or more retention features similar to the one or more retention features described above with respect to cylindrical hub (504) described above. In other examples, cylindrical hub (704) may include any other feature configured to selectively attach cylindrical hub (704) to rubber grip plug, and/or probe (91).

As can best be seen in FIG. 26, targeting set (700) includes a depth stop device (740), which may be similar to depth stop device (95) described above. For instance, depth stop device (740) may be inserted onto cannula (702) to prevent over insertion into a patient's breast. In the present example, depth stop device (740) includes an opening (742), which may be sized to similarly to shaft (706) of cannula (702). In particular, depth stop device (740) may be comprised of an elastomeric material such that opening (742) may be slightly undersized relative to outer surface (714) of cannula (702). Accordingly, depth stop device (740) may be positioned at a certain spot on cannula (702) where it may remain by the force of friction generated by the interference between the size of opening (742) of depth stop device (740) and the size of outer surface (714) of cannula (702). In some versions, opening (742) includes obliquely oriented elastomeric webbing that grips the outer surface of cannula (702) when depth stop device (740) is rotated relative to cannula (702). In some other versions, opening (742) includes obliquely oriented rigid fins that dig into the material of cannula (702) when depth stop device (740) is rotated relative to cannula (702), thereby substantially securing the axial position of depth stop device (740) on cannula (702). In addition to or as an alternative to the foregoing, depth stop device (740) may be constructed and operable in accordance with at least some of the teachings of U.S. Pat. No. 7,507,210, entitled "Biopsy Cannula Adjustable Depth Stop," issued Mar. 24, 2009, the disclosure of which is incorporated by reference herein and/or U.S. patent application Ser. No. 14/335,051, entitled "Biopsy Device Targeting Features," filed Jul. 18, 2014, the disclosure of which is incorporated by reference herein. Other suitable forms that depth stop device (740) may take will be apparent to those of ordinary skill in the art in view of the teachings herein.

Because cannula (702) is substantially opaque, shaft (706) of cannula (702) may include depth indicia (not shown), which may be used to position depth stop device (740) at a position on cannula (702) corresponding to a desired depth. Of course, in other examples, indicia may be located on elsewhere or simply omitted all together.

In an exemplary mode of operation, solid cannula (702) is operable to both pierce tissue of a patient and introduce various biopsy devices described herein. For instance, cannula (702) may be first used with biopsy system (10) to pierce tissue. In such a mode of operation, rubber grip plug (732) may be positioned in proximal opening (716) of cylindrical hub (704). The MRI imagable material of cannula (702) allows cannula (702) to be used in conjunction with MRI to position cannula (702) relative to a biopsy site. Once cannula (702) positioned, rubber grip plug (732) may be removed from proximal opening (716) of cylindrical hub (704). Needle (90) of probe (91) or any other suitable biopsy device described herein may be then inserted into cannula (702) to perform the remainder of the biopsy procedure.

VI. Exemplary Alternative Targeting Set Guides

As a variation of localization fixture (16) discussed above, localization fixture (16) may be arranged to prevent backing-out of guide cube (104) relative to grid plate (96). Various examples of how guide cube (104) may be reconfigured to prevent backing-out of guide cube (104) will be described in greater detail below. Additionally, examples of other apparatuses associated with guide cube (104) for preventing guide cube (104) from backing out will be described in greater detail below. Other examples will be apparent to those of ordinary skill in the art according to the teachings herein. It should be understood that the guide cube examples described below may function substantially similar to guide cube (104) described above. In particular, the guide cube examples described below may be inserted into grid plate (96) and used to guide a cannula and obturator into a patient's breast; to support an inserted cannula and obturator; and to support a biopsy device. It should be understood that the guide device examples discussed below may be used with any of the biopsy devices discussed herein.

A. Exemplary Linear Targeting Set Guide Assembly

FIGS. 27-32 show an exemplary alternative targeting set guide assembly (800) that may be used in combination with grid plate (96) and any of the various targeting sets (89, 500, 2400, 2500, 700) described herein. While guide assembly (800) is shown as being used with targeting set (2400), it should be understood that guide assembly (800) may be used with any other targeting set (89, 500, 2500, 700) described herein, any of the targeting sets described in any of the references that are cited herein, and/or any other suitable kinds of targeting sets. It should also be understood that guide assembly (800) may serve as a substitute for guide cube (104). Guide assembly (800) is thus operable to guide targeting set (2400) as targeting set (2400) is inserted through grid plate (96); then support targeting set (2400) and an associated biopsy device once targeting set (2400) has fully engaged guide assembly (800).

Guide assembly (800) of the present example comprises a guide cube (802), a cube lock (820), and a grid plate adaptor (830). Generally and as will be described in greater detail below, targeting set (2400) is insertable into guide cube (802) and is secured to guide cube (802) by cube lock (820). Guide cube (802) is insertable into grid plate adaptor (830), which secures guide cube (802) along with targeting set (2400) relative to grid plate (96).

Figure 28:
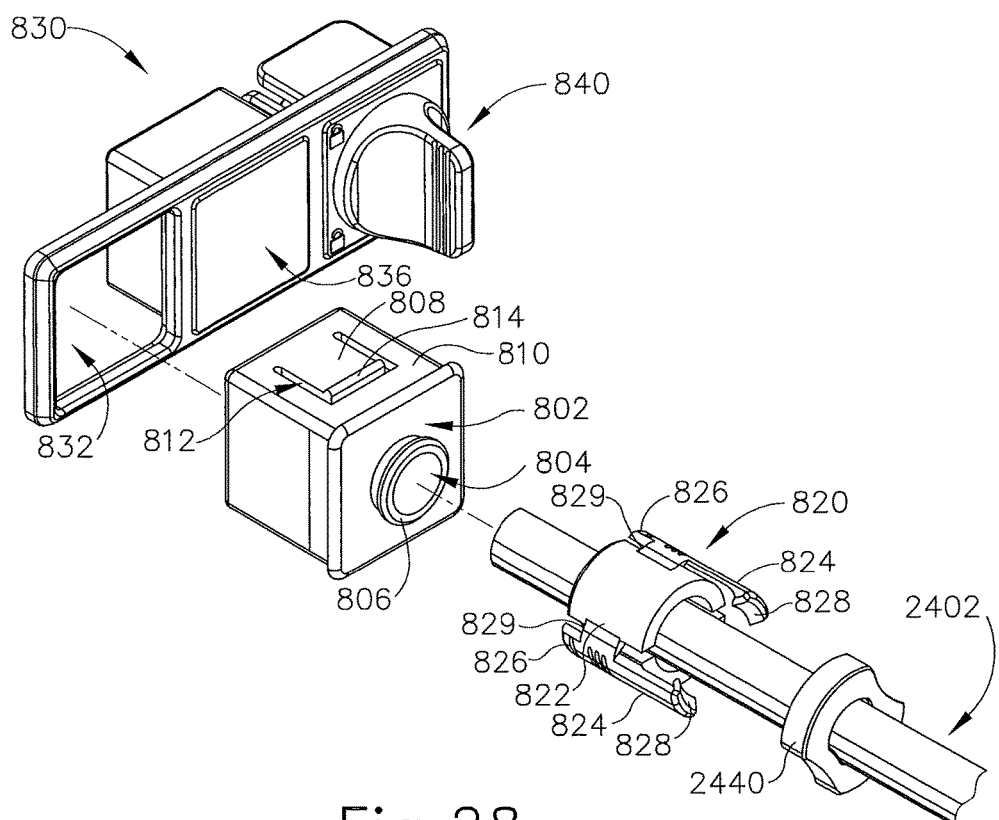
FIG. 28 depicts an exploded perspective view of the localization fixture of FIG. 27.
Figure 29:
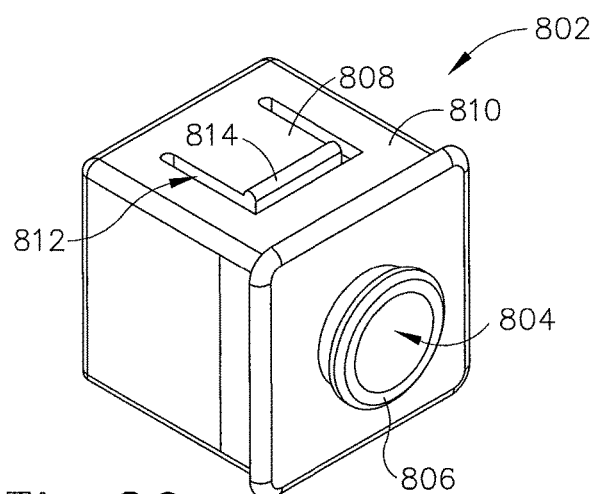
FIG. 29 depicts a perspective view of a guide block for use with the localization fixture of FIG. 27.

As can be seen in FIGS. 28 and 29, guide cube (802) has a cubic shape similar to guide cube (104). Guide cube (802) includes a central guide hole (804), which is configured to receive cannula (2402) of targeting set (2400). Guide hole (804) extends distally from the proximal face of guide cube (802) to the distal face of guide cube (802). Additionally, guide hole (804) generally extends perpendicularly relative to the proximal and distal faces of guide cube (802). Although not shown, it should be understood that guide hole (804) may be positioned in numerous alternative positions on the distal and proximal face of guide cube (802). By way of example only, in some examples guide hole (804) is offset along one or more axes from the central longitudinal axis of guide cube (802) but still aligned with the central longitudinal axis of guide cube (802). In other examples, guide hole (804) is alternatively positioned in a corner of the proximal and distal face of guide cube (802). In yet further examples, it should be understood that multiple guide cubes (802) with different guide hole (804) configurations may be usable interchangeably with guide cube (802) of the present example to achieve numerous targeting trajectories. Guide hole (804) comprises a protruding flange (806), which, as will be discussed in greater detail below, permits cube lock (820) to selectively fasten to guide cube (802).

Guide cube (802) further includes two integral tabs (808) on a top face (810) and bottom face (not shown) of guide cube (802). Integral tabs (808) are separated by a gap (812) in guide cube (802). Gap (812) permits integral tabs (808) to deflect inwardly relative to top face (810) or bottom face, respectively. A retaining protrusion (814) is positioned on the proximal end of each integral tab (808). As will be described in greater detail below, retaining protrusion (814) is operable to engage grid plate adaptor (830) to hold guide cube (802) in place when guide cube (802) is inserted into grid plate adaptor (830).

Cube lock (820) comprises cylindrical sleeve (822) which is configured to permit cannula (2402) of targeting set (2400) to slidably engage cube lock (820). Cube lock (820) further comprises two pairs of resilient arms (824, 826) extending proximally and distally from cylindrical sleeve (822). In particular, each pair of resilient arms (824, 826) extends proximally and distally, respectively before terminating in an inwardly extending protrusion (828, 829). Each protrusion (828, 829) is configured to engage a particular surface of either depth stop device (2440) or protruding flange (806). For instance, a proximally extending pair of resilient arms (824) is configured to receive depth stop device (2440) such that depth stop device (2440) is confined between cylindrical sleeve (822) and protrusion (828). Similarly, a distally extending pair of resilient arms (826) is configured to receive protruding flange (806) such that protruding flange (806) is confined between cylindrical sleeve (822) and protrusion (829). Because depth stop device (2440) is configured to maintain a fixed position relative to cannula (2402), cube lock (820) is thus operable to maintain cannula (2402) in a fixed position relative to guide cube (802).

Figure 30:
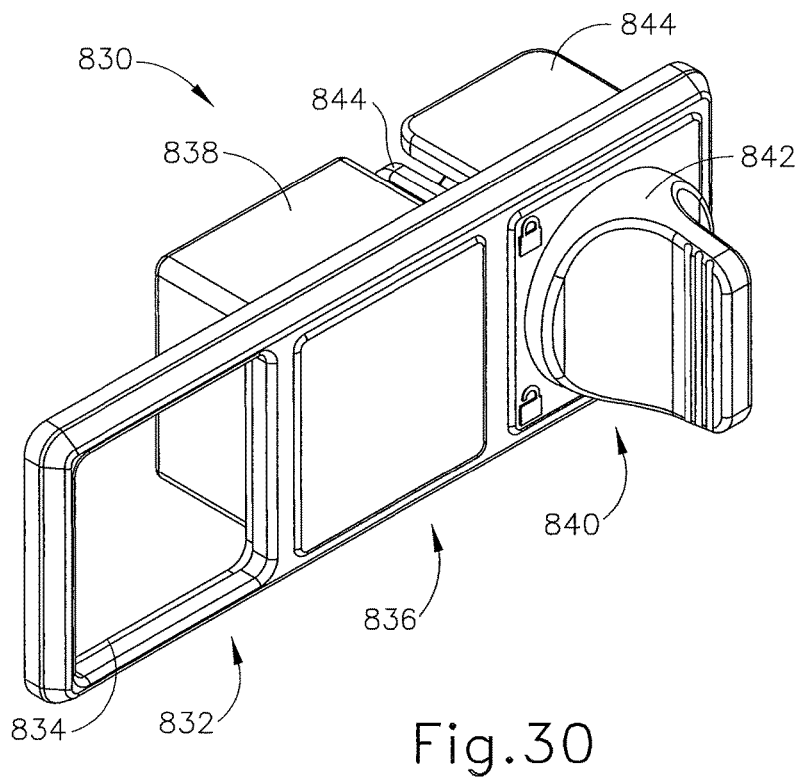
FIG. 30 depicts a perspective view of a grid plate adaptor for use with the localization fixture of FIG. 27.
Figure 31:
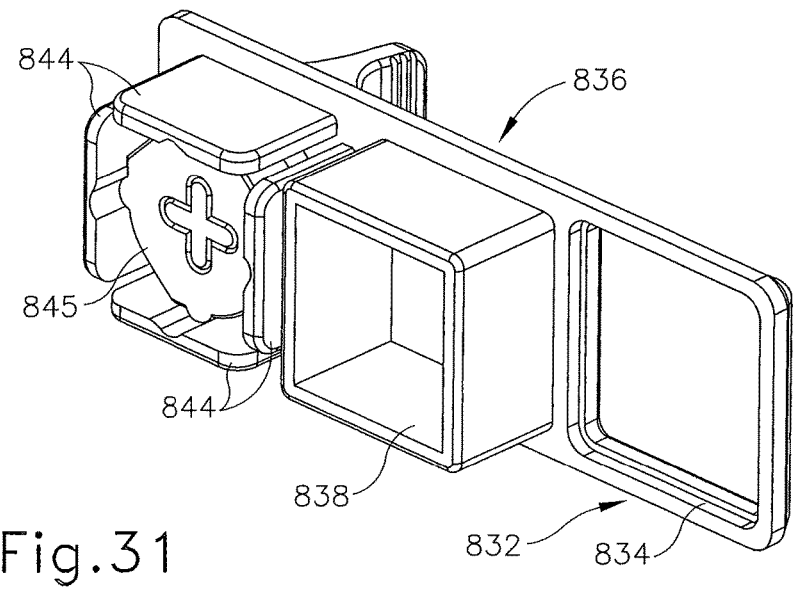
FIG. 31 depicts another perspective view of the grid plate adaptor of FIG. 30.
Figure 32:
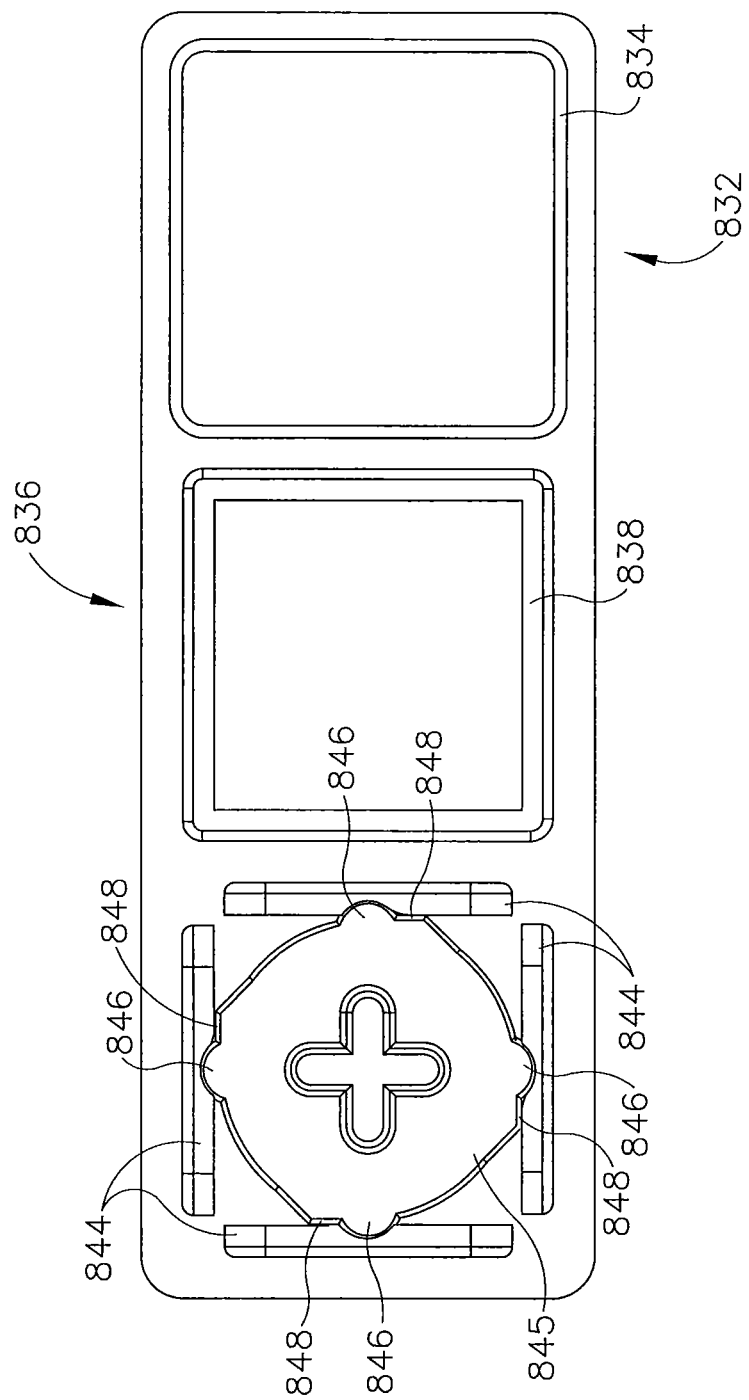
FIG. 32 depicts a back elevational view of the grid plate adaptor of FIG. 30.
Figure 33:
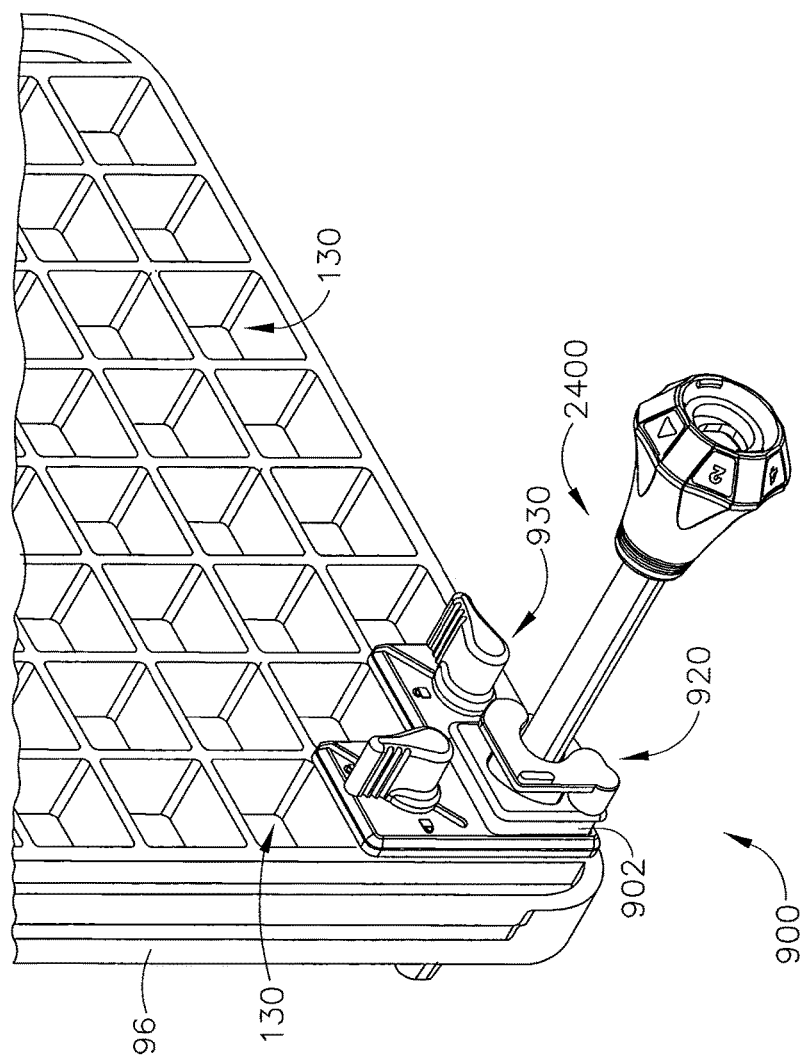
FIG. 33 depicts a perspective view of still another exemplary alternative localization fixture for use with the biopsy system of FIG. 1.

FIGS. 30-32 show detailed views grid plate adaptor (830). Grid plate adaptor (830) includes three linearly aligned features (832, 836, 840) which correspond to square recesses (130) in grid plate (96). Although the features (832, 836, 840) described herein are shown and described as being in a particular order, it should be understood that such features may be rearranged in any suitable way. Additionally, some features (832, 836, 840) may be duplicated as desired or simply omitted as will be apparent to those of ordinary skill in the art in view of the teachings herein.

The three linearly aligned features (832, 836, 840) comprise an guide cube aperture (832), an alignment feature (836), and a locking feature (840). Guide cube aperture (832) provides a space through which guide (802) cube may be inserted. Additionally, guide cube aperture (832) is defined by a ledge member (834), which provides a surface for integral tabs (808) of guide cube (802) to engage thereby preventing guide cube (802) from backing out of guide cube aperture (832).

Alignment feature (836) includes a rectangular protrusion (838), which is shaped to fit in a square recess (130) of grid plate (96). Accordingly, when grid plate adaptor (830) is inserted into grid plate (96), rectangular protrusion (838) ensures proper alignment of grid plate adaptor (830) with square recesses (130) of grid plate (96).

Locking feature (840) comprises a rotatable actuator (842), four distally extending locking members (844), and a rotatable barrel cam (845). Actuator (842) is rotatable to lock grid plate adaptor (830) into grid plate (96). Barrel cam (845) is secured to actuator (842) such that rotation of actuator (842) results in rotation of barrel cam (845). Barrel cam (845), as will be described in greater detail below, is configured to push locking members (844) outwardly. Accordingly, locking members (844) are configured to flex in response to being acted upon by barrel cam (845).

As can best be seen in FIG. 32, barrel cam (845) is generally round and comprises four cam members (846) and four adjacent flats (848). Cam members (846) protrude outwardly from barrel cam (845). Locking members (844) are correspondingly positioned adjacent to each cam member (846) such that there is an interference between cam members (846) and locking members (844) when barrel cam (845) is rotated such that cam members (846) are oriented perpendicularly relative to locking members (844). Flats (848) are configured to interface with locking members (844) such that barrel cam (845) can only rotate through a certain range of motion.

In an exemplary mode of operation, barrel cam (845) begins oriented such that cam members (846) are disengaged relative to locking members (844). Actuator (842) can then be rotated to rotate cam members (846) of barrel cam (845) into engagement with locking members (844). Once cam members (846) fully engage locking members (844), flats (848) prevent further rotation of barrel cam (845) such that a user must reverse rotation of actuator (842) to disengage cam members (846). Grid plate adaptor (830) is locked into grid plate (96) by locking members (844), which are pushed outwardly into the walls of a given square recess (130) by cam members (846). With grid plate adaptor (830) locked into place, guide cube (802) may be inserted into guide cube aperture (832) to guide targeting set (2400). Other suitable ways in which grid plate adaptor (830) may be selectively secured to grid plate (96) will be apparent to those of ordinary skill in the art in view of the teachings herein

B. Exemplary Corner Targeting Set Guide Assembly

FIGS. 33-37 show another exemplary alternative targeting set guide assembly (900) that may be used in combination with grid plate (96) and any of the various targeting sets (89, 500, 2400, 2500, 700) described herein. While guide assembly (900) is shown as being used with targeting set (2400), it should be understood that guide assembly (900) may be used with any other targeting set (89, 500, 2400, 2500, 700) described herein, any of the targeting sets described in any of the references that are cited herein, and/or any other suitable kinds of targeting sets. It should also be understood that guide assembly (900) may serve as a substitute for guide cube (104). Guide assembly (900) is thus operable to guide targeting set (2400) as targeting set (2400) is inserted through grid plate (96); then support targeting set (2400) and an associated biopsy device once targeting set (2400) has fully engaged guide assembly (900).

Guide assembly (900) of the present example comprises a guide cube (902), a cube lock (920), and a grid plate adaptor (930). Generally and as will be described in greater detail below, targeting set (2400) is insertable into guide cube (902) and is secured to guide cube (902) by cube lock (920). Guide cube (902) is insertable into grid plate adaptor (930), which secures guide cube (902) along with targeting set (2400) relative to grid plate (96).

Figure 34:
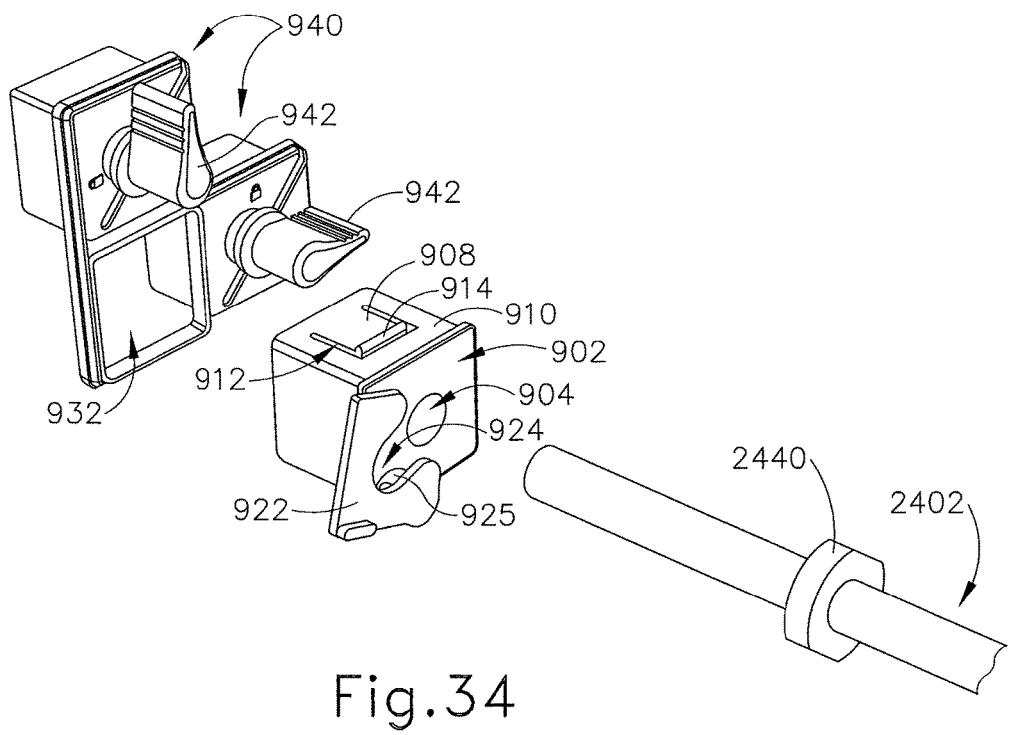
FIG. 34 depicts an exploded perspective view of the localization fixture of FIG. 33.
Figure 35:
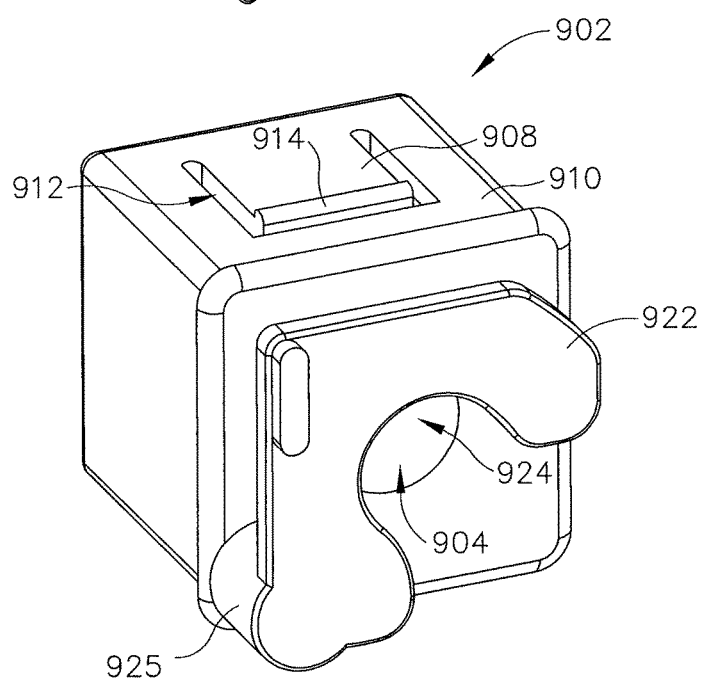
FIG. 35 depicts a perspective view of a guide block for use with the localization fixture of FIG. 33.

As can be seen in FIGS. 34 and 35, guide cube (902) has a cubic shape similar to guide cubes (104, 802). Guide cube (902) includes a central guide hole (904), which is configured to receive cannula (2402) of targeting set (2400). Guide hole (904) extends distally from the proximal face of guide cube (902) to the distal face of guide cube (902). Although guide hole (904) of the present example is shown as being centrally disposed on the proximal and distal faces of guide cube (902), it should be understood that numerous other positions may be used. For instance, in some examples guide hole (904) is laterally offset from one or more central axes of proximal and distal faces of guide cube (902). In other examples, guide hole (904) is disposed in a corner of the proximal and distal faces of guide cube (902). In still other examples, any other suitable positioning is used as will be apparent to those of ordinary skill in the art in view of the teachings herein.

Guide cube (902) further includes two integral tabs (908) on a top face (910) and bottom face (not shown) of guide cube (902). Integral tabs (908) are separated by a gap (912) in guide cube (902). Gap (912) permits integral tabs (908) to deflect inwardly relative to top face (910) or bottom face, respectively. A retaining protrusion (914) is positioned on the proximal end of each integral tab (908). As will be described in greater detail below, retaining protrusion (914) is operable to engage grid plate adaptor (930) to hold guide cube (902) in place when guide cube (902) is inserted into grid plate adaptor (930).

Cube lock (920) comprises rotatable arm (922) which is configured to permit cannula (2402) of targeting set (2400) to slidably engage cube lock (920). Rotatable arm (922) includes a recess (924) approximately defined by the radius of cannula (2402). Rotatable arm (922) is projected proximally from guide cube (902) on a rotatable axle (924), which is rotatably secured to a corner of guide block (902). Axle (924) projects arm (922) proximally to a distance configured to permit arm (922) to capture depth stop device (2440) of targeting set (2400) between arm (922) and guide cube (902). Thus, cannula (2402) of targeting set (2400) may be inserted into guide hole (904) until depth stop device (2440) is positioned directly adjacent to guide cube (902). Arm (922) may then be rotated to contact cannula (2402) to secure depth stop device (2440).

It should be understood that in examples where guide hole (904) of guide cube (902) is alternatively positioned, recess (924) of rotatable arm (922) is likewise reconfigured to accommodate such positioning while retaining the functionality described above. For instance, in examples where guide hole (904) is laterally offset, the positioning of recess (924) is correspondingly laterally offset such that rotatable arm (922) is rotatable to position recess (924) substantially over guide hole (904). Similarly, in examples where guide hole (904) is positioned in a corner of guide cube (902), recess (924) is also correspondingly laterally offset to permit rotatable arm (922) to rotatably align recess (924) with guide hole (904). It should be further understood that although only one guide cube (902) is show, in some examples a plurality of guide cubes (902) having the alternative characteristics described above are used interchangeably to selectively achieve numerous alternative targeting positions.

Figure 36:
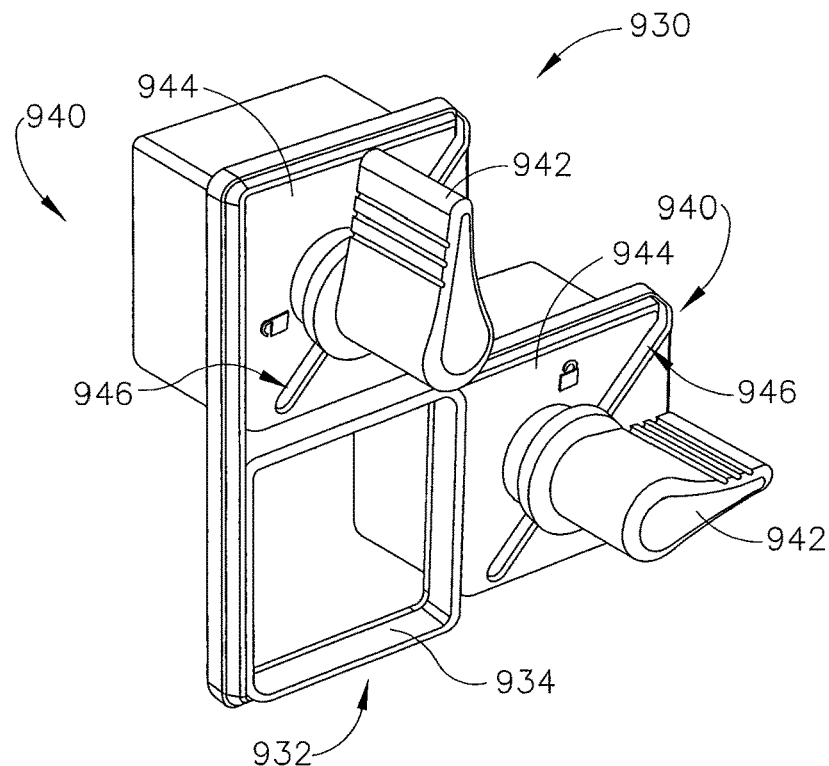
FIG. 36 depicts a perspective view of a grid plate adaptor for use with the localization fixture of FIG. 33.
Figure 37:
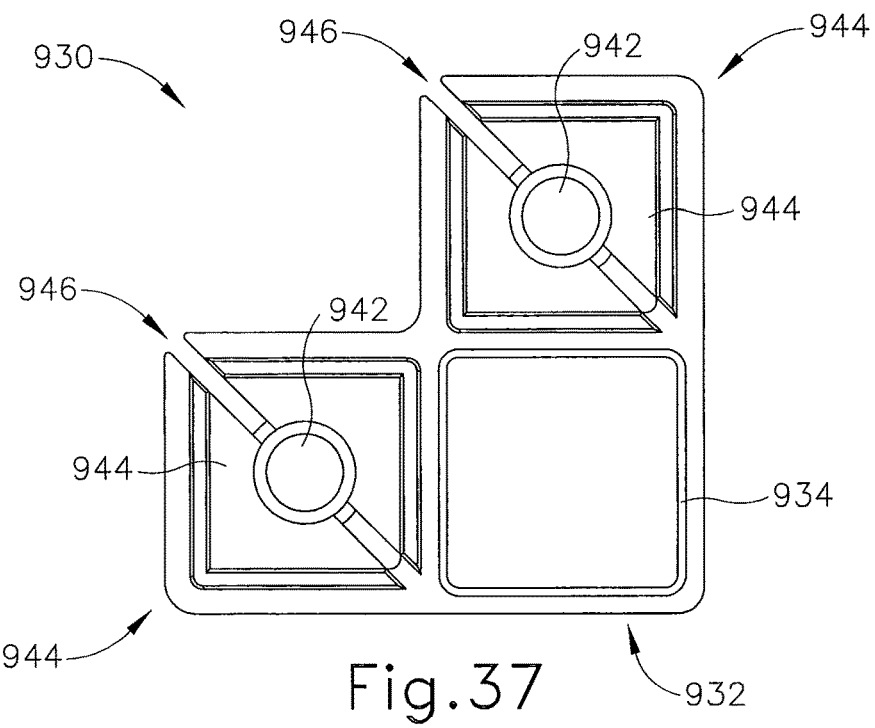
FIG. 37 depicts a back elevational view of the grid plate adaptor for use with the localization fixture of FIG. 33.
Figure 38:
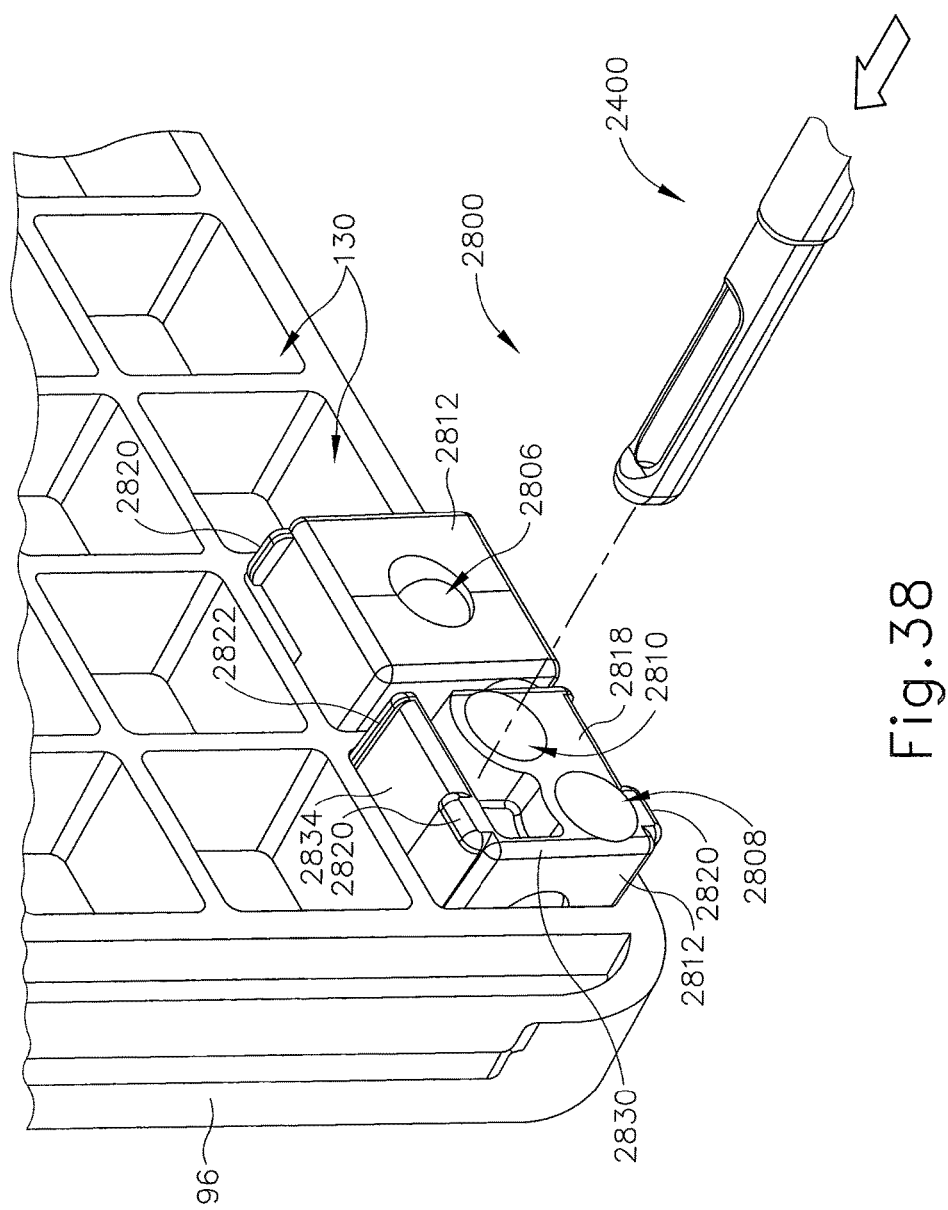
FIG. 38 depicts a perspective view of yet another exemplary alternative localization fixture for use with the biopsy system of FIG. 1.

FIGS. 36 and 37 show detailed views grid plate adaptor (930). Grid plate adaptor (930) includes three features (932, 940) arranged in an L-shape, which correspond to square recesses (130) in grid plate (96). Although the features (932, 940) described herein are shown and described as being in a particular order, it should be understood that such features may be rearranged in any suitable way. Additionally, some features (932, 940) may be duplicated as desired or simply omitted as will be apparent to those of ordinary skill in the art in view of the teachings herein. The three features (932, 940) of grid plate adaptor (930) comprise a guide cube aperture (932) and two locking features (940). Guide cube aperture (932) provides a space through which guide (902) cube may be inserted. Additionally, guide cube aperture (932) is defined by a ledge member (934), which provides a surface for integral tabs (908) of guide cube (902) to engage thereby preventing guide cube (902) from backing out of guide cube aperture (932).

Locking features (940) each comprise a rotatable actuator (942) having an integral cam feature (not shown). Actuator (942) is rotatable to lock grid plate adaptor (930) into grid plate (96). In particular, actuator (942) extends through a substantially solid portion (944) of grid plate adaptor (930). Substantially solid portion (944) includes a diagonally extending gap (946) and a hole (not shown) for actuator (942). Cam feature of actuator engages the hole in substantially solid portion (944) such that as actuator (942) is rotated, diagonally extending gap (946) is widened thereby outwardly deforming grid plate adaptor (930). The deformation of grid plate adaptor (930) causes grid plate adaptor (930) to engage an interior wall of given square recesses (130) in grid plate (96) to lock grid plate adaptor (930) in place. With grid plate adaptor (930) locked in place, guide cube (930) may be inserted into guide cube aperture (932) to guide targeting assembly (2400). Other suitable ways in which grid plate adaptor (930) may be selectively secured to grid plate (96) will be apparent to those of ordinary skill in the art in view of the teachings herein.

C. Exemplary Guide Cube with Living Hinge

FIGS. 38-41 show an exemplary alternative targeting set guide assembly (2800) that may be used in combination with grid plate (96) and any of the various targeting sets (89, 500, 2400, 2500, 700) described herein. While guide assembly (2800) is shown as being used with targeting set (2400), it should be understood that guide assembly (2800) may be used with any other targeting set (89, 500, 2500, 700) described herein, any of the targeting sets described in any of the references that are cited herein, and/or any other suitable kinds of targeting sets. It should also be understood that guide assembly (2800) may serve as a substitute for guide cube (104). Guide assembly (2800) is thus operable to guide targeting set (2400) as targeting set (2400) is inserted through grid plate (96); then support targeting set (2400) and an associated biopsy device once targeting set (2400) has fully engaged guide assembly (2800).

Guide assembly (2800) of the present example comprises two guide cubes (2802) inserted into grid plate (96) in adjacent square recesses (130) of grid plate (96). Generally and as will be described in greater detail below, targeting set (2400) is insertable into a selected guide cube (2802) to guide and support targeting set (2400). Each guide cube (2802) is insertable into grid plate (96) via a square recess (130), which secures guide cube (2802) along with targeting set (2400) relative to grid plate (96).

Figure 39:
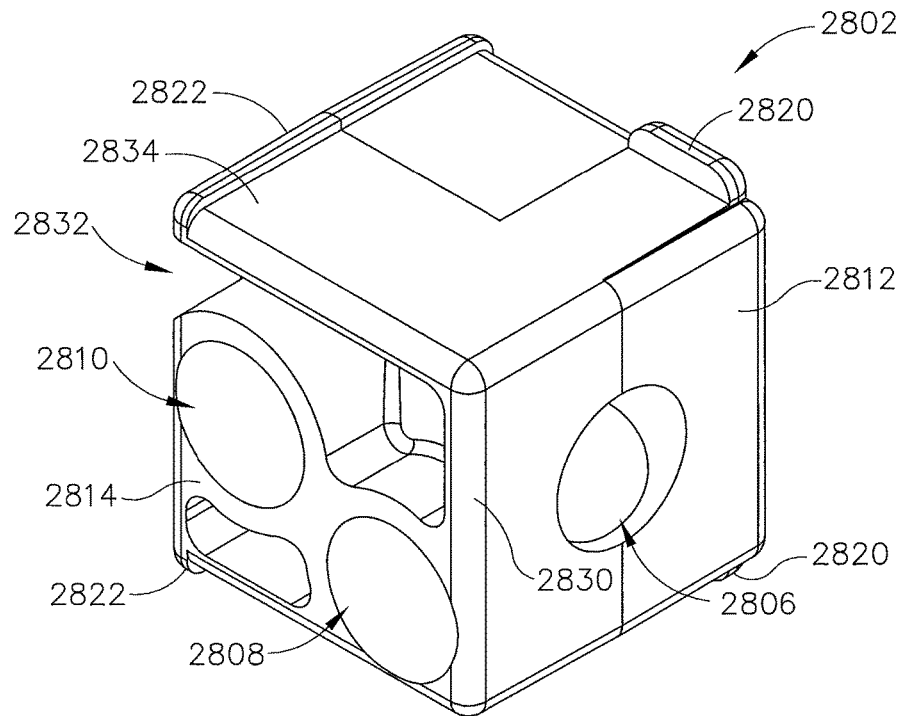
FIG. 39 depicts a perspective view of a guide cube for use with the localization fixture of FIG. 38.
Figure 40:
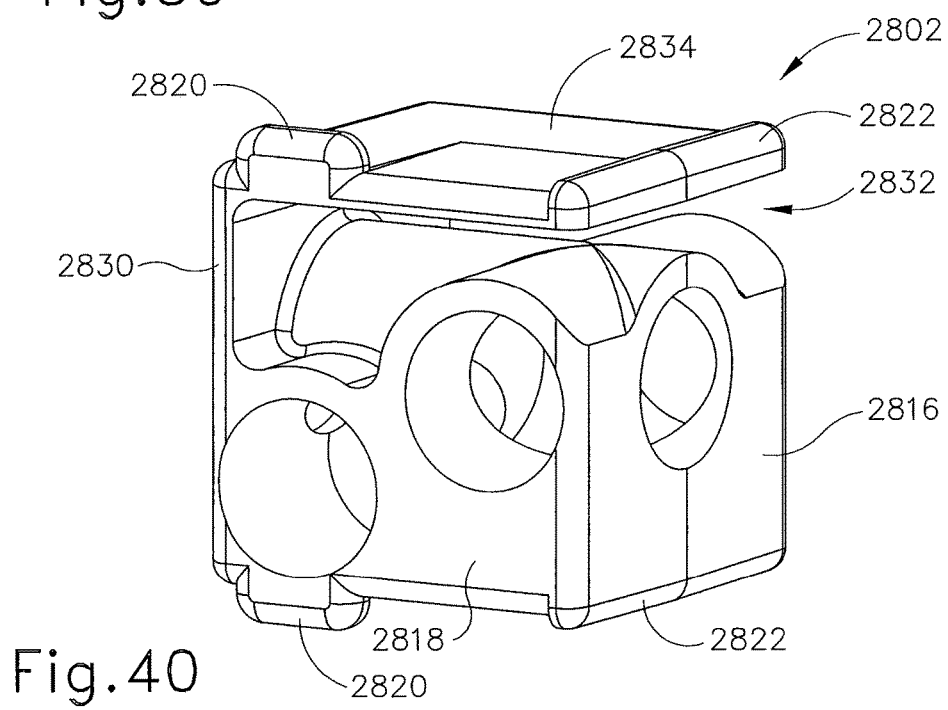
FIG. 40 depicts another perspective view of the guide cube of FIG. 39.
Figure 41:
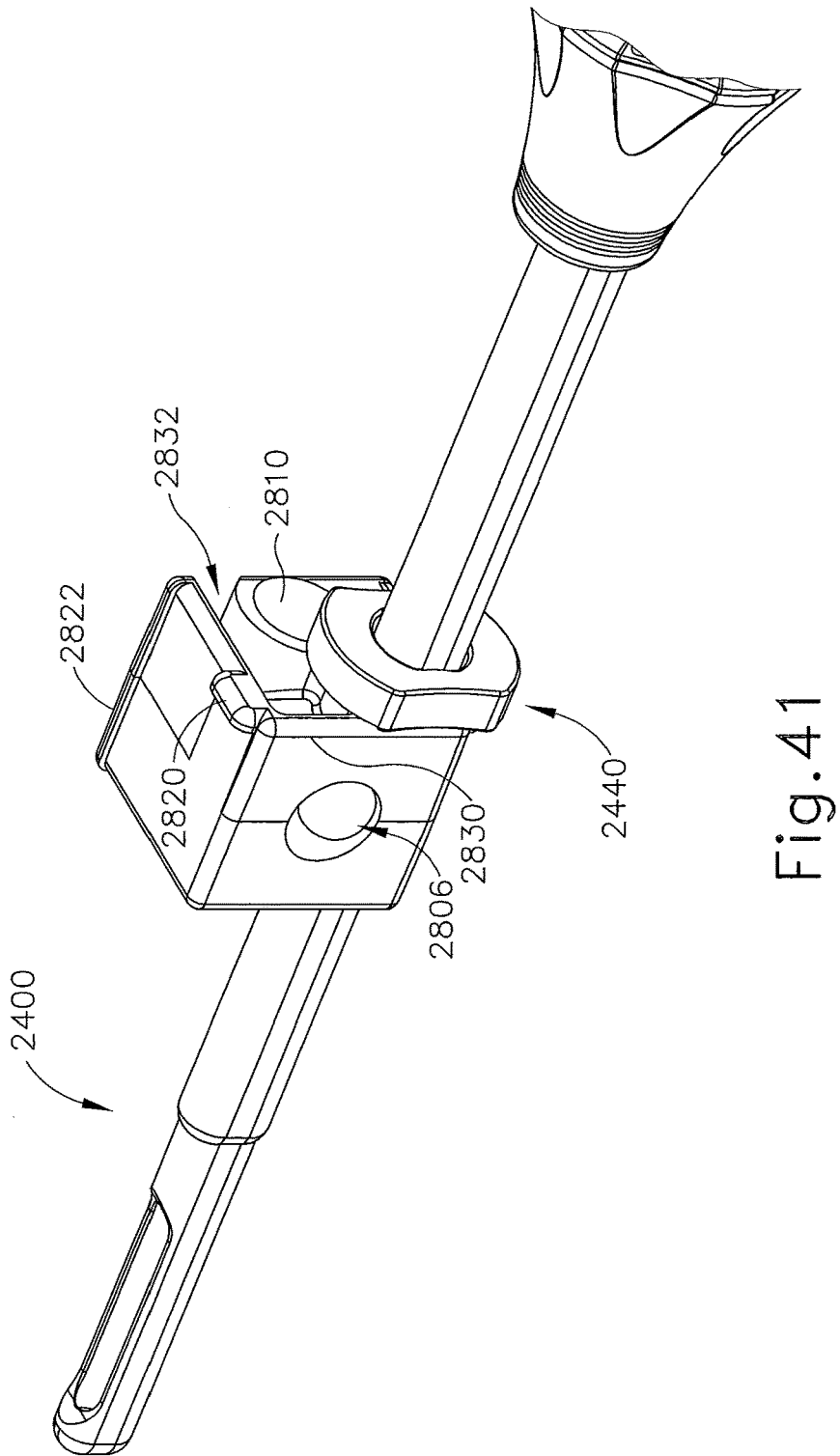
FIG. 41 depicts yet another perspective view of the guide cube of FIG. 39, with a targeting cannula inserted therethrough.
Figure 42:
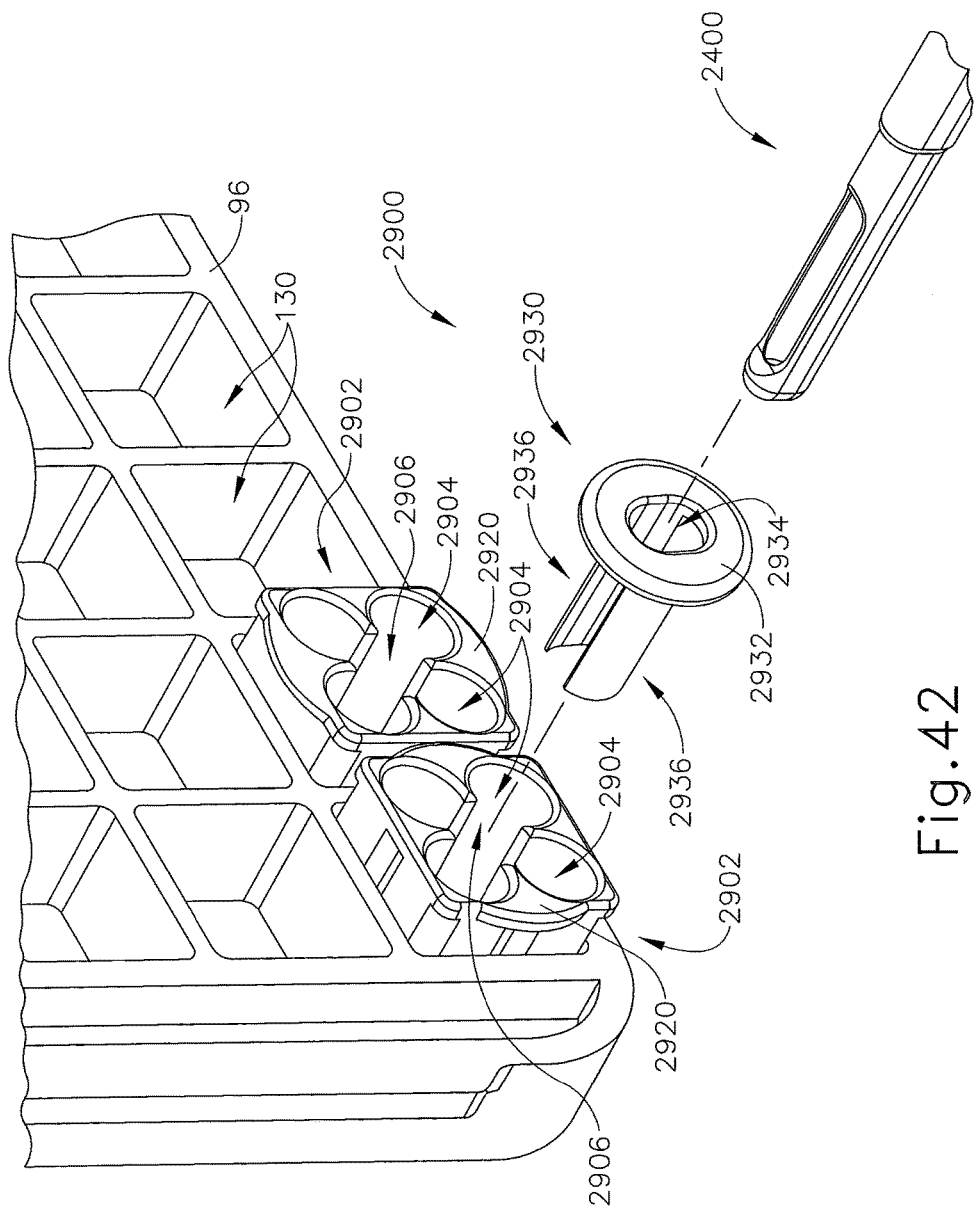
FIG. 42 depicts a perspective view of another exemplary alternative localization fixture for use with the biopsy system of FIG. 1.

As can be seen in FIG. 39, each guide cube (2802) of the present example includes a central guide hole (2806), a corner guide hole (2808), and an off-center guide hole (2810). Central guide hole (2806) extends orthogonally through guide cube (2802) from a first face (2812) to an opposite third face (2816) (FIG. 40). Similarly, corner guide hole (2808) and off-center guide hole (2810) extend orthogonally through guide cube (2802) from a second face (2814) to an opposite fourth face (2818) (FIG. 40). As will be understood, guide cube (2802) is configured such that a selected face (2812, 2818) may be oriented proximally relative to grid plate (96) to select whether central guide hole (2806) or corner (2808) and off-center guide holes (2810) are usable. Guide cube (2802) may then be selectively rotated about the selected face (2812, 2818) optionally a quarter turn, half turn, or three quarter turn. Thus, guide cube (2802) is similar to guide cube (104) described above in that guide cube (2802) may be oriented in several different ways within grid plate (96) to allow for a plurality of different positions for targeting set (2400).

Guide cube (2802) additionally comprises two pairs of different tab members (2820, 2822) protruding from guide cube (2802). Tab members (2820, 2822) may generally function to locate guide cube (2802) relative to grid plate (96) and to maintain guide cube (2802) within grid plate (96). As can be seen, tab members (2820, 2822) include a first tab pair (2820) and a second tab pair (2822). First tab pair (2820) is positioned adjacent to first face (2812) such that first tab pair (2820) extends away from first face (2812) toward third face (2816). First tab pair (2820) is configured to prevent guide cube (2802) from being over inserted into grid plate (96). Second tab pair (2822) is positioned adjacent to second face (2814) such that first tab pair (2820) extends away from second face (2814) toward fourth face (2818). Second tab pair (2822) is configured to prevent guide cube (2802) from being inadvertently removed from grid plate (96) when guide cube (2802) is inserted into grid plate (96) with first face (2812) facing proximally.

FIG. 40 shows an alternative view of guide cube (2802) with third face (2816) and fourth face (2818) visible. As can be seen, second face (2814), third face (2816) and fourth face (2818) define an opening (2832) in guide cube (2802), which extends for substantially the length of fourth face (2818). The remaining portion of fourth face (2818) (and correspondingly second face (2814)) forms a living hinge portion (2830). Living hinge portion (2830) is thick enough such that living hinge portion (2830) is resiliently biased to maintain the cubic shape of guide cube (2802). Living hinge portion (2830) is nevertheless thin enough such that an upper portion (2834) of cube may flex relative to guide cube (2802). In other words, living hinge portion (2830) is configured to deform to enable insertion of guide cube (2802) into grid plate (96), while the resilient bias of living hinge portion (2830) may maintain outward pressure on the walls of a square recess (130) of grid plate (96) to maintain the location of guide cube (2802) in grid plate (96).

Returning to FIG. 38, in an exemplary mode of operation, guide cube (2802) may be inserted into a selected square recess (130) of grid plate (96). Optionally, an additional single or plurality of guide cubes (2802) may be inserted into grid plate (96). In the present example, a guide cube (2802) substantially similar to guide cube (2802) is inserted into grid plate (96) in an adjacent square recess (130). In other examples, a different guide cube (e.g., guide cube (104)) or combination of multiple guide cubes could be used. Yet in other examples, the additional guide cube (2802) may be positioned in other square recesses (130) besides the one shown.

Guide cube (2802) of the present example may be oriented within square recess (130) with first face (2812) or fourth face (2818) facing proximally relative to grid plate (96). When first face (2812) is positioned proximally, first tab pair (2820) may prevent guide cube (2802) from being over inserted into grid plate (96). Similarly, second tab pair (2822) may prevent guide cube (2802) from being inadvertently removed from grid plate (96). When fourth face (2818) is positioned proximally, first tab pair (2820) may also prevent guide cube (2802) from being over inserted into grid plate (96). Second tab pair (2822) along with living hinge portion (2830) may maintain guide cube (2802) within grid plate (96) by engaging the wall of square recess (130).

With guide cube (2802) inserted in grid plate (96), targeting set (2400) may be inserted into a desired corner guide hole (2808) or off-center guide hole (2810) (when fourth face (2818) is facing proximally), or central guide hole (2806) (when first face (2812) is facing proximally). As can be best be seen in FIG. 25, targeting set (2400) is inserted into guide cube (2802) until depth stop device (2440) is reached thereby preventing further insertion. Targeting set (2400) may then be maintained at the depth determined by depth stop device (2440) or may be backed off by a user as desired.

D. Exemplary Guide Cube with Five Guide Holes

FIGS. 42-46 show another exemplary alternative targeting set guide assembly (2900) that may be used in combination with grid plate (96) and any of the various targeting sets (89, 500, 2400, 2500, 700) described herein. While guide assembly (2900) is shown as being used with targeting set (2400), it should be understood that guide assembly (2900) may be used with any other targeting set (2500) described herein, any of the targeting sets described in any of the references that are cited herein, and/or any other suitable kinds of targeting sets. It should also be understood that guide assembly (2900) may serve as a substitute for guide cube (104). Guide assembly (2900) is thus operable to guide targeting set (2400) as targeting set (2400) is inserted through grid plate (96); then support targeting set (2400) and an associated biopsy device once targeting set (2400) has fully engaged guide assembly (2900).

Guide assembly (2900) of the present example comprises a guide cube (2902). Generally and as will be described in greater detail below, targeting set (2400) is insertable into guide cube (2902), which guides and supports targeting set (2400). While two guide cubes (2902) are shown, it should be understood that any other suitable number of guide cubes (2902) may be used. As will also be described in greater detail below, although guide assembly (2900) is shown in FIG. 26 as using two substantially similar guide cubes (2902), guide cube (2902) may be combined with other guide cubes (104, 2802) described herein.

Figure 43:
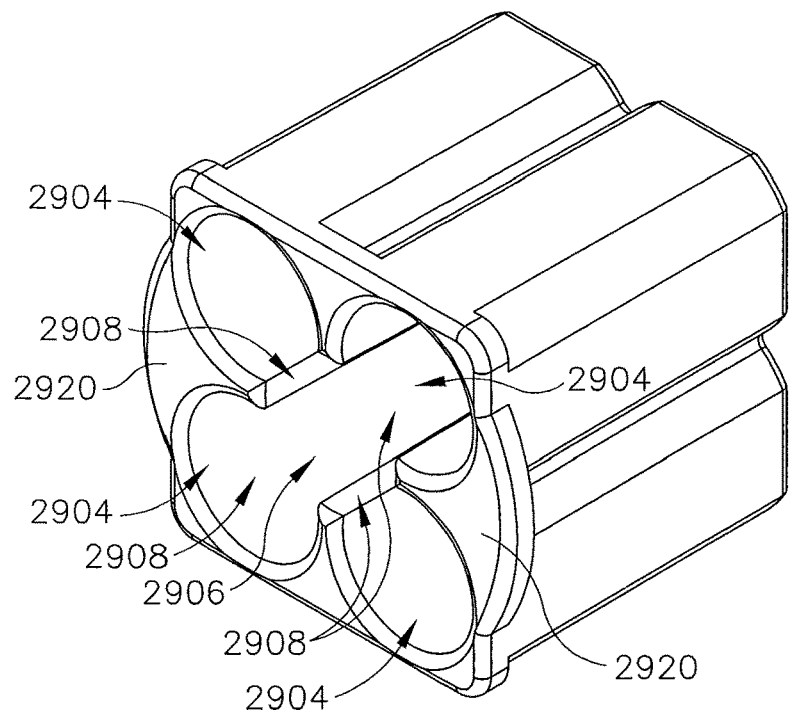
FIG. 43 depicts a perspective view a exemplary alternative guide cube for use with the localization fixture of FIG. 42.

As can be seen in FIG. 43, guide cube (2902) comprises four corner guide holes (2904) and a single central guide hole (2906). Guide holes (2904, 2906) extend proximally and perpendicularly from a proximal face (2910) toward a distal face (not shown). Unlike guide cube (2802), described above, guide cube (2902) is configured to be insertable into grid plate (96) in a single direction such that proximal face (2910) always faces proximally relative to grid plate (96). Proximal face (2910) includes a pair of rounded tabs (2920) to prevent over insertion of guide cube (2902) into grid plate (96).

Guide holes (2904, 2906) are sized to receive targeting set (2400). Because of this, corner guide holes (2904) overlap with central guide hole (2906) such that each corner guide hole (2904) defines an open portion (2908) where this overlap occurs. In some examples, targeting set (2400) may have an ovular, rather than circular, cross-section. Accordingly, in such examples, targeting set (2400) may inadvertently pass through a given open portion (2908) of each guide hole (2904, 2906). Thus, in some examples it may be beneficial to include a retainer guide (2930) to effectively provide a circular profile to targeting set (2400), thereby maintaining targeting set (2400) in a selected guide hole (2904, 2906).

Figure 44:
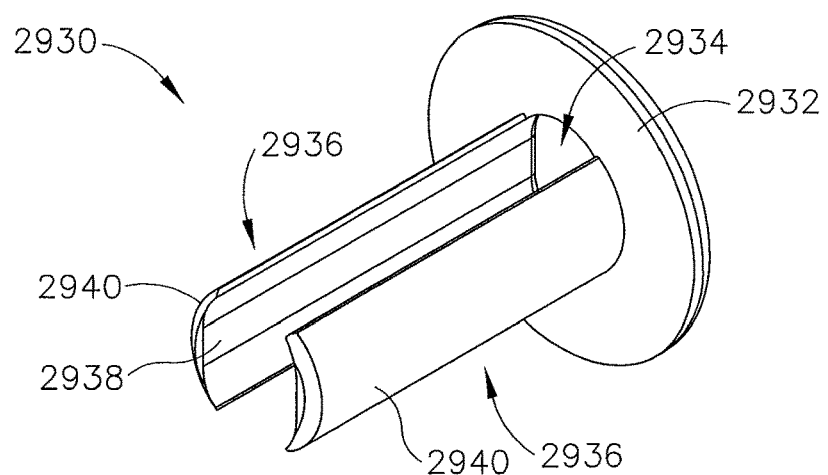
FIG. 44 depicts a perspective view of a retainer guide for use with the guide cube of FIG. 43.

FIG. 44 shows an exemplary retainer guide (2930) that may be used with guide assembly (2900). Retainer guide (2930) comprises a flange portion (2932) and a pair of distally extending guides (2936) (distal direction shown as out of the page in FIG. 44). Flange portion (2932) is configured to receive targeting set (2400) and abut guide cube (2902). To receive targeting set (2400), flange portion (2932) includes an ovular opening (2934). Guides (2936) extend distally from opening (2934) and include a relatively flat inner portion (2938) and a relatively circular outer portion (2940) Inner portion (2938) of guides (2936) is contoured to abut the elongated portion of the ovular cross-section of targeting set (2400). Outer portion (2940), in contrast, is rounded with a radius or diameter that is similar to the radius or diameter of the rounded portion of the ovular cross-section of targeting set (2400). Accordingly, as can best be seen in FIG. 45 targeting set (2400) may be inserted into retainer guide (2930) and then retainer guide (2930) along with targeting set (2400) may be inserted into guide cube (2902).

Figure 46:
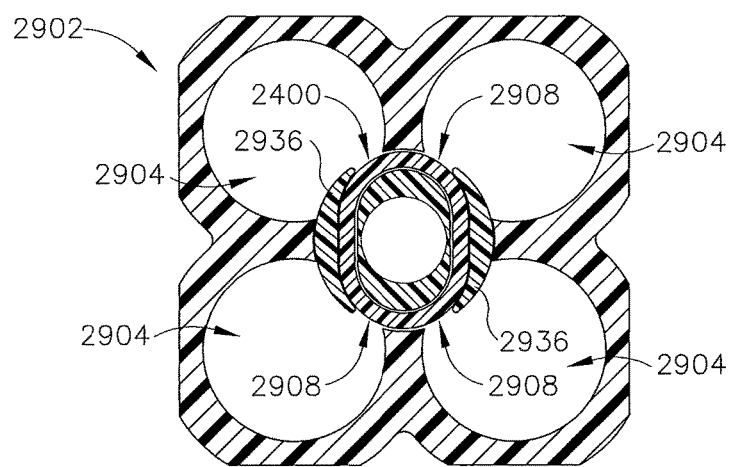
FIG. 46 depicts a cross-sectional view of the guide cube of FIG. 43, with the cross-section taken along line 46-46 of FIG. 45.

FIG. 46 shows a cross-section of guide cube (2902) with targeting set (2400) and retainer guide (2930) inserted into guide cube (2902). As can be seen, targeting set (2400) together with the outer portions (2940) of guides (2936) maintain a relatively circular cross-section around the perimeter of the combination of targeting set (2400) and retainer guide (2930). Thus, targeting set (2400) may be rotated to any desired angular position within a given guide hole (2904, 2906) without passing through open portion(s) (2908) of the given guide hole (2904, 2906).

Figure 45:
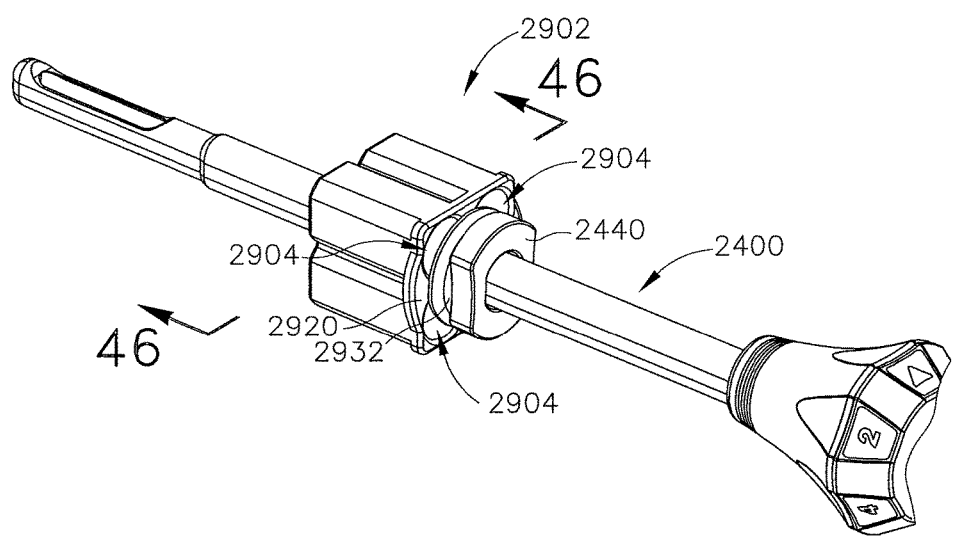
FIG. 45 depicts a perspective view of the guide cube of FIG. 43, with a targeting cannula inserted therethrough.

Returning to FIG. 42, in an exemplary mode of operation, one or more guide cubes (2902) may be inserted into a square recess (130) of grid plate (96), similarly to guide cube (2802) described above. In some examples, guide cube (2902) is oversized relative to square recess (130) such that guide cube (2902) is held within grid plate (96) by a friction fit. A user may then insert targeting set (2400) into retainer guide (2930). Once retainer guide (2930) has been inserted onto targeting set (2400), targeting set (2400) may be inserted into a selected guide hole (2904, 2906). Targeting set (2400) may be inserted into guide cube (2902) until depth stop device (2440) prevents further insertion. Retainer guide (2930) may thus be disposed between depth stop device (2440) and guide cube (2902) (as shown in FIG. 45). Targeting set (2400) may then be rotated to any desired angular position relative to guide block (2902) to perform a biopsy procedure.

Figure 47:
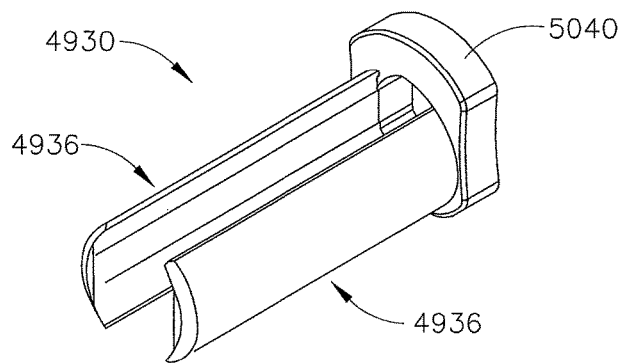
FIG. 47 depicts a perspective view of an exemplary alternative retainer guide for use with the guide cube of FIG. 43.

FIG. 47 shows an exemplary alternative retainer guide (4930) that may be used with guide assembly (2900) as an alternative to retainer guide (2930). Retainer guide (4930) is substantially the same as retainer guide (2930), except retainer guide (4930) of the present example unitarily combines retainer guide (4930) with a depth stop device (5040). In particular, depth stop device (5040) is substantially the same as depth stop device (2440) described above. Yet, two guides (4936) extend distally from depth stop device (5040). Guides (4936) are substantially the same as guides (2936) described above such that the particular details of guides (4936) will not be described here. In an exemplary use, retainer guide (4930) is used with guide assembly (2900) as described above with respect to retainer guide (2930), except in this example, depth stop device (5040) is incorporated into retainer guide (4930) such that retainer guide (4930) and depth stop device (5040) may be inserted onto targeting set (2400) in a single step.

E. Exemplary Guide Cube with Four Guide Holes

Figure 48:
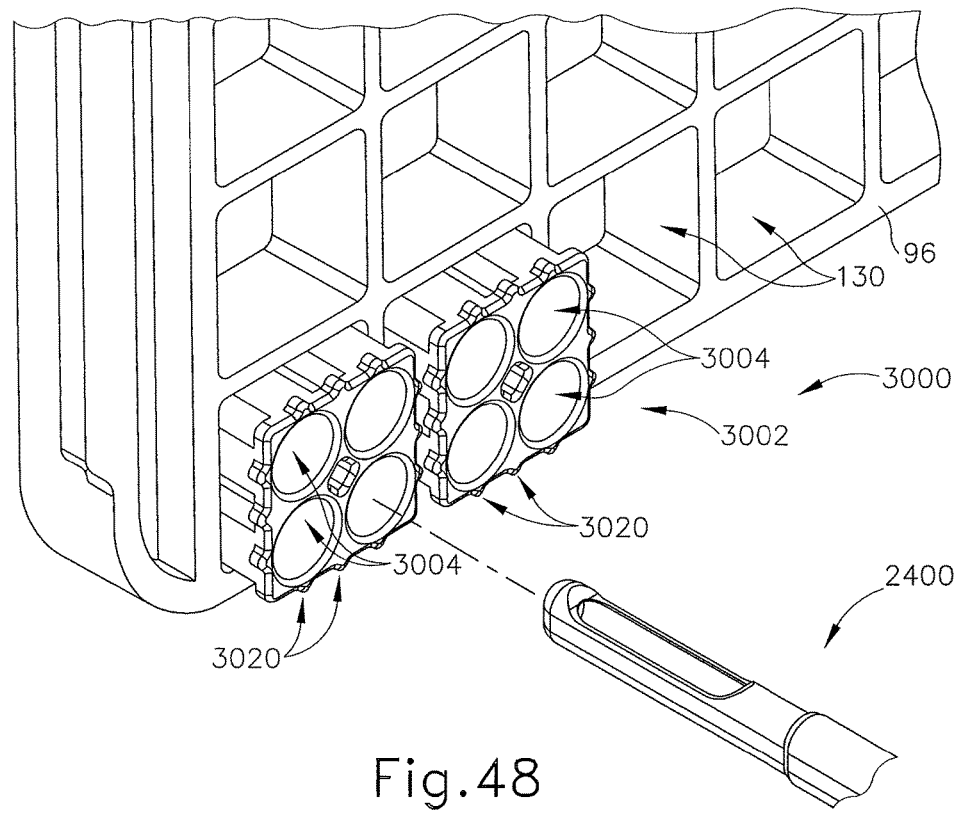
FIG. 48 depicts a perspective view of another exemplary alternative localization fixture for use with the biopsy system of FIG. 1.
Figure 49:
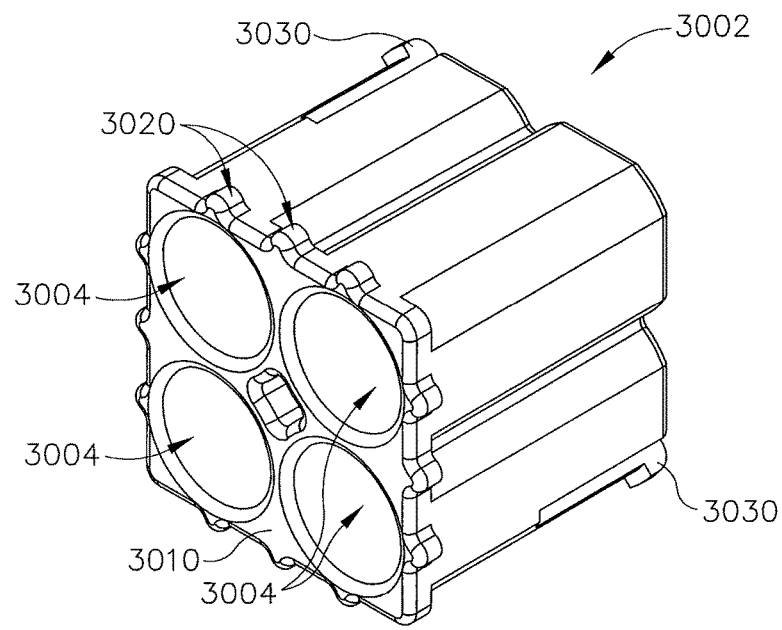
FIG. 49 depicts a perspective view of a guide cube for use with the localization fixture of FIG. 48.
Figure 50:
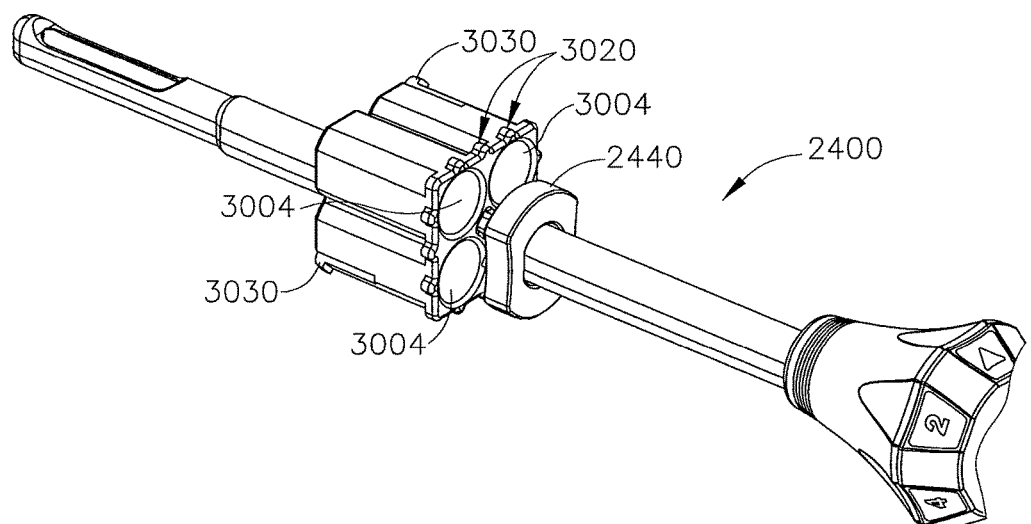
FIG. 50 depicts a perspective view of the guide cube of FIG. 49, with a targeting cannula inserted therethrough.

FIGS. 48-50 show another exemplary alternative targeting set guide assembly (3000) that may be used in combination with grid plate (96) and any of the various targeting sets (89, 500, 2400, 2500, 700) described herein. While guide assembly (3000) is shown as being used with targeting set (2400), it should be understood that guide assembly (3000) may be used with any other targeting set (89, 500, 2500, 700) described herein, any of the targeting sets described in any of the references that are cited herein, and/or any other suitable kinds of targeting sets. It should also be understood that guide assembly (3000) may serve as a substitute for guide cube (104). Guide assembly (3000) is thus operable to guide targeting set (2400) as targeting set (2400) is inserted through grid plate (96); then support targeting set (2400) and an associated biopsy device once targeting set (2400) has fully engaged guide assembly (3000).

Guide assembly (3000) of the present example comprises a guide cube (3002). Generally and as will be described in greater detail below, targeting set (2400) is insertable into guide cube (3002), which guides and supports targeting set (2400). As will also be described in greater detail below, although guide assembly (3000) is shown in FIG. 48 as using two substantially similar guide cubes (3002), guide cube (3002) may be combined with other guide cubes (104, 802, 902, 2802, 2902) described herein. It should also be understood that a single guide cube (3002) may be used by itself, such that additional guide cubes of any form are not required.

As can be seen in FIG. 49, guide cube (3002) comprises four corner guide holes (3004). Guide holes (3004) extend proximally and perpendicularly from a proximal face (3010) toward a distal face (not shown). Unlike guide cube (2802), described above, guide cube (3002) is configured to be insertable into grid plate (96) in a single direction such that proximal face (3010) always faces proximally relative to grid plate (96). Proximal face (3010) includes a plurality of rounded tabs (3020) to prevent over insertion of guide cube (2902) into grid plate (96). Additionally, guide cube (3002) includes two resiliently biased tab members (3030) on the distal end of guide cube (3002). Tab members (3030) are configured to engage the distal side of grid plate (96) to thereby prevent inadvertent removal of guide cube (3002) from grid plate. Alternatively, tab members (3030) may bear against the wall of an adjacent opening of grid plate (96) thereby providing a grip between guide cube (3002) and grid plate (96) through friction.

In an exemplary mode of operation, one or more guide cubes (3002) may be inserted into a square recess (130) of grid plate (96), similarly to guide cube (2802) described above. Other guide cubes (104, 802, 902, 2802, 2902) described herein may also be used along with guide cube (3002) in guide assembly (3000) similarly to the examples described above with respect to guide cube (2802). Once guide cube (3002) is inserted into grid plate (96), rounded tabs (3020) may prevent over insertion of guide cube (3002) into grid plate (96). Similarly, tab members (2930) may prevent inadvertent removal of guide cube (3002) by engaging the distal side of grid plate (96) or by bearing against inner sidewalls of grid plate (96). As another merely illustrative alternative, guide cube (3002) may additionally be oversized relative to square recess (130) such that guide cube (3002) is held in place within grid plate (96) by a friction fit.

A user may then insert targeting set (2400) into a selected guide hole (3004). Targeting set (2400) may be inserted into guide cube (3002) until depth stop device (2440) prevents further insertion (as shown in FIG. 50). Targeting set (2400) may then be rotated to any desired angular position relative to guide cube (3002) to perform a biopsy procedure.

VII. Exemplary Alternative Biopsy Systems

As noted above, various kinds of biopsy devices (14, 200, 300) may be used in combination with targeting set (89) and guide cube (104) of biopsy system (10). It should also be understood that those same biopsy devices (14, 200, 300), among other kinds of biopsy devices, may also be used with the various targeting sets (2400, 2500) shown in FIGS. 12-21; and with the guide assemblies (2800, 2900, 3000) shown in FIGS. 22-33. Various other examples of biopsy devices that may be used with targeting sets (89, 2400, 2500) and guide assemblies (2800, 2900, 3000) are described in greater detail below; while still other examples will be apparent to those of ordinary skill in the art in view of the teachings herein. It should also be understood that the biopsy devices described below may be used with various other kinds of targeting sets and guide assemblies, including but not limited to the various targeting sets and guide assemblies that are described in the references cited herein.

A. Exemplary Biopsy System with Consolidated Cable

Figure 51:
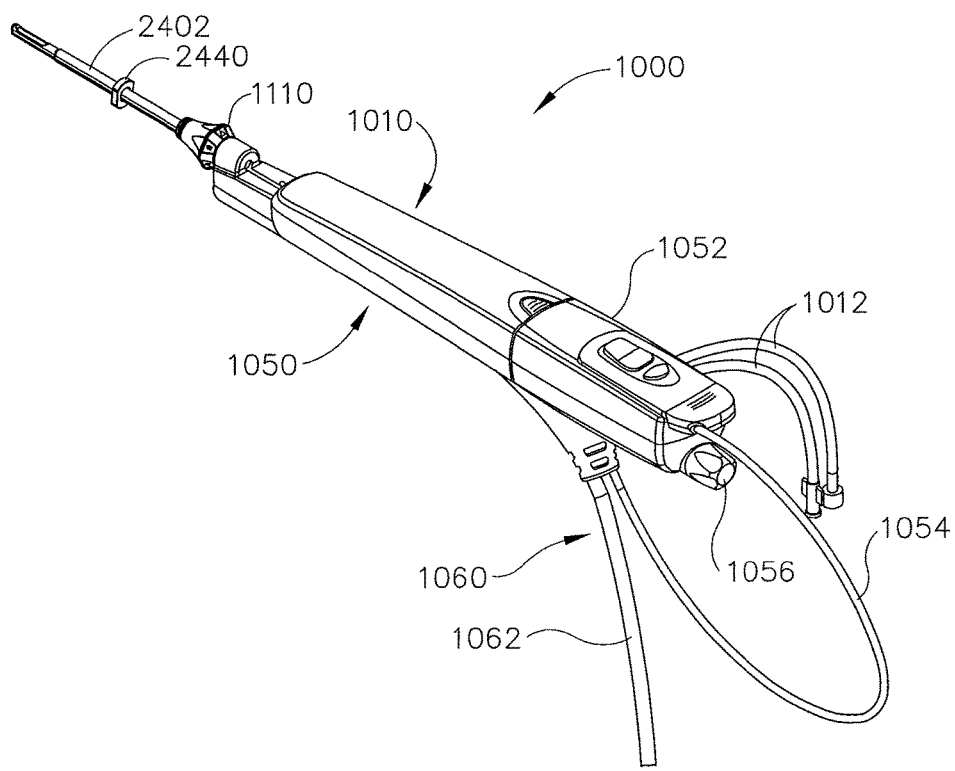
FIG. 51 depicts a perspective view of an exemplary alternative biopsy device combined with the targeting cannula of FIG. 18.
Figure 52:
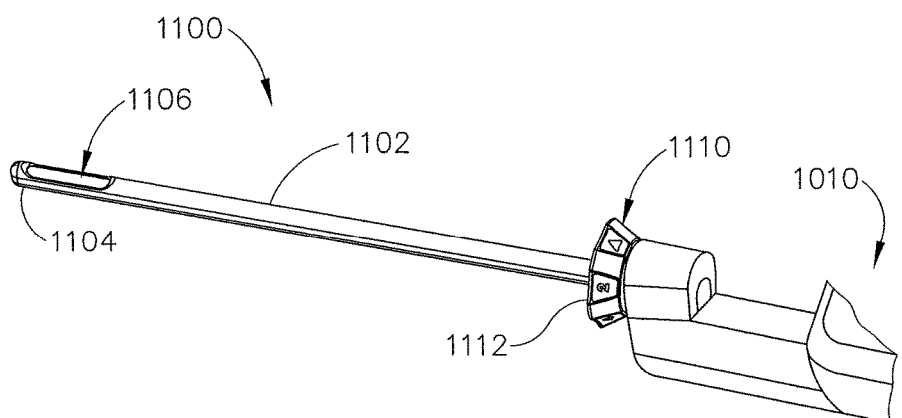
FIG. 52 depicts a perspective view of a needle assembly of the biopsy device of FIG. 51.

FIG. 51 shows a combination of an exemplary biopsy device (1000) with targeting cannula (2402) of FIG. 12. Biopsy device (1000) of this example is substantially similar to biopsy device (14). In particular, biopsy device (1000) comprises a probe portion (1010) and a holster portion (1050). Probe portion (1010) includes a distally projecting needle assembly (1100), which is rotatable relative to the remainder of probe portion (1010). In particular, needle assembly (1100) is rotatable about the longitudinal axis defined by needle assembly (1100). As shown in FIG. 52, needle assembly (1100) comprises an elongate cannula (1102) with a blunt distal tip (1104) and a lateral, tissue receiving aperture (1106) formed proximal to tip (1104). Needle assembly (1100) further includes a hub (1110), which is located a the proximal end of cannula (1102) and is configured to enable an operator to grasp and rotate needle assembly (1100) about the longitudinal axis of needle assembly (1100), relative to the rest of probe portion (1010). Hub (1110) is configured substantially similar to index bezel (2430), such that hub (1110) complements hub (2404) of targeting cannula (2402). In particular, hub (1110) includes distally projecting protrusions (1112) that are configured to snap into corresponding retention features (2418) of hub (2404). Thus, cannula (1102) of needle assembly (1100) may be inserted into cannula (2402); and protrusions (1112) may cooperate with retention features (2418) to secure needle assembly (1100) with cannula (2402).

Probe portion (1010) of the present example also includes a set of tubes (1012) that are configured to provide fluid communication between probe portion (1010) and control module (3300). Such fluid communication may be provided in accordance with the teachings of any of the references cited herein. By way of example only, control module (1200) may provide vacuum, saline, and/or atmospheric air to probe portion (1010) via tubes (1012). In addition or in the alternative, control module (1200) may receive bodily fluids, saline, and/or atmospheric air from probe portion (1010) via tubes (1012).

Holster portion (1050) of the present example includes a detachable remote keypad (1052) with an associated electrical cable (1054), as well as an aft thumbwheel (1056). Keypad (1052), cable (1054), and thumbwheel (1056) are identical to keypad (62), cable (24), and thumbwheel (63) described above. A cable assembly (1060) also extends from holster portion (1050) and couples holster portion (1050) with control module (1200). Cable assembly (1060) includes one or more rotary drive cables (not shown) that is/are contained within an outer sheath (1062). Such rotary drive cable(s) provide rotary power to actuate a cutter (not shown) of biopsy device (1000) in accordance with the teachings of various references cited herein. One or more electrical cables (not shown) is/are also contained within outer sheath (1062). Such electrical cable(s) is/are in communication with electrical cable (1054), thereby enabling electrical communication between keypad (1052) and control module (3300). Although not shown, it should be understood that in some examples, cable assembly (1060) may comprise a plurality of discrete cables. For instance, in some examples outer sheath (1062) only contains a rotary drive cable, while any electrical cables are bundled separately in another cable or cables.

Figure 53:
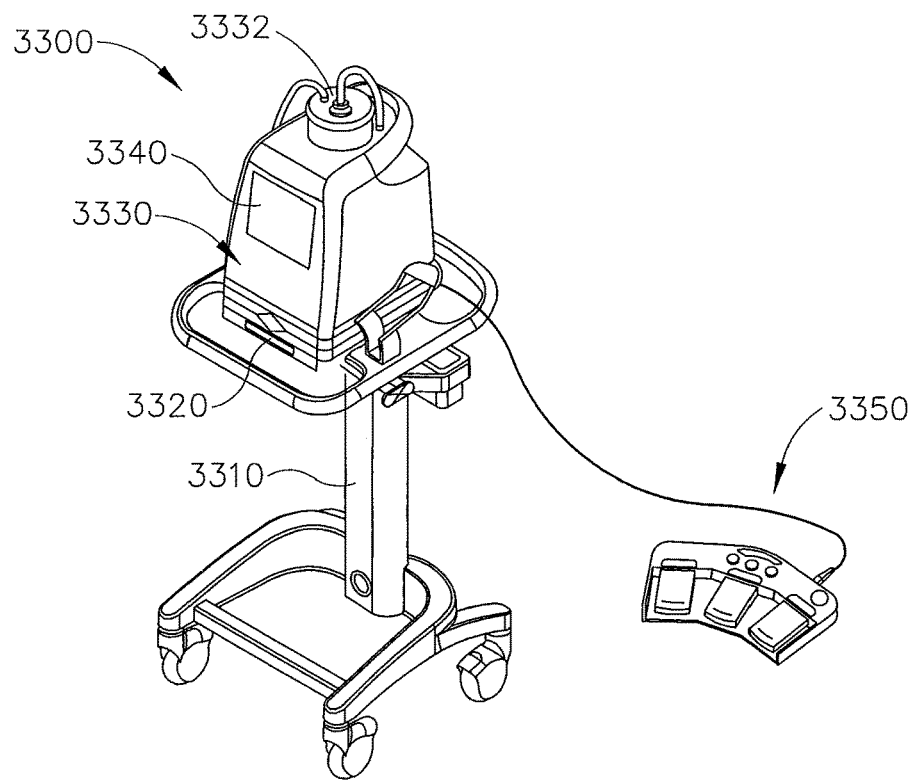
FIG. 53 depicts a perspective view of a control module for use with the biopsy device of FIG. 51.

FIG. 53 shows control module (3300) in greater detail. Control module (3300) is substantially identical to control module (12) and is configured for use with biopsy device (1000). Control module (3300) of this example comprises an upright stand (3310), a cable interface (3320), a tube set interface (3330), a display screen (3340), and a footswitch assembly (3350). Cable interface (3320) is configured to couple with cable assembly (1060). Various suitable ways in which cable interface (3320) may be configured will be apparent to those of ordinary skill in the art in view of the teachings herein. By way of example only, cable interface (3320) may be configured and operable in accordance with at least some of the teachings of U.S. Pat. No. 8,617,084, entitled "Control Module Interface for MRI Biopsy Device," issued Dec. 31, 2013, the disclosure of which is incorporated by reference herein.

Tube set interface (3330) is configured to couple with tubes (1012) and is operable to provide communication of vacuum, saline, and/or atmospheric air to probe portion (1010) via tubes (1012). Tube set interface (3330) is further in communication with a vacuum canister (3332), which is seated in control module (3300). By way of example only, tube set interface (3330) may be configured and operable in accordance with at least some of the teachings of U.S. Pat. No. 6,162,187, entitled "Fluid Collection Apparatus for a Surgical Device," published Dec. 19, 2000, the disclosure of which is incorporated by reference herein. In some other versions, tube set interface (3330) is configured and operable in accordance with at least some of the teachings of U.S. Pub. No. 2013/0218047, entitled "Biopsy Device Valve Assembly," published Aug. 22, 2013, the disclosure of which is incorporated by reference herein. Other suitable ways in which tube set interface (3330) may be configured an operable will be apparent to those of ordinary skill in the art in view of the teachings herein.

Display screen (3340) is configured to provide a graphical user interface for the operator. By way of example only, display screen may display information relating to operation of biopsy device (1000) in accordance with the teachings of any of the various references cited herein. In some versions, display screen (3340) comprises a touch screen that is operable to directly receive user input from the operator. By way of example only, display screen (3340) may provide displays and operability in accordance with at least some of the teachings of U.S. Pub. No. 2014/0039343, entitled "Biopsy System," published Feb. 6, 2014, the disclosure of which is incorporated by reference herein. Additional ways in which display screen (3340) may be used will be described in greater detail below.

Figure 54:
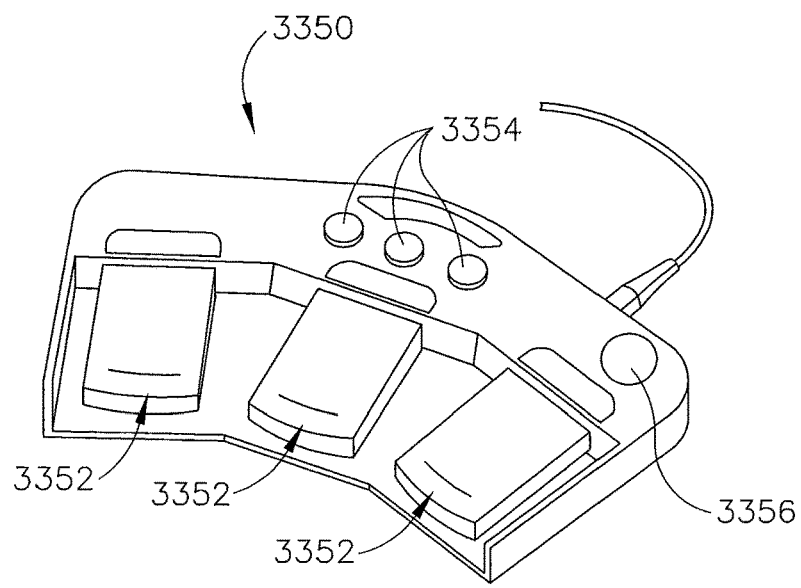
FIG. 54 depicts a perspective view of a footswitch assembly for use with the control module of FIG. 53.

Footswitch assembly (3350), as best seen in FIG. 54, includes a plurality of foot actuated switches (3352) that enable an operator to control operation of biopsy device (1000) in a hands-free fashion. Footswitch assembly (3350) also includes a plurality of light emitters (3354). Light emitters (3354) may be configured to indicate basic information regarding biopsy device (1000) to a user. For instance, in some examples light emitters (3354) may be color coded to indicate an error condition (red), a warning condition (yellow), and a ready condition (green). Alternatively, any other suitable configuration of light emitters (3354) may be used to convey information regarding biopsy device (1000) to a user. By way of example only, footswitch assembly (3350) may be configured and operable in accordance with the teachings of U.S. Pub. No. 2014/0039343, entitled "Biopsy System," published Feb. 6, 2014, the disclosure of which is incorporated by reference herein. Other suitable ways in which footswitch assembly (3350) may be configured and operable will be apparent to those of ordinary skill in the art in view of the teachings herein. It should also be understood that all other features of control module (3300) may be configured and operable in accordance with the teachings of U.S. Pub. No. 2014/0039343, entitled "Biopsy System," published Feb. 6, 2014, the disclosure of which is incorporated by reference herein; and/or any other reference cited herein.

Footswitch assembly (3350) further includes a biopsy device connector (3356). Biopsy device connector (3356) may be used as an alternative port by which biopsy device (1000) may connect to control module (3300). Such an alternative connection port may be desirable because in some instances, control module (3300) may be located outside of the MR imaging suite, while footswitch assembly (3350) may be located inside the MR imaging suite. Thus, biopsy device connector (3350) may allow a user to use a shorter cable set to connect to control module (3300). In the present example, cable assembly (1060) of biopsy device (1000) connects to biopsy device connector (3356). To accommodate such a connection, it should be understood that in some examples footswitch assembly (3350) may include a motor to power a rotary drive cable. Such a motor may be part of a module that is similar to cable interface (3320) described above. By way of example only, such a module may be configured and operable in accordance with at least some of the teachings of U.S. Pat. No. 8,617,084, entitled "Control Module Interface for MRI Biopsy Device," issued Dec. 31, 2013, the disclosure of which is incorporated by reference herein. In versions where cable assembly (1060) is driven by a motor or other mechanical driver that is located within footswitch assembly (3350), the length of a corresponding rotary drive cable may be substantially shorter (e.g., approximately three feet to six feet) than the length of cable assembly (1060) in versions where a corresponding rotary drive cable is driven by a motor or other mechanical driver that is located within control module (3300). Such a shorter rotary drive cable may be relatively easier to manage and/or may provide other advantages over a longer rotary drive cable.

Figure 55:
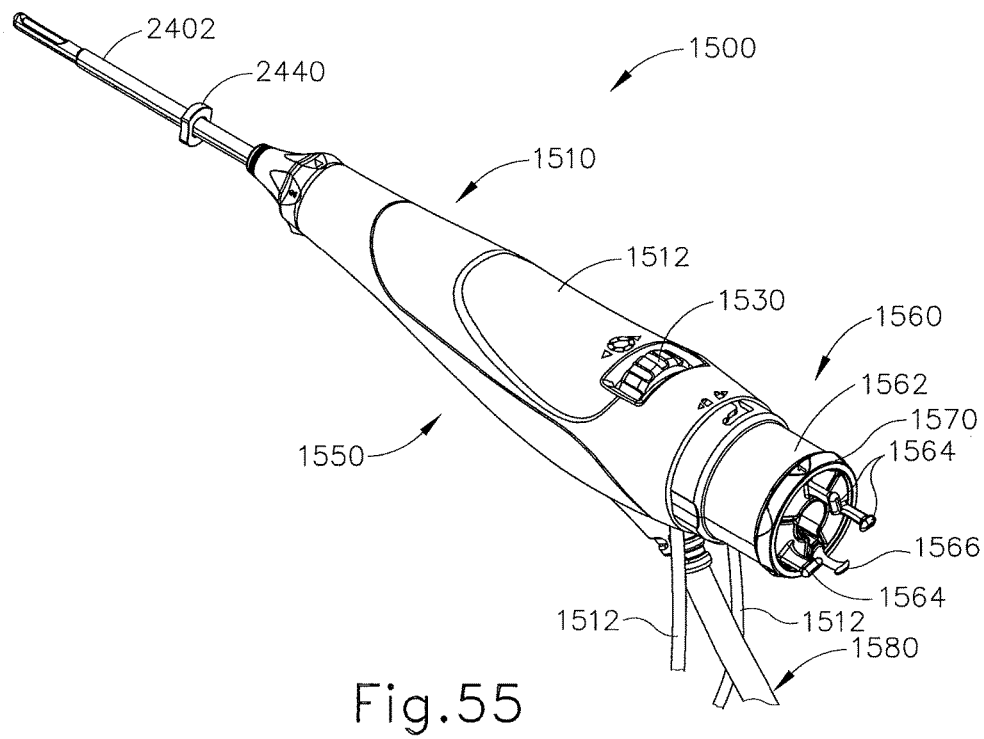
FIG. 55 depicts a perspective view of another exemplary alternative biopsy device combined with the targeting cannula of FIG. 18.
Figure 56:
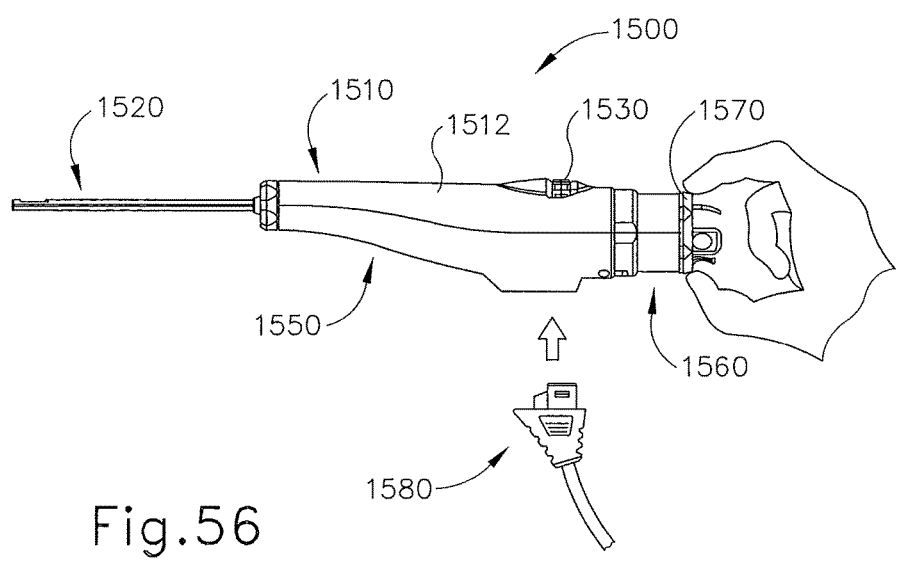
FIG. 56 depicts a side elevational view of the biopsy device of FIG. 55.

B. Exemplary Biopsy System with Central Thumbwheel and Manually Rotatable Tissue Sample Holder FIGS. 55-56 show a combination of another exemplary biopsy device (1500) with targeting cannula (2402) of FIG. 12. Biopsy device (1500) of this example comprises a probe portion (1510) and a holster portion (1550). Probe portion (1510) includes a distally projecting needle assembly (1520). Needle assembly (1520) of this example is substantially similar to needle assembly (1100) described above, such that the details will not be repeated here. Unlike probe portion (1010), probe portion (1510) of this example includes a central thumbwheel (1530), which is exposed relative to a housing (1512) of probe portion (1510). Thumbwheel (1530) is configured to enable an operator to engage thumbwheel (1530) and thereby rotate needle assembly (1520) about the longitudinal axis of needle assembly (1520), relative to housing (1512). By way of example only, thumbwheel (1530) may be configured and operable in accordance with at least some of the teachings of U.S. Pat. No. 8,083,687, entitled "Tissue Biopsy Device with Rotatably Linked Thumbwheel and Tissue Sample Holder," issued Dec. 27, 2011, the disclosure of which is incorporated by reference herein. Other suitable ways in which thumbwheel (1530) may be configured and operable will be apparent to those of ordinary skill in the art in view of the teachings herein.

Probe portion (1510) and holster portion (1550) of the present example are unitarily combined such that they are inseparable and form a single piece. Accordingly, biopsy device (1500) of the present example is completely disposable and is discarded after a single use. In other examples, probe portion (1510) and holster portion (1550) are separable from each other. In such examples, only probe portion (1510) is disposable, while holster portion (1550) is reusable. Thus, in examples where probe portion (1510) is disposable, probe portion (1510) is discarded after a single biopsy procedure. For additional biopsy procedures, a new probe portion (1510) of substantially similar construction, or different construction may be inserted onto holster portion (1550).

Biopsy device (1500) of this example further includes a tissue sample holder assembly (1560) located at the proximal end of probe portion (1510). Tissue sample holder assembly (1560) comprises an outer cover (1562), a plurality of tissue receiving trays (1564), a plug (1566), and an inner member (not shown) that supports trays (1564) and plug (1566). Outer cover (1562) is transparent in the present example, though this is merely optional. The inner member is rotatable within cover (1562), such that the inner member may be rotated relative to housing (1512) while cover (1562) remains stationary relative to housing (1512). The inner member may thus be rotated to selectively index trays (1564) and plug (1566) relative to the longitudinal axis of needle assembly (1100). When a tray (1564) is aligned with the longitudinal axis of needle assembly (1100), that tray is configured to receive tissue samples severed by a cutter (not shown) that moves relative to the needle assembly (1520) in accordance with the teachings of various references cited herein. When plug (1566) is aligned with the longitudinal axis of needle assembly, plug (1566) may be removed to enable insertion of a biopsy site marker applier to deploy a biopsy marker through needle assembly (1100) in accordance with the teachings of various references cited herein.

By way of example only, at least part of tissue sample holder assembly (1560) may be configured and operable in accordance with at least some of the teachings of U.S. Pat. Pub. No. 2008/0214955, entitled "Presentation of Biopsy Sample by Biopsy Device," published Sep. 4, 2008, the disclosure of which is incorporated by reference herein; U.S. Pat. No. 8,702,623, entitled "Biopsy Device with Discrete Tissue Chambers," issued Apr. 22, 2014, the disclosure of which is incorporated by reference herein; U.S. Pat. Pub. No. 2013/0041256, entitled "Access Chamber and Markers for Biopsy Device," published Feb. 14, 2013, the disclosure of which is incorporated by reference herein; U.S. Pub. No. 2014/0039343, entitled "Biopsy System," published Feb. 6, 2014, the disclosure of which is incorporated by reference herein; U.S. patent application Ser. No. 14/469,761, entitled "Tissue Collection Assembly for Biopsy Device," filed Aug. 27, 2014, the disclosure of which is incorporated by reference herein; and/or any other reference that is cited herein.

Tissue sample holder assembly (1560) of the present example further includes a gripping ring (1570). Gripping ring (1570) is secured to the proximal end of the inner member and is rotatable relative to housing (1512) and outer cover (1562). Gripping ring (1570) is configured to enable an operator to grasp gripping ring (1570) (as shown in FIG. 55) and thereby rotate the inner member of tissue sample holder assembly (1560) to selectively index trays (1564) and plug (1566) relative to the longitudinal axis of needle assembly (1520). Gripping ring (1570) may comprise an elastomeric material, ridges, knurling, bumps, dimples, and/or any other suitable features or combination of features that may promote an operator to grasp and manipulate gripping ring (1570).

Probe portion (1510) of the present example further comprises a set of tubes (1514) that are configured to provide fluid communication between probe portion (1510) and control module (3300). Such fluid communication may be provided in accordance with the teachings of any of the references cited herein. By way of example only, control module (3300) (as shown in FIG. 53) may provide vacuum, saline, and/or atmospheric air to probe portion (1510) via tubes (1512). In addition or in the alternative, control module (3300) may receive bodily fluids, saline, and/or atmospheric air from probe portion (1510) via tubes (1512).

Holster portion (1550) of the present example comprises a cable assembly (1580), which couples holster portion with control module (3300). In the present example, cable assembly (1580) comprises one or more mechanical drive mechanisms that provide motive force to drive assemblies contained within holster portion (1550). Such one or more mechanical drive mechanisms are operable to transfer motive force from a motor contained in control module (3300) to holster portion (1550) without the motive force being affected by cable coiling or bends in cable assembly (1580). Such one or more mechanical drive mechanisms may be further operable to drive operation of the cutter that moves relative to needle assembly to sever tissue samples. By way of example only, such mechanical drive mechanisms may be configured and operable in accordance with the teachings of any of the references cited herein. In some versions, cable assembly (1580) comprises one or more electrical wires to provide electrical communication with one or more components within holster portion (1550) such as sensors and/or motors.

As can be seen in FIG. 56, cable assembly (1580) is configured to be selectively removable from holster portion (1550). Because holster portion (1550) of the present example is configured to be disposable, cable assembly (1580) is configured to be selectively removed to permit an operator to discard holster portion (1550). It should be understood that in examples where holster portion (1550) is reusable, cable assembly (1580) is alternatively not removable from holster portion (1550). Of course, the later feature is merely optional and in some examples utilizing a reusable holster portion (1550), cable assembly (1580) is also selectively separable from holster portion (1550).

Although not shown, in some examples cable assembly (1580) comprises one or more electrical cables, in lieu of the mechanical drive mechanisms described above. Such one or more electrical cables provide electrical power to one or more motors contained within holster portion (1550). Such one or more motors may be configured to drive operation of the cutter that moves relative to needle assembly (1520) to sever tissue samples. By way of example only, such one or more motors may be configured and operable in accordance with the teachings of any of the references cited herein. Similarly, the mechanism that drives the cutter may be configured and operable in accordance with the teachings of any of the references cited herein. In some other versions, cable assembly (1580) comprises one or more rotary drive cables. Other suitable ways in which cable assembly (1580) may be configured and operable will be apparent to those of ordinary skill in the art in view of the teachings herein.

As similarly described above with respect to biopsy device (1000), in some examples control module (3300) (as shown in FIG. 53) is configured for use with biopsy device (1500). As described above, control module (3300) comprises cable interface (3320), and tube set interface (3330). Cable interface (3320) is configured to couple with cable assembly (1580). Likewise, tube set interface (3330) is configured to couple with tube set (1514) and is operable to provide communication of vacuum, saline, and/or atmospheric air to probe portion (1510) via tubes (1514). It should be understood that while biopsy device (1500) is described herein as being usable with control module (3300), in other examples biopsy device (1500) may alternatively be usable with any other control module described herein.

Figure 57:
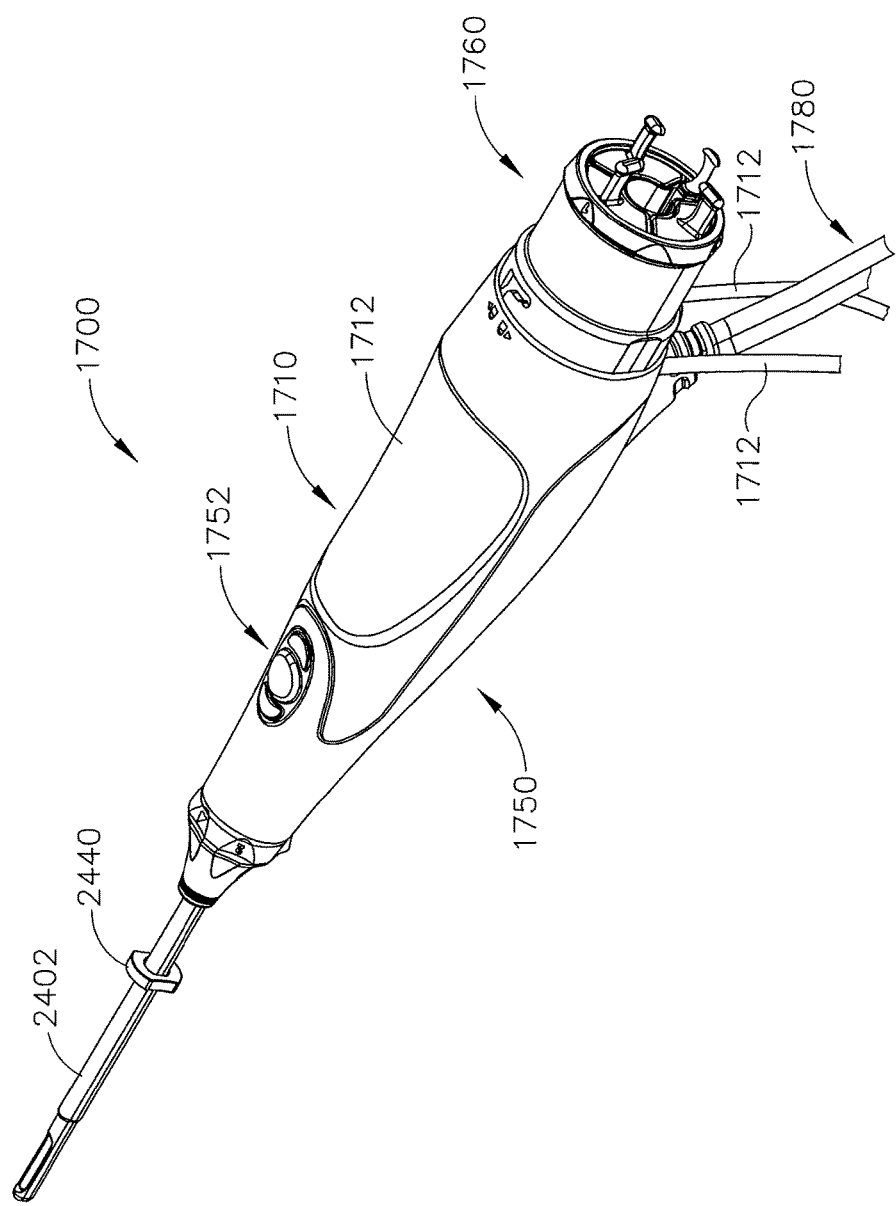
FIG. 57 depicts a perspective view of still another exemplary alternative biopsy device combined with the targeting cannula of FIG. 18.
Figure 58:
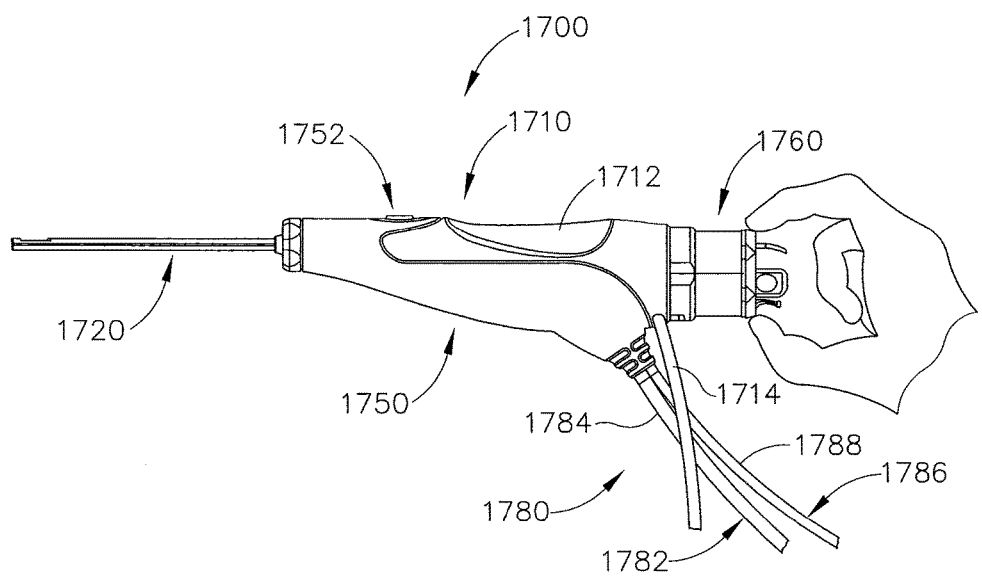
FIG. 58 depicts a side elevational view of the biopsy device of FIG. 57.

C. Exemplary Biopsy System with Distal Control Interface and Manually Rotatable Tissue Sample Holder FIGS. 57-58 show a combination of another exemplary biopsy device (1700) with targeting cannula (2402) of FIG. 12. Biopsy device (1700) of this example comprises a probe portion (1710) and a holster portion (1750). Probe portion (1710) includes a distally projecting needle assembly (1720). Needle assembly (1720) of this example is substantially similar to needle assembly (1100) described above, such that the details will not be repeated here. Except for the shape of probe portion (1710) and how probe portion (1710) is inserted into holster portion (1750), probe portion (1710) of this example is further substantially similar to probe portion (1010), such that the details will not be repeated here. Moreover, probe portion (1710) of this example includes a tissue sample holder assembly (1760), which is configured substantially similar to tissue sample holder assembly (1560), such that the details will not be repeated here.

Holster portion (1750) is substantially similar to holster portion (1050). However, unlike holster portion (1050), holster portion (1750) of this example includes a user interface feature (1752) comprising a plurality of buttons that are operable to control operation of biopsy device (1700). By way of example only, user interface feature (1752) may be configured and operable in accordance with at least some of the teachings of U.S. Pat. Pub. No. 2008/0214955, entitled "Presentation of Biopsy Sample by Biopsy Device," published Sep. 4, 2008, the disclosure of which is incorporated by reference herein; U.S. Pat. No. 8,277,394, entitled "Multi-Button Biopsy Device," issued Oct. 2, 2012; and/or U.S. Pub. No. 2014/0039343, entitled "Biopsy System," published Feb. 6, 2014, the disclosure of which is incorporated by reference herein. Various other suitable ways in which user interface feature (1752) may be configured and operable will be apparent to those of ordinary skill in the art in view of the teachings herein.

Holster (1700) of the present example further includes a tube set (1714) and a cable assembly (1780). Tube set (1714) comprises one or more tubes that communicate vacuum, saline, and/or atmospheric air to probe portion (1710). Cable assembly (1780) comprises a mechanical cable subassembly (1782) and an electrical cable subassembly (1786). Mechanical cable subassembly (1782) comprises one or more rotary drive cables contained within a sheath (1784) as described above and as described in one or more references cited herein. It should therefore be understood that the one or more rotary drive cables provide mechanical power sufficient to drive a cutter relative to needle assembly (1720) to sever tissue samples. Electrical cable subassembly (1786) comprises one or more electrical wires contained within a sheath (1788) as described above and as described in one or more references cited herein. It should therefore be understood that the one or more electrical wires provide electrical communication between holster (1700), particularly user interface feature (1752), and control module (3300). Various suitable ways in which cable assembly (1780) may be configured and operable will be apparent to those of ordinary skill in the art in view of the teachings herein.

Figure 59:
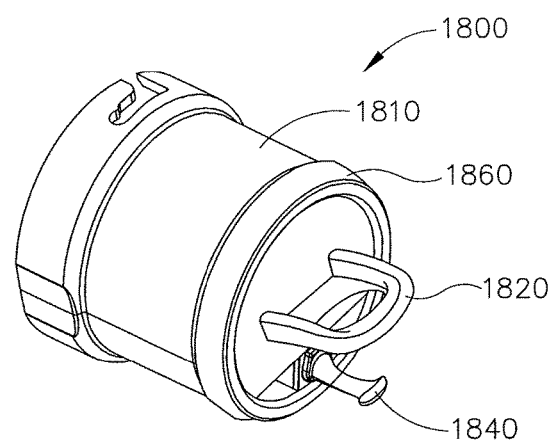
FIG. 59 depicts a perspective view of an exemplary alternative tissue sample holder that may be readily incorporated into the biopsy device of FIG. 57.

FIG. 59 shows an exemplary alternative tissue sample holder (1800) that may be readily incorporated into biopsy device (1700) in place of tissue sample holder (1760). Tissue sample holder (1800) of this example comprises an outer cover (1810), a tissue receiving tray (1820), a plug (1840), and an inner member (not shown) that supports tray (1820) and plug (1840). Outer cover (1810) is transparent in the present example, though this is merely optional. The inner member is rotatable within cover (1810), such that the inner member may be rotated relative to housing (1712) while cover (1810) remains stationary relative to housing (1712). The inner member may thus be rotated to selectively index tray (1820) and plug (1840) relative to the longitudinal axis of needle assembly (1720). When tray (1820) is aligned with the longitudinal axis of needle assembly (1720), tray (1820) is configured to receive tissue samples severed by a cutter (not shown) that moves relative to the needle assembly (1720) in accordance with the teachings of various references cited herein. When plug (1840) is aligned with the longitudinal axis of needle assembly, plug (1840) may be removed to enable insertion of a biopsy site marker applier to deploy a biopsy marker through needle assembly (1720) in accordance with the teachings of various references cited herein.

Tissue sample holder assembly (1800) of the present example further comprises a gripping ring (1860). Gripping ring (1860) of this example is identical to gripping ring (1570) described above, such that the details will not be repeated here. Of course, gripping ring (1860) may have any other suitable configuration.

In addition to the foregoing, and by way of example only, at least part of tissue sample holder assembly (1800) may be configured and operable in accordance with at least some of the teachings of U.S. patent application Ser. No. 14/469,761, entitled "Tissue Collection Assembly for Biopsy Device,"

filed Aug. 27, 2014, the disclosure of which is incorporated by reference herein; and/or any other reference that is cited herein. While tissue sample holder assembly (1800) is described herein in the context of biopsy device (1700), it should be understood that tissue sample holder assembly (1800) may also be used with biopsy device (1500) and various other kinds of biopsy devices, including but not limited to various biopsy devices described in various references cited herein.

As similarly described above with respect to biopsy device (1000), in some examples control module (3300) (as shown in FIG. 53) is configured for use with biopsy device (1700). As described above, control module (3300) comprises cable interface (3320), and tube set interface (3330). Cable interface (3320) is configured to couple with cable assembly (1780). Likewise, tube set interface (3330) is configured to couple with tube set (1714) and is operable to provide communication of vacuum, saline, and/or atmospheric air to probe portion (1710) via tubes (1714). It should be understood that while biopsy device (1500) is described herein as being usable with control module (3300), in other examples biopsy device (1700) may alternatively be usable with any other control module described herein.

D. Exemplary Biopsy System with Side Rotation Knobs

Figure 60:
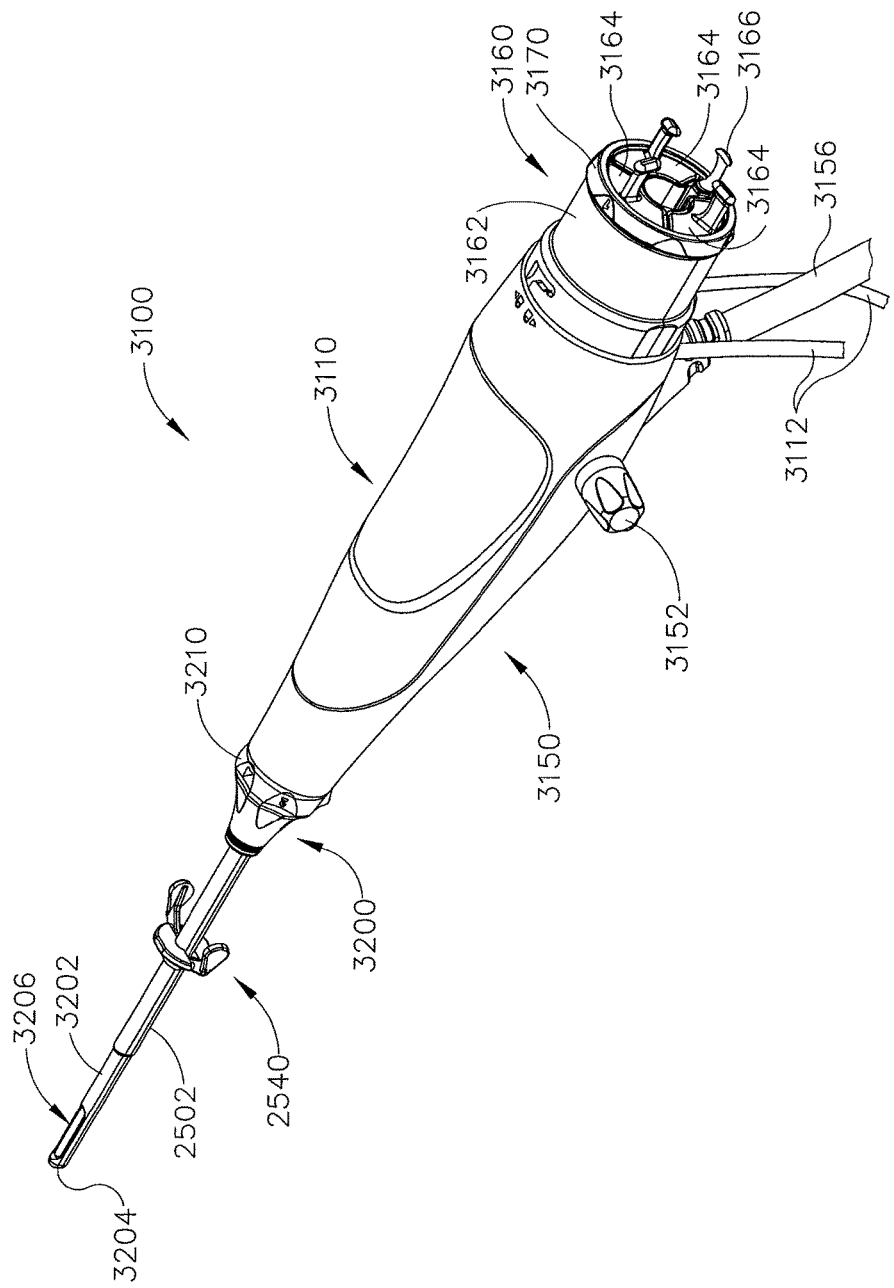
FIG. 60 depicts a perspective view of yet another exemplary alternative biopsy device combined with the targeting cannula of FIG. 18.

FIG. 60 shows a combination of yet another exemplary biopsy device (3100) with targeting cannula (2502) of FIG. 18. Biopsy device (3100) of this example is substantially similar to biopsy device (14). In particular, biopsy device (3100) comprises a probe portion (3110) and a holster portion (3150). Probe portion (3110) includes a distally projecting needle assembly (3200), which is rotatable relative to the remainder of probe portion (3110) about the longitudinal axis defined by needle assembly (3200). As shown in FIG. 60, needle assembly (3200) comprises an elongate cannula (3202) with a blunt distal tip (3204) and a lateral, tissue receiving aperture (3206) formed proximal to tip (3204). Needle assembly (3200) further includes a hub (3210), which is located a the proximal end of cannula (3202) and is configured to enable an operator to grasp and rotate needle assembly (3200) about the longitudinal axis of needle assembly (3200), relative to the rest of probe portion (3110). Hub (3210) is configured substantially similar to index bezel (2530), such that hub (3210) complements hub (2504) of targeting cannula (2502). In particular, hub (3210) includes distally projecting protrusions (not shown) that are configured to snap into corresponding retention features (2518) of hub (2504). Thus, cannula (3202) of needle assembly (3200) may be inserted into cannula (2502); and the protrusions may cooperate with retention features (2518) to secure needle assembly (3200) with cannula (2502).

Probe portion (3110) of the present example also includes a set of tubes (3112) that are configured to provide fluid communication between probe portion (3110) and a control module (3300) (as shown in FIG. 53). Such fluid communication may be provided in accordance with the teachings of any of the references cited herein. By way of example only, control module (3300) may provide vacuum, saline, and/or atmospheric air to probe portion (3110) via tubes (3112). In addition or in the alternative, control module (3300) may receive bodily fluids, saline, and/or atmospheric air from probe portion (3110) via tubes (3112).

Holster portion (3150) of the present example includes a pair of rotation knobs (3152) oriented on the side of holster portion (3150). Rotation knobs (3152) are operatively coupled to needle assembly (3200) such that rotation of any one rotation knob (3152) results in rotation of needle assembly (3200). Although not shown, it should be understood that holster portion (3150) may contain any suitable drive mechanism operable to couple rotation knobs (3152) to needle assembly (3200). Such drive mechanisms for coupling rotation knobs (3152) to needle assembly (3200) may constructed and operable be in accordance with the teachings of various references cited herein.

A cable assembly (3156) also extends from holster portion (3150) and couples holster portion (3150) with control module (3300). Cable assembly (3156) includes one or more rotary drive cables (not shown) that is/are contained within an outer sheath of cable assembly (3156). Such rotary drive cable(s) provide rotary power to actuate a cutter (not shown) of biopsy device (3100) in accordance with the teachings of various references cited herein. One or more electrical cables (not shown) is/are also contained within cable assembly (3156). Such electrical cable(s) is/are in communication with an electrical cable of control module (3300), thereby enabling electrical communication between biopsy device (3100) and control module (3300).

Biopsy device (3100) of the present example further includes a tissue sample holder assembly (3160) located at the proximal end of probe portion (3110). Tissue sample holder assembly (3160) comprises an outer cover (3162), a plurality of tissue receiving trays (3164), a plug (3166), and an inner member (not shown) that supports trays (3164) and plug (3166). Outer cover (3162) is transparent in the present example, though this is merely optional. The inner member is rotatable within cover (3162), such that the inner member may be rotated relative to probe portion (3110) while cover (3162) remains stationary relative to probe portion (3110). The inner member may thus be rotated to selectively index trays (3164) and plug (3166) relative to the longitudinal axis of needle assembly (3200). When a tray (3164) is aligned with the longitudinal axis of needle assembly (3200), that tray is configured to receive tissue samples severed by a cutter (not shown) that moves relative to the needle assembly (3200) in accordance with the teachings of various references cited herein. When plug (3166) is aligned with the longitudinal axis of needle assembly, plug (3166) may be removed to enable insertion of a biopsy site marker applier to deploy a biopsy marker through needle assembly (3200) in accordance with the teachings of various references cited herein.

By way of example only, at least part of tissue sample holder assembly (3160) may be configured and operable in accordance with at least some of the teachings of U.S. Pat. Pub. No. 2008/0214955, entitled "Presentation of Biopsy Sample by Biopsy Device," published Sep. 4, 2008, the disclosure of which is incorporated by reference herein; U.S. Pat. No. 8,702,623, entitled "Biopsy Device with Discrete Tissue Chambers," issued Apr. 22, 2014, the disclosure of which is incorporated by reference herein; U.S. Pat. Pub. No. 2013/0041256, entitled "Access Chamber and Markers for Biopsy Device," published Feb. 14, 2013, the disclosure of which is incorporated by reference herein; U.S. Pub. No. 2014/0039343, entitled "Biopsy System," published Feb. 6, 2014, the disclosure of which is incorporated by reference herein; U.S. patent application Ser. No. 14/469,761, entitled "Tissue Collection Assembly for Biopsy Device," filed Aug. 27, 2014, the disclosure of which is incorporated by reference herein; and/or any other reference that is cited herein.

Tissue sample holder assembly (3160) of the present example further includes a gripping ring (3170). Gripping ring (3170) is secured to the proximal end of the inner member and is rotatable relative to probe portion (3110) and outer cover (3162). Gripping ring (3170) is configured to enable an operator to grasp gripping ring (3170) and thereby rotate the inner member of tissue sample holder assembly (3160) to selectively index trays (3164) and plug (3166) relative to the longitudinal axis of needle assembly (3200). Gripping ring (3170) may comprise an elastomeric material, ridges, knurling, bumps, dimples, and/or any other suitable features or combination of features that may promote an operator to grasp and manipulate gripping ring (3170). Furthermore, in some examples gripping ring (3170) may include detents or other features configured to provide audible and/or tactile feedback to a user. Such features may provide a user with an indication of when trays (3164) and plug (3166) are properly indexed with needle assembly (3200).

As similarly described above with respect to biopsy device (1000), in some examples control module (3300) (as shown in FIG. 53) is configured for use with biopsy device (3100). As described above, control module (3300) comprises cable interface (3320), and tube set interface (3330). Cable interface (3320) is configured to couple with cable assembly (3156). Likewise, tube set interface (3330) is configured to couple with tube set (3112) and is operable to provide communication of vacuum, saline, and/or atmospheric air to probe portion (3110) via tubes (3112). It should be understood that while biopsy device (3100) is described herein as being usable with control module (3300), in other examples biopsy device (3100) may alternatively be usable with any other control module described herein.

Figure 61:
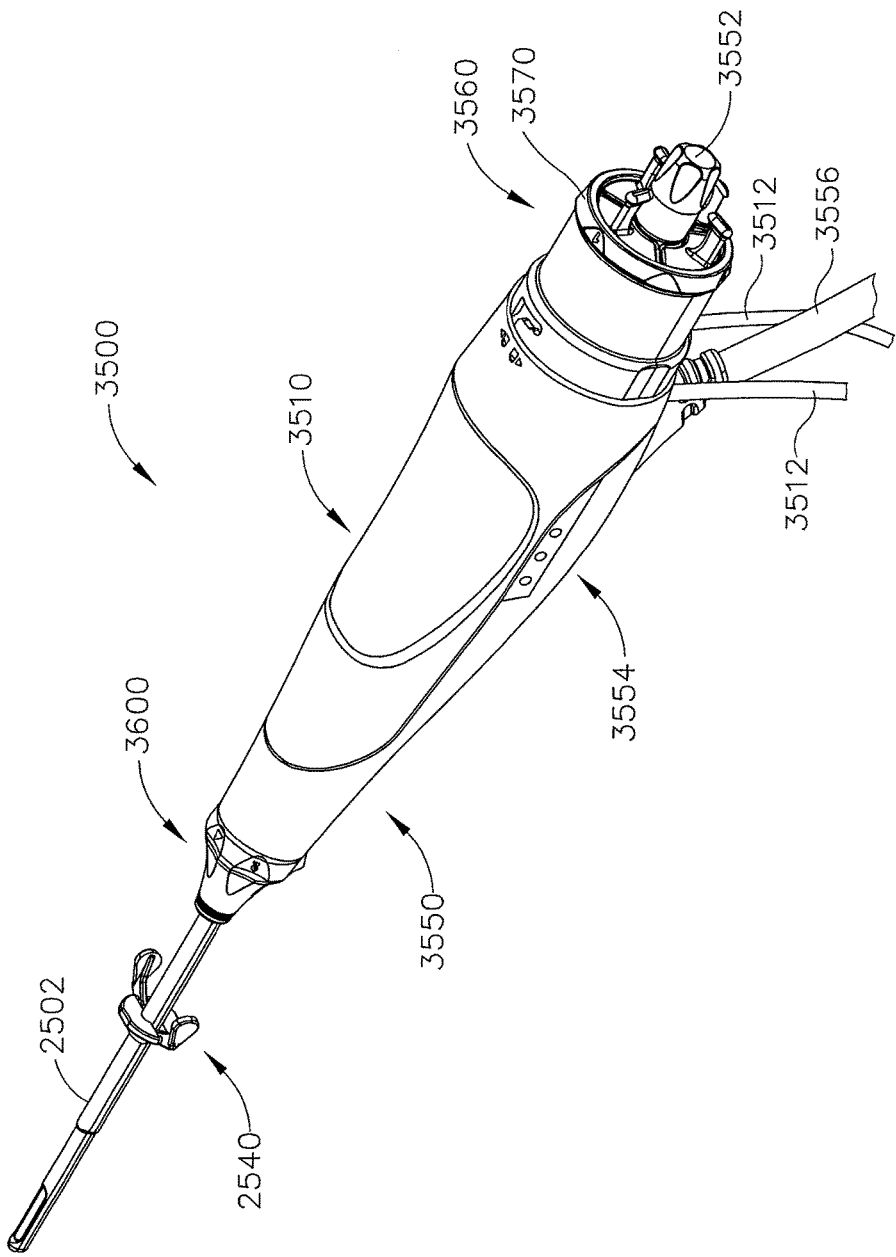
FIG. 61 depicts a perspective view of yet another exemplary alternative biopsy device combined with the targeting cannula of FIG. 18.

E. Exemplary Biopsy System with Proximal Rotation Knob and Light Emitting Indicators FIG. 61 shows a combination of yet another exemplary biopsy device (3500) with targeting cannula (2502) of FIG. 18. Biopsy device (3500) of this example is substantially similar to biopsy devices (14, 3100). In particular, biopsy device (3500) comprises a probe portion (3510) and a holster portion (3550). Probe portion (3510) of this example is identical to probe portion (3110) described above, such that the details of probe portion (3510) will not be repeated here.

Holster portion (3550) is identical to holster portion (3150) described above, except that holster portion (3550) of this example includes a rotation knob (3552) extending proximally from a tissue sample holder assembly (3560). In particular, tissue sample holder assembly (3560) is substantially the same as tissue sample holder assembly (3160) described above, except rotation knob (3552) extends proximally from an inner member (not shown). With rotation knob (3552) extending proximally from tissue holder assembly (3560), a user may rotate needle assembly (3600) or index tissue sample holder assembly (3560) (via a gripping ring (3570), similarly as described above with respect to gripping ring (3170)) without substantially changing the position of the user's hand. Rotation knob (3552) is similar to rotation knobs (3152) described above in that rotation knob (3552) is operatively coupled to a needle assembly (3600) of biopsy device (3500) to selectively rotate needle assembly (3600) about the longitudinal axis of needle assembly (3600). It should be understood that while rotation knob (3552) is integrated into tissue holder assembly (3560), rotation knob (3552) remains independently rotatable relative to tissue sample holder assembly (3560). Like with rotation knobs (3152) described above, rotation knob (3552) may be coupled to suitable drive mechanisms that may be constructed and operable in accordance with the teachings of various references cited herein.

Holster portion (3550) also includes a plurality of light emitting indicators (3554). Light emitting indicators (3554) are similar in function to light emitting indicators (3354) of footswitch assembly (3350) described above. Light emitters (3554) may thus be configured to indicate basic information regarding biopsy device (3700) to a user. For instance, in some examples light emitters (3554) may be color coded to indicate an error condition (red), a warning condition (yellow), and a ready condition (green). Where biopsy device (3500) is used with control module (3300) and footswitch assembly (3350) described above, light emitters (3554) and light emitters (3354) may be coordinated such that they display the same information to a user.

Biopsy device (3500) may be coupled with a control module similar control module (3300) described above with respect to FIGS. 53 and 54. The control module may connect to biopsy device (3500) via cable assembly (3556) and tubes (3512) similarly to cable assembly (3156) and tubes (3112) described above. While the control module of this example is identical to control module (3300) described above, such that overlapping details of control module will not be repeated here, it should be understood that biopsy device (3500) may be readily configured for use with any other control module described herein.

Figure 62:
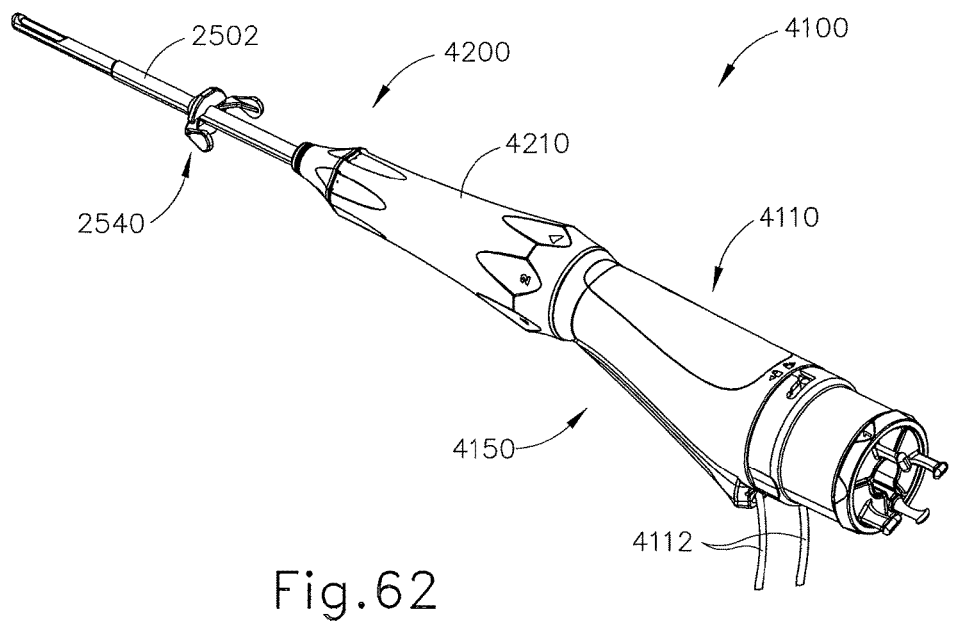
FIG. 62 depicts a perspective view of yet another exemplary alternative biopsy device combined with the targeting cannula of FIG. 18.
Figure 63:
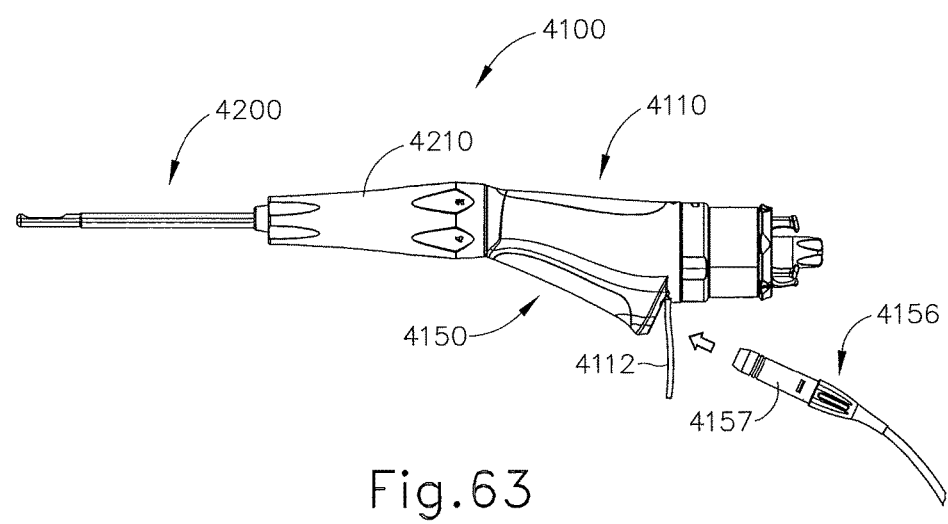
FIG. 63 depicts a side elevational view of the biopsy device of FIG. 62.

F. Exemplary Biopsy System with Quick Connect Cable Assembly and Elongated Indexing Bezel FIGS. 62-63 show a combination of yet another exemplary biopsy device (4100) with targeting cannula (2502) of FIG. 18. Biopsy device (4100) of this example is substantially similar to biopsy devices (14, 3100, 3500) described above. In particular, biopsy device (4100) comprises a probe portion (4110) and a holster portion (4150). Probe portion (4110) of this example is substantially similar to probe portion (3110) described above, such that the details of probe portion (4110) will not be repeated here.

Holster portion (4150) is identical to holster portion (3150) described above, except that holster portion (4150) of this example omits a rotation knob similar to rotation knob (3152). Instead, a needle assembly (4200) of biopsy device (4100) may simply be rotated via index bezel (4210) of needle assembly (4200). Index bezel (4210) is similar to index bezel (3110) described above, except index bezel (4210) is elongated to enhance a user's grip on index bezel (4210) and to facilitate grasping of index bezel (4210) from a location proximal to biopsy device (4100). In particular, index bezel (4210) extends proximally from needle assembly (4200) for a substantial length of holster portion (4150). It should be understood that although index bezel (4210) of the present example is characterized as being a component of holster portion (4150), no such limitation is intended. For instance, in other examples index bezel (4210) is alternatively part of probe portion (4110).

As can best be seen in FIG. 63, holster portion (4150) also includes a quick connect cable assembly (4156). Cable assembly (4156) is similar to cable assembly (3156) described above in that cable assembly (4156) includes a rotary cable that is operable to drive a cutter (not shown) to sever a tissue sample. Cable assembly (4156) also includes a quick connect connector (4157), which may be inserted into holster portion (4150). Connector (4157) may permit a user to quickly connect and disconnect biopsy device (4150) to a control module that is substantially similar to control module (3300) described above with respect to FIG. 53. Connector (4157) is operable to quickly couple and decouple the rotary drive cable of cable assembly (4156) with the cutter drive assembly of biopsy device (4100) as connector (4157) is coupled with and decoupled from holster portion (4150).

Biopsy device (4100) may be coupled with a control module similar to control module (3300) described above with respect to FIGS. 53-54. The control module (3300) may connect to biopsy device (4100) via cable assembly (4156) and tubes (4112) similarly to cable assembly (3156) and tubes (3112) described above. While the control module of this example is identical to control module (3300) described above, such that overlapping details of control module will not be repeated here, it should be understood that biopsy device (3500) may be readily configured for use with any other control module described herein.

G. Exemplary Control Module with Cable Management System

Figure 64:
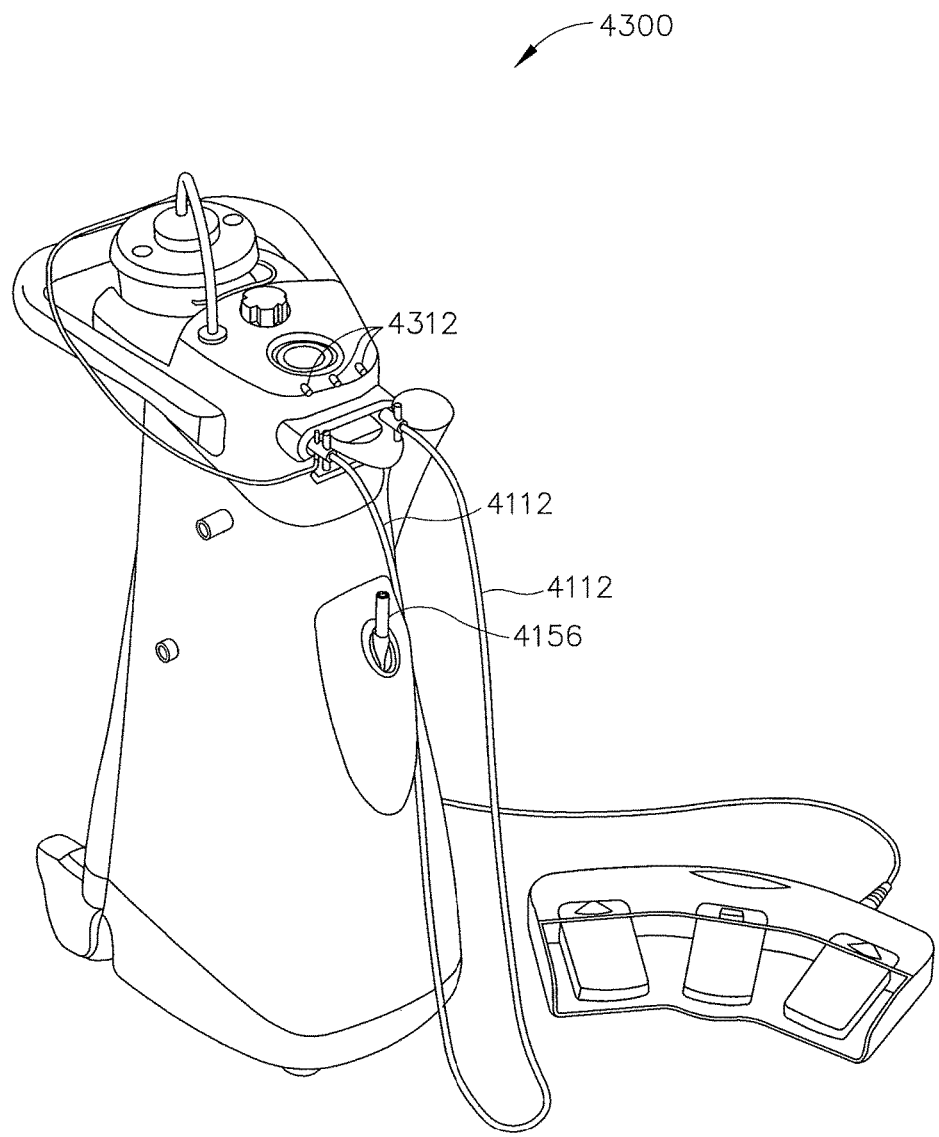
FIG. 64 depicts a perspective view of another exemplary alternative control module for use with the biopsy system of FIG. 1.

FIGS. 64-49 show an exemplary alternative control module (4300) that is usable in conjunction with biopsy device (4100) described above. Although control module (4300) is described herein as being usable with biopsy device (4100), it should be understood that in other examples control module (4300) is readily usable with any other biopsy device described herein. Control module (4300) is substantially similar to control module (3300) described above. However, unlike control module (3300), control module (4300) of this example includes a plurality of light emitting indicators (4312). Light emitting indicators (4312) may be similar to other light emitting indicators (3354, 3752) described herein. For instance, light emitting indicators (4312) may be color coded to convey status information about the biopsy device (4500) to an operator.

Figure 65:
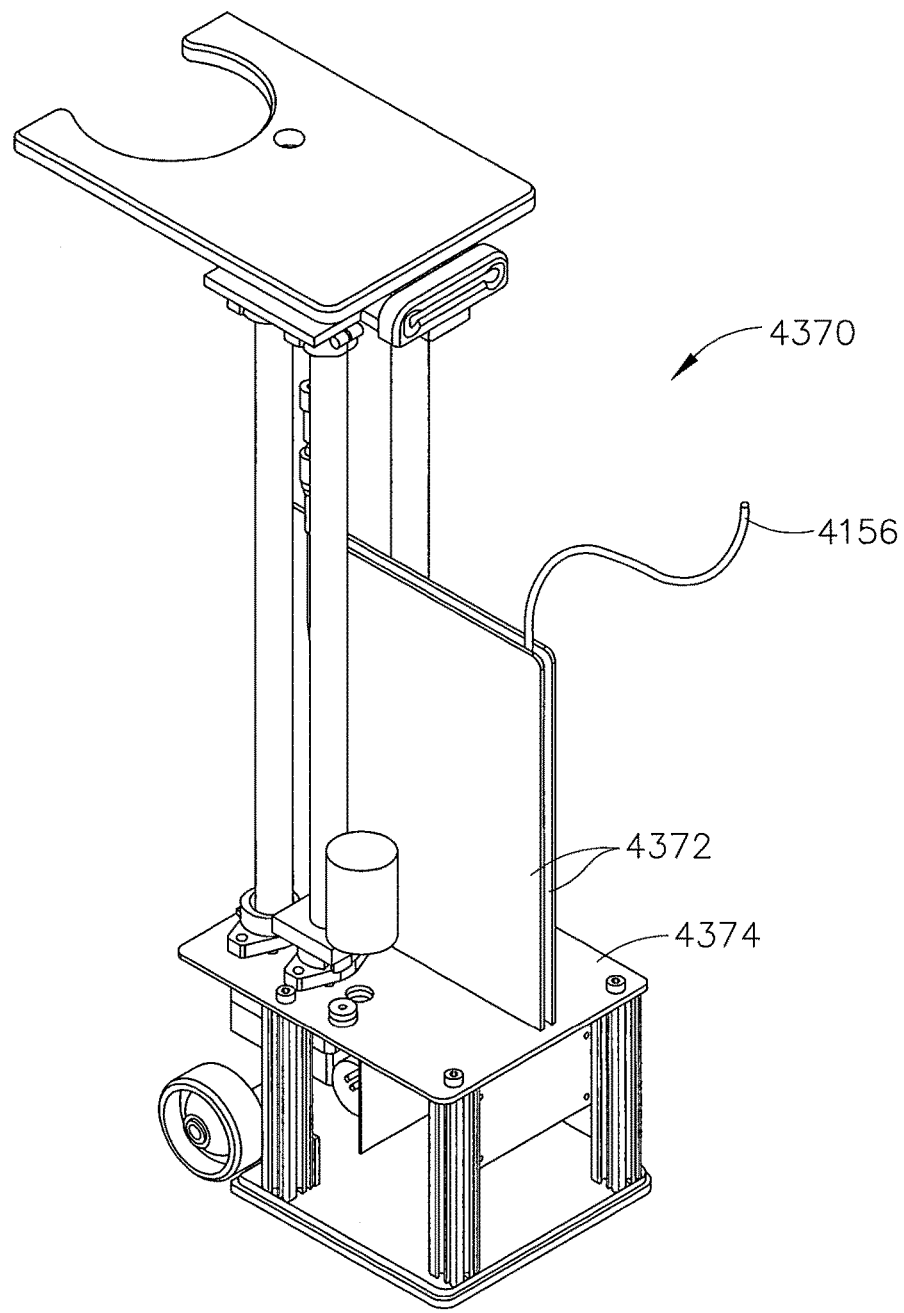
FIG. 65 depicts a perspective view of a cable management system of the control module of FIG. 64.
Figure 66:
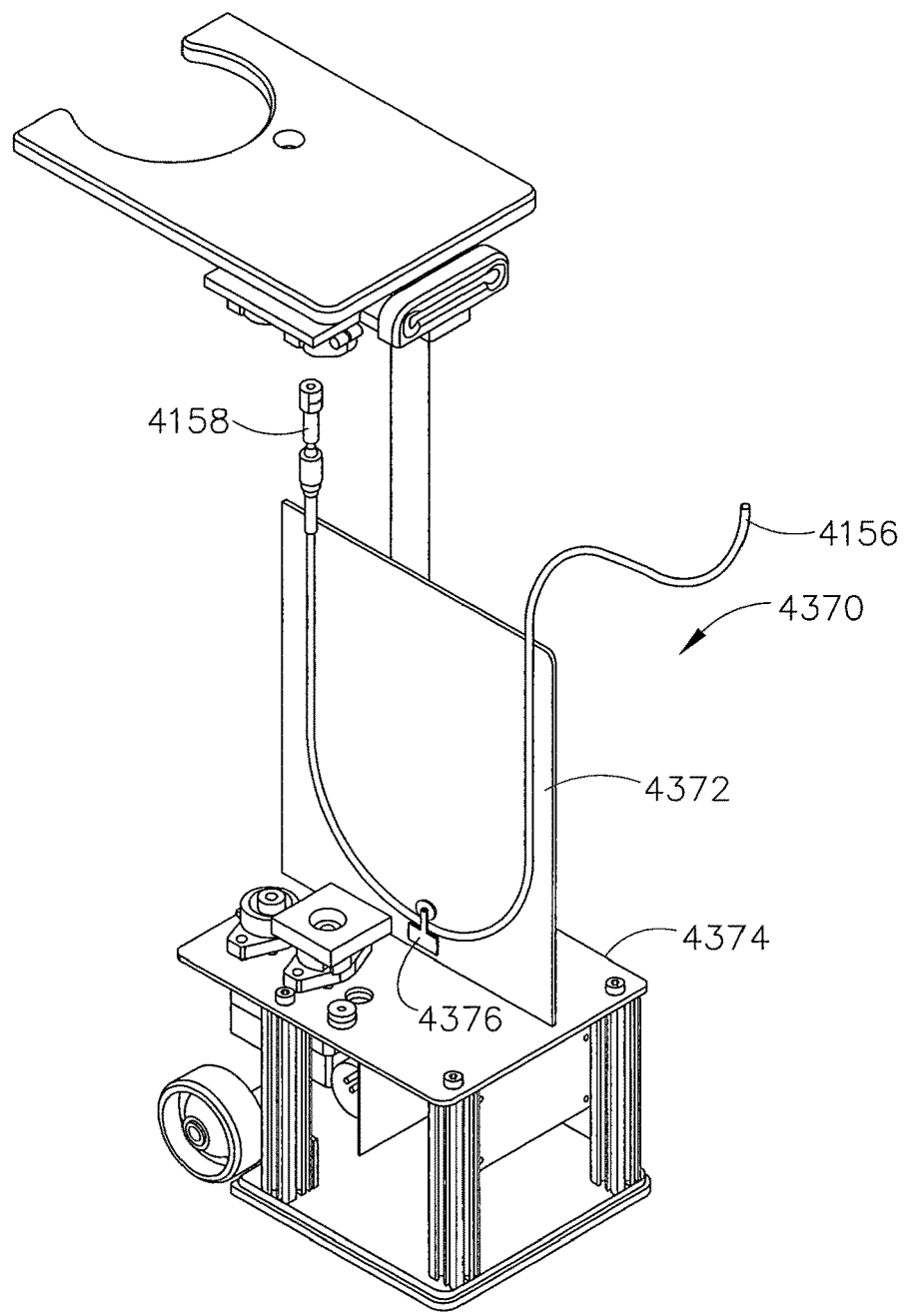
FIG. 66 depicts another perspective view of the cable management system of FIG. 65, with certain features omitted to reveal internal structures, and with a cable assembly in a retracted position.
Figure 67:
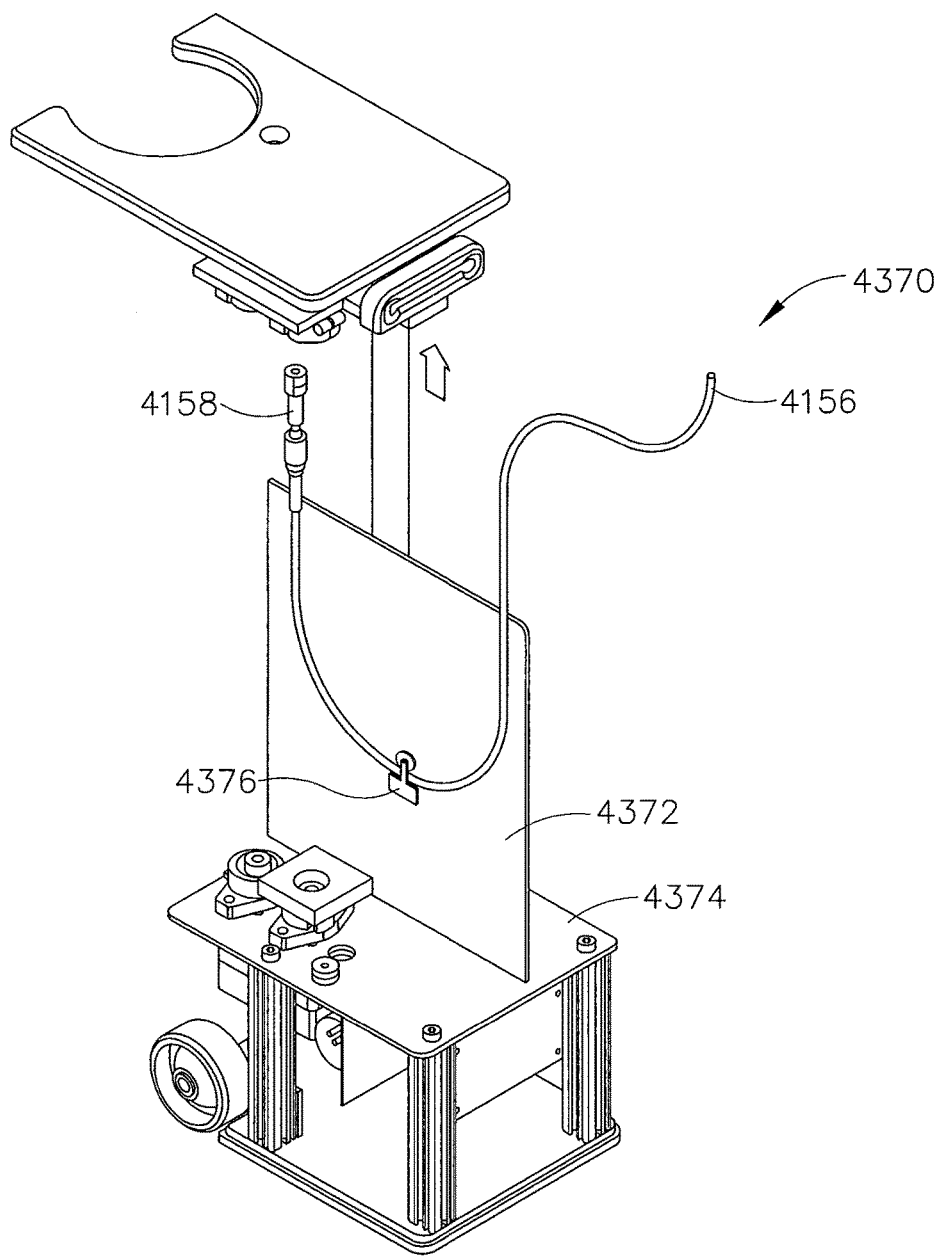
FIG. 67 depicts still another perspective view of the cable management system of FIG. 65, with certain features omitted to reveal internal structures, and with the cable assembly in an extended position.

Control module (4300) of this example also includes a cable management system (4370), which may be used to manage cable assembly (4156). As can be seen in FIG. 64, cable assembly (4156) is retracted into control module (4300). FIGS. 65-67 show the internal components of control module (4300) to reveal cable management system (4370). Cable management system (4370) comprises two plates (4372) that are fixed to a base (4374) of control module (4300). Plates (4372) are spaced from each other a distance configured to permit cable assembly (4156) to move freely in between plates (4372) along a vertical plane. However, plates (4372) are spaced at a distance that is configured to laterally maintain positioning of cable assembly (4156) in between plates (4372). Thus, plates (4732) maintain cable assembly (4156) within a relatively consistent vertical plane. In some instances, in the absence of features such as plates (4372), cable assembly (4156) may have a tendency to move torsionally with a whipping effect when the internal drive cable is actuated to rotate. Plates (4372) may thus contain cable assembly (4156) to prevent this torsional whipping motion.

As can best be seen in FIG. 66, cable management system (4370) may also include a weight (4376). Weight (4376) is configured to be slidable relative to cable assembly (4156) such that as cable assembly (4156) is pulled from cable management system (4370), weight (4376) slides along the length of cable assembly (4156). Weight (4376) may thus maintain tension in cable assembly (4156) and thereby facilitate retraction of cable assembly (4156) into control module (4300) at the end of a biopsy procedure.

An exemplary use of cable management system (4370) can be seen by comparing FIGS. 66 and 67. In use, a control module attachment portion (4158) of cable assembly (4156) is fixed in a constant position within control module (4300), while the connector (4157) of cable assembly (4156) remains free to be pulled from cable management system (4370). When cable assembly (4156) is retracted into cable management system (4370), weight (4736) is operable to pull cable assembly (4156) downwardly toward base (4374).

As cable assembly (4156) is pulled from cable management system (4370) (toward the position shown in FIG. 67), weight (4376) slides proximally along cable assembly (4156) while maintaining tension in cable assembly (4156). If a rotary drive cable in cable assembly (4156) is actuated to rotate, plates (4372) may contain any whipping by maintaining cable assembly (4156) between plates (4372).

H. Exemplary Control Module with Reduced Footprint

Figure 68:
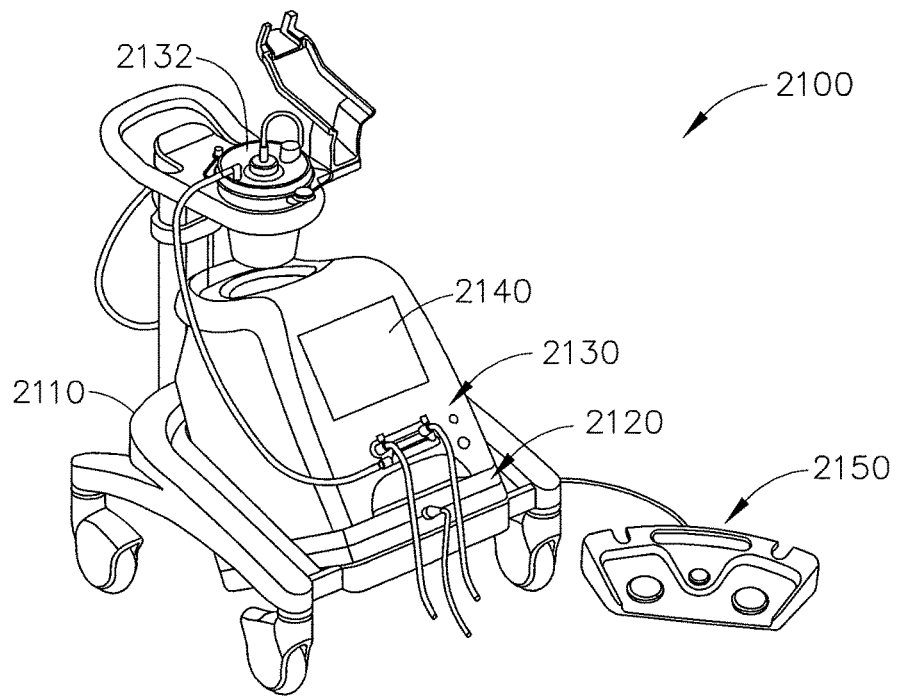
FIG. 68 depicts a perspective view of still another exemplary alternative control module for use with the biopsy system of FIG. 1.

FIG. 68 shows an exemplary alternative control module (2100) that may be used in place of any of the control modules (12, 1200, 1400, 1600, 1900) described herein. Control module (2100) may thus be used with any of the various biopsy devices described herein, among other biopsy devices. Control module (2100) of this example comprises a floor cart (2110), a cable interface (2120), a tube set interface (2130), a display screen (2140), and a footswitch assembly (2150). Cable interface (2120) is configured to couple with any of the various cable assemblies described herein. Various suitable ways in which cable interface (2120) may be configured will be apparent to those of ordinary skill in the art in view of the teachings herein.

Tube set interface (2130) is configured to couple with any of the various tube assemblies described herein; and is operable to provide communication of vacuum, saline, and/or atmospheric air via tubes that are coupled therewith. Tube set interface (2130) is further in communication with a vacuum canister (2132), which is seated in control module (2100). By way of example only, tube set interface (2130) may be configured and operable in accordance with at least some of the teachings of U.S. Pat. No. 6,162,187, entitled "Fluid Collection Apparatus for a Surgical Device," published Dec. 19, 2000, the disclosure of which is incorporated by reference herein. In some other versions, tube set interface (2130) is configured and operable in accordance with at least some of the teachings of U.S. Pub. No. 2013/0218047, entitled "Biopsy Device Valve Assembly," published Aug. 22, 2013, the disclosure of which is incorporated by reference herein. Other suitable ways in which tube set interface (2130) may be configured an operable will be apparent to those of ordinary skill in the art in view of the teachings herein.

Display screen (2140) is configured to provide a graphical user interface for the operator. By way of example only, display screen may display information relating to operation of an associated biopsy device in accordance with the teachings of any of the various references cited herein. In some versions, display screen (2140) comprises a touch screen that is operable to directly receive user input from the operator. By way of example only, display screen (2140) may provide displays and operability in accordance with at least some of the teachings of U.S. Pub. No. 2014/0039343, entitled "Biopsy System," published Feb. 6, 2014, the disclosure of which is incorporated by reference herein.

Footswitch assembly (2150) includes a plurality of footswitches that enable an operator to control operation of an associated biopsy device in a hands-free fashion. In particular, footswitch assembly (2150) includes a plurality of switches that the operator may actuate by stepping on the switches. By way of example only, footswitch assembly (2150) may be configured and operable in accordance with the teachings of U.S. Pub. No. 2014/0039343, entitled "Biopsy System," published Feb. 6, 2014, the disclosure of which is incorporated by reference herein. Other suitable ways in which footswitch assembly (2150) may be configured and operable will be apparent to those of ordinary skill in the art in view of the teachings herein. It should also be understood that all other features of control module (2100)

may be configured and operable in accordance with the teachings of U.S. Pub. No. 2014/0039343, entitled "Biopsy System," published Feb. 6, 2014, the disclosure of which is incorporated by reference herein; and/or any other reference cited herein.

I. Exemplary Control Module with Operator Seat

Figure 69:
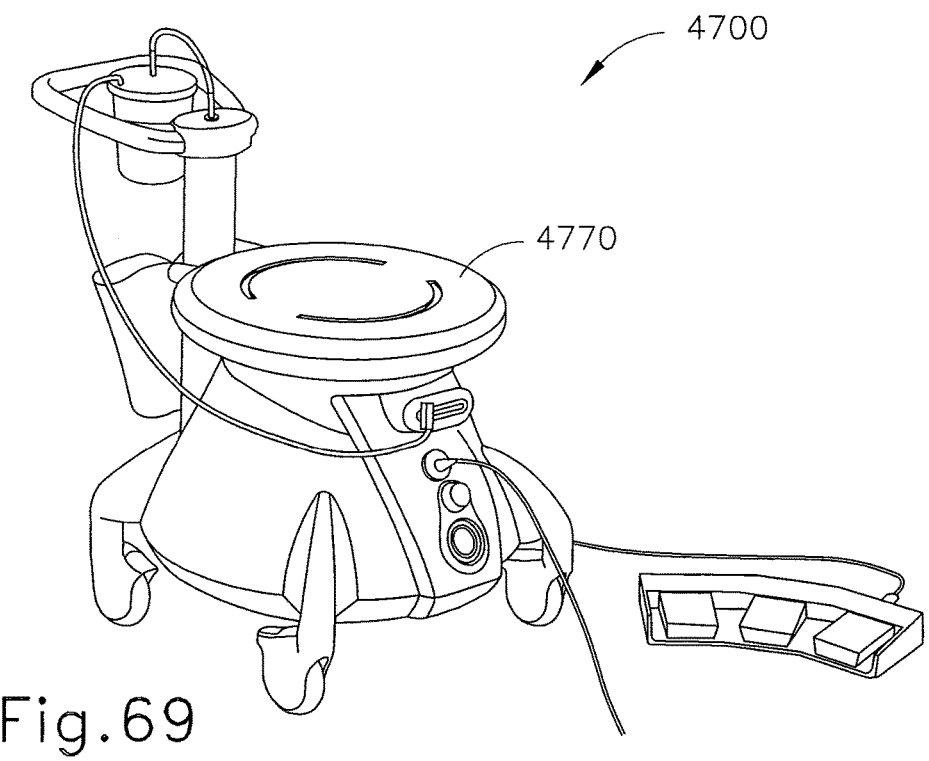
FIG. 69 depicts a perspective view of yet another exemplary alternative control module for use with the biopsy system of FIG. 1.

FIG. 69 shows yet another exemplary alternative control module (4700) that may be used in conjunction with any of the biopsy devices described herein. Control module (4700) is substantially similar to control module (3300) described above, such that overlapping details of control module (4700) will not be repeated here. Moreover, it should be understood that control module (4700) may incorporate any devices or features described above with respect to any control module described herein that are not shown in FIG. 69.

Unlike control module (3300), control module (4700) of this example includes a smaller profile which supports a stool member (4770). Stool member (4770) is configured to allow a user to sit on control module (4700) while performing a biopsy procedure. Additionally, control module (4700) includes two light emitting indicators (4712) near the port for cable assembly (4156). Light emitting indicators (4712) may be similar to other light emitting indicators (3354, 3752, 4312) described herein. For instance, light emitting indicators (4712) may be color coded to convey status information about the biopsy device (4500) to a user.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy system, comprising: (a) a biopsy device; (b) a localization assembly, wherein the localization assembly is configured to orient the biopsy device relative to a patient; and (c) a control module, wherein the control module is communication with the biopsy device, wherein the control module is configured to operate a plurality of functional features of the biopsy device, wherein the control module comprises a cable and a cable management assembly, wherein the cable management assembly comprises: (i) a pair of cable management plates, wherein each the pair cable management plates are disposed substantially parallel to each other, wherein the plates define a space therebetween, and (ii) a weight, wherein the weight is configured to move within the space defined by the pair of cable management plates, wherein the weight is attachable to the cable of the control module, wherein the weight is further configured to slide axially along the cable.

Example 2

The biopsy system of Example 1, wherein the control module further comprises a plurality of indicators, wherein each indicator configured to correspond to a particular functional feature of the plurality of functional features of the biopsy device.

Example 3

The biopsy system of Example 2, wherein the plurality of indicators comprises a plurality of color coded light emitters.

Example 4

The biopsy system of Example 3, wherein the plurality of color coded light emitters comprises a plurality of LEDs.

Example 5

The biopsy system of any one or more of Examples 1 through 4, wherein the weight of the cable management assembly comprises a wheel, wherein the wheel is configured to permit axial sliding of the weight along the cable.

Example 6

The biopsy system of any one or more of Examples 1 through 5, wherein the cable is a rotary cable.

Example 7

The biopsy system of Example 6, wherein the pair of cable management plates are spaced from each other to contain transverse movement of the cable, yet permit axial movement.

Example 8

The biopsy system of any one or more of Examples 1 through 6, wherein the weight comprises a mass, wherein the mass is configured to pull the cable downwardly relative to the pair of cable management plates.

Example 9

The biopsy system of Example 8, wherein the mass is further configured to permit an operator to pull the cable upwardly relative to the pair of cable management plates.

Example 10

The biopsy system of any one or more of Examples 1 through 9, wherein the biopsy device comprises: (i) a body, (ii) a needle extending distally from the body, the needle comprising a lateral aperture, and (iii) a cutter, wherein the cutter is movable relative to the needle to sever a tissue sample extending through the lateral aperture of the needle, wherein the cable of the control module is configured to selectively couple to the body of the biopsy device, wherein the control module is configured to communicate energy to the biopsy device to control movement of the cutter.

Example 11

The biopsy system of Example 10, wherein the cable is configured to communicate mechanical energy to the biopsy device to control movement of the cutter.

Example 12

The biopsy system of Example 11, wherein the biopsy device further comprises a cutter drive mechanism disposed in the body.

Example 13

The biopsy system of Example 12, wherein the cutter drive mechanism is operable to convert rotational mechanical energy from the cable to translation and rotation of the cutter.

Example 14

The biopsy system of Example 1, wherein the cable management assembly is configured to retract the cable into the control module.

Example 15

The biopsy system of Example 1, wherein the cable management assembly is operable to permit a user to selectively remove a length of the cable from the control module, wherein the length is configured for the performance of a biopsy procedure by the operator.

Example 16

A control module for use with a biopsy device, the control module comprising: (a) an outer housing; (b) an operator interface, wherein the operator interface is configured to receive operator inputs to control at least one functional feature of a biopsy device; and (c) a cable management assembly, wherein the cable management assembly comprises: (i) a cable, (ii) a pair of plates, wherein the pair of plates are positioned relative to each other to define a cableway, wherein the cableway is configured to movably receive at least a portion of the cable, wherein the cableway is configured to restrict transverse movement of the cable, and (iii) a cable puller, wherein the cable puller is configured to releasably retract the cable within the cable management assembly.

Example 17

The control module of Example 16, wherein the cable management assembly is disposed within the outer housing of the control module such that the cable management assembly is configured to releasably retract the cable within the outer housing of the control module.

Example 18

The control module of Example 17, wherein the outer housing comprises a cable opening, wherein at least a portion of the cable extends through the cable opening, wherein the cable management assembly is configured to permit an operator to selectively pull a procedure length of the cable through the opening of the outer housing.

Example 19

The control module of Example 16, wherein the cable comprises a rotary cable, wherein the pair of plates are configured to substantially arrest lateral movement of the rotary cable initiated by transfer of rotary motion through the rotary cable.

Example 20

A biopsy system, comprising: (a) a biopsy device, the biopsy device comprising: (i) a body, (ii) a needle extending distally from the body, wherein the needle is comprises a lateral aperture, and (iii) a cutter, wherein the cutter is movable relative to the lateral aperture of the needle to sever a tissue sample; and (b) a cable management assembly associated with the biopsy device, wherein the cable management assembly comprises: (i) a cable, (ii) a cable restrictor, wherein at least a portion of the cable is disposed within the cable restrictor, wherein the cable restrictor is configured to restrict motion of the cable along at least one axis, and (iii) a cable mover, wherein the cable mover is configured to selectably move the cable along at least one axis.

Example 21

A guide device for insertion into an aperture of a grid plate, wherein the guide device is usable with a biopsy device to direct a needle of the biopsy device, the guide device comprising: (a) a body wherein the body comprises a proximal face and a distal face, wherein a guide opening extends through the body from the proximal face to the distal face, wherein the opening defines a guide axis; and (b) a lock member, wherein the lock member is attachable to the body, wherein the lock member is configured to engage with a stop member to prevent movement of the biopsy device along the guide axis.

Example 22

The guide device of Example 21, wherein the body of the guide device comprises at least one resilient feature is configured to engage at least a portion of the grid plate to prevent proximal movement of the guide device when the guide device is inserted into the aperture of the grid plate.

Example 23

The guide device of any one or more of Examples 21 through 22, wherein the body further comprises a protrusion extending proximally from the proximal face of the body, wherein the lock member is configured to selectably attach to the protrusion.

Example 24

The guide device of Example 23, wherein the protrusion further comprises a channel, wherein the lock member comprises a first pair of resilient tabs, wherein the resilient tabs are configured to engage the channel of the protrusion.

Example 25

The guide device of any one or more of Examples 21 through 24, wherein the lock member comprises a second pair of resilient tabs, wherein the second pair of resilient tabs are configured to selectably engage the stop member.

Example 26

The guide device of Example 21, wherein the lock member comprises a lock arm, wherein the lock arm is rotatable relative to the body to selectively engage the stop member.

Example 27

The guide device of Example 26, wherein the lock arm is rotatable between a first position and a second position, wherein the lock arm is configured to secure the stop member to the guide device when the lock arm is in the first position, wherein the lock arm is configured to permit movement of the stop member relative to the guide device when the lock arm is in the second position.

Example 28

The guide device of Example 27, wherein the lock arm comprises a recess, wherein the recess is configured to align with the guide opening of the body when the lock arm is in the first position.

Example 29

A guide device for insertion into an aperture of a grid plate, wherein the guide device is usable with a biopsy device to direct a needle of the biopsy device, the guide device comprising: (a) a body defining a first pair of opposing faces, a second pair of opposing faces, and a third pair of opposing faces, wherein the guide device comprises a first guide opening, a second guide opening, and an integral living hinge, wherein the first guide opening extends through the body between the first pair of opposing faces, wherein the second guide opening extends between the second pair of opposing faces, wherein the living hinge is defined by a recess extending into the body from the at least one face of the first pair of opposing faces or the second pair of opposing faces; (b) an engagement protrusion, wherein the engagement protrusion is associated with the living hinge of the body to resiliently bear against an interior portion of the gird plate when the guide device is inserted into the grid plate; and (c) an arrestor protrusion wherein the arrestor protrusion protrudes outwardly from the body, wherein the arrestor protrusion is configured to arrest distal movement of the guide device when the guide device is inserted into the grid plate.

Example 30

The guide device of Example 29, wherein the living hinge is further defined by at least a portion of the body, wherein the at least a portion of the body defining the living hinge defines a thickness, wherein the thickness is configured to permit the engagement protrusion to resiliently bear against the interior portion of the grid plate when the guide device is inserted into the grid plate.

Example 31

A guide device for insertion into an aperture of a grid plate, wherein the guide device is usable with a biopsy device to direct a needle of the biopsy device, the guide device comprising: (a) a body defining a proximal face and a distal face, wherein the body comprises four guide openings extending proximally though the body from the proximal face to the distal face, wherein each opening of the four openings intersect to define a fifth opening; and (b) an insert member, wherein the insert member comprises a first arm and a second arm, wherein the first arm and the second arm together define an exterior and an interior, wherein exterior is configured to define a diameter corresponding to a diameter defined by at least one of the four guide openings, wherein the interior defines a space configured to receive the needle of the biopsy device, wherein the insert member is configured to be co-axially received within any one of the four guide openings or the fifth guide opening, wherein the insert member is configured to remain co-axially received within any one of the four guide openings or the fifth guide opening when the insert member is rotated relative to the body.

Example 32

The guide device of Example 31, wherein the first arm and second arm of the inset member extend distally from a stop member, wherein the stop member is associated with an introducer cannula, wherein the stop member is configured to selectively grip at least a portion of the introducer cannula.

Example 33

The guide device of Example 31, wherein the body further include a plurality of arrestor protrusions extending outwardly from the proximal face, wherein the arrestor protrusions are configured to engage the grid plate to prevent over insertion of the guide device into the grid plate.

Example 34

A localization system for use with a targeting cannula to orient the targeting cannula relative to a plurality of apertures of the grid plate, wherein the localization system comprises: (a) an adaptor device, wherein the adaptor device comprises a first aperture engagement portion, and a cube window, wherein the first aperture engagement portion comprises at least one resilient member and an actuator, wherein the resilient member is responsive to the actuator to engage an interior of an aperture of the plurality of apertures of the grid plate; and (b) a guide cube, wherein the guide cube is configured to receive the targeting cannula, wherein the guide cube is insertable into the cube window of the adaptor device, wherein the guide cube is further configured to translationally lock relative to the cube window in at least one direction.

Example 35

The localization system of Example 34, wherein the adaptor device and the cube window are oriented along a common longitudinal axis.

Example 36

The localization system of Example 34, wherein the adaptor device is positioned along an adaptor device axis, wherein the cube window is positioned along a cube window axis, wherein the adaptor device axis is perpendicular to the cube window axis.

Example 37

The localization system of Example 34, wherein the actuator of the first aperture engagement portion comprises at least one cam member, wherein the actuator is rotatable to initiate engagement between the actuator and the resilient member.

Example 38

The localization system of Example 34, further comprising a second aperture engagement portion, wherein the second aperture engagement portion comprises a distal protrusion, wherein the distal protrusion corresponds to the shape of at least one aperture of the plurality of apertures of the grid plate.

Example 39

The localization system of Example 38, wherein the second aperture engagement portion is disposed between the first aperture engagement portion and the cube window.

Example 40

A depth stop device for use with a targeting cannula, wherein the depth stop device comprises: (a) a body wherein the body defines an opening, wherein the opening is configured to receive at least a portion of the targeting cannula; and (b) a pair of arms, wherein the arms are secured to the body, wherein each arm of the pair of arms comprises an engagement portion, wherein the engagement portion of each arm extends into the opening defined by the body, wherein the pair of arms are configured to resiliently bear against the targeting cannula when the targeting cannula is inserted into the opening defined by the body, wherein the engagement portions of each of the pair of arms selectively resist translation of the targeting cannula relative to the body when the targeting cannula is inserted into the opening defined by the body.

Example 41

The depth stop device of Example 40, wherein each arm of the pair of arms further comprises a release portion, wherein each release portion is configured to be manipulated by an operator to pivot the respective arm relative to the body to move the respective engagement portion away from the opening defined by the body.

Example 42

The depth stop device of Example 41, further comprising a plurality of resilient members, wherein the plurality of resilient members extend between the pair of arms and the body to pivotably couple the pair of arms to the body.

Example 43

The depth stop device of Example 42, wherein the body, the pair of arms, and the resilient members are formed of a single integral component.

Example 44

A biopsy system, comprising: (a) a biopsy device, the biopsy device comprising: (i) a body, (ii) a needle extending distally from the body, wherein the needle is comprises a lateral aperture, and (iii) a cutter, wherein the cutter is movable relative to the lateral aperture of the needle to sever a tissue sample; (b) a control module, wherein the control module is operable to control at least one functional feature of the biopsy device; (c) an operator input assembly in communication with the control module, wherein the operator input assembly comprises at least one input device, and a cable port; (d) a cable, wherein the cable is selectively attachable to the cable port of the operator input assembly and the body of the biopsy device to permit the biopsy device to communicate with the control module.

Example 45

The biopsy system of Example 44, wherein the operator input assembly comprises a foot pedal.

Example 46

The biopsy system of Example 44, wherein the cable comprises a rotary cable, wherein the operator input assembly comprises a motor to supply a rotary input to the rotary cable.

Example 47

The biopsy system of any one or more of Examples 44 through 46, further comprising a control cable, wherein the control cable is coupled to the control module and the operator input assembly, wherein the control cable defines a first length, wherein the cable comprises a second length, wherein the first length is longer than the second length.

Example 48

The biopsy system of any one or more of Examples 44 through 47, wherein the operator input assembly and the biopsy device are positioned inside an MRI suite, wherein the control module is positioned outside an MRI suite.

Example 49

The biopsy system of any one or more of Example 44 through 48, wherein the operator input assembly is configured to control the at least one functional features of the biopsy device using the control module, remotely from the control module.

IX. Miscellaneous

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system, comprising:
   (a) a biopsy device adapted to be oriented by a localization assembly relative to a patient, wherein the biopsy device includes a cutter for severing a tissue sample from the patient;
   (b) a control unit disposed in a first housing, wherein the control unit is configured to supply vacuum to the biopsy device and operate a plurality of functional features of the biopsy device;
   (c) a remote unit disposed in a second housing and configured to be independently positionable relative to the control unit, wherein the remote unit is separate from, and in communication with the control unit, wherein the remote unit includes a motor; and
   (d) a rotary drive cable coupled to the remote unit to be driven by the motor to control movement of the cutter in the biopsy device.

2. The biopsy system of claim 1, wherein the biopsy system further comprises an electrical cable extending from the control unit to the remote unit, wherein the rotary drive cable extends from the biopsy device to the remote unit, wherein the electrical cable defines a longitudinal length, wherein the longitudinal length is configured to correspond to a distance between a procedure position adjacent to the biopsy device and an external position outside of an MRI suite.

3. The biopsy system of claim 2, wherein the rotary drive cable defines a longitudinal length, wherein the longitudinal length of the rotary drive cable is configured to correspond to a distance between the procedure position and the biopsy device, wherein the longitudinal length of the electrical cable is greater than the longitudinal length of the rotary drive cable.

4. The biopsy system of claim 1, wherein the remote unit includes at least one footswitch, wherein the at least one footswitch is configured to activate the motor of the remote unit to thereby supply power to the biopsy device for a sampling sequence.

5. The biopsy system of claim 1, wherein the remote unit includes a plurality of light emitters, wherein each light emitter of the plurality of light emitters is configured to convey information related to the biopsy device.

6. The biopsy system of claim 5, wherein the plurality of light emitters includes at least one light emitter configured to indicate a ready condition.

7. The biopsy system of claim 5, wherein the plurality of light emitters includes at least one light emitter configured to indicate a warning condition.

8. The biopsy system of claim 5, wherein the plurality of light emitters includes at least one light emitter configured to indicate an error condition.

9. The biopsy system of claim 1, wherein the remote unit further includes a biopsy device connector adapted to mechanically connect the remote unit to the biopsy device.

10. The biopsy system of claim 1, wherein the biopsy device connector is configured to couple to the rotary drive cable such that the rotary drive cable extends from the biopsy device to the remote unit, wherein the motor provides rotary power to the biopsy device via the rotary drive cable.

11. A biopsy system for use in an MRI suite, comprising:
    (a) a biopsy device, the biopsy device including:
        (i) a body,
        (ii) a needle extending distally from the body, wherein the needle includes a lateral aperture, and
        (iii) a cutter, wherein the cutter is movable relative to the lateral aperture of the needle to sever a tissue sample;
    (b) a control unit including a vacuum canister in communication with the biopsy device and a user interface and configured to be positioned outside of the MRI suite;
    (c) a first electrical cable;
    (d) a second rotary drive cable; and
    (e) a remote unit configured to be positioned within the MRI suite, the remote unit containing a motor to provide mechanical power to the biopsy device, wherein the remote unit is in electrical communication with the control unit via the first electrical cable, wherein the remote unit is in mechanical communication with the biopsy device by the second rotary drive cable, wherein the remote unit is configured to be independently positioned relative to the control unit.

12. The biopsy system of claim 11, wherein the second rotary drive cable is configured to supply rotary power to a cutter drive assembly disposed within the biopsy device such that the second rotary drive cable is configured to power rotation and translation of the cutter of the biopsy device.

13. The biopsy system of claim 11, wherein the remote unit is configured to lay on a floor of the MRI suite.

14. A biopsy system, comprising:
    (a) a biopsy device, the biopsy device including:
        (i) a body,
        (ii) a needle extending distally from the body, wherein the needle includes a lateral aperture, and
        (iii) a cutter, wherein the cutter is movable relative to the lateral aperture of the needle to sever a tissue sample;
    (b) a control unit having a vacuum canister in communication with the biopsy device and a user interface;
    (c) an electric cable;
    (d) a rotary drive cable;
    (e) a plurality of pneumatic tubes extending between the control unit and the biopsy device; and
    (f) a remote unit including a motor, wherein the motor is configured to power the biopsy device, wherein the remote unit is in communication with the control unit via the electric cable, wherein the remote unit is in mechanical communication with the biopsy device by the rotary drive cable, wherein the electric cable is configured to extend between the control unit and the remote unit while the remote unit is configured to be disposed adjacent to the biopsy device within an MRI suite and the control unit is configured to be positioned outside of the MRI suite.

15. The biopsy system of claim 14, wherein the rotary drive cable an end of the rotary drive cable is removably attached to a reusable portion of the body of the biopsy device.

16. The biopsy system of claim 14, wherein the remote unit includes a plurality of light emitters with each light emitter configured to communicate an operational status of the biopsy device to an operator, the plurality of light emitters including a first light emitter configured to communicate a ready status of the biopsy device, a first light emitter configured to communicate a warning status of the biopsy device, a third light emitter configured to communicate an error status of the biopsy device.

17. The biopsy system of claim 14, wherein the rotary drive cable is between three and six feet in length.

18. The biopsy system of claim 14, wherein the electrical cable is shorter than the rotary drive cable.

* * * * *